(12) United States Patent
Ling et al.

(10) Patent No.: US 12,162,840 B2
(45) Date of Patent: Dec. 10, 2024

(54) HERBICIDAL COMPOSITIONS

(71) Applicant: SYNGENTA PARTICIPATIONS AG, Basel (CH)

(72) Inventors: Kenneth Bruce Ling, Bracknell (GB); Christopher John Mathews, Bracknell (GB); Stephen Edward Shanahan, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 706 days.

(21) Appl. No.: 17/299,015

(22) PCT Filed: Nov. 28, 2019

(86) PCT No.: PCT/EP2019/082827
§ 371 (c)(1),
(2) Date: Jun. 2, 2021

(87) PCT Pub. No.: WO2020/114869
PCT Pub. Date: Jun. 11, 2020

(65) Prior Publication Data
US 2022/0119353 A1    Apr. 21, 2022

(30) Foreign Application Priority Data
Dec. 4, 2018 (GB) ..................... 1819747

(51) Int. Cl.
| | | |
|---|---|---|
| *A01N 43/58* | (2006.01) | |
| *A01N 43/36* | (2006.01) | |
| *A01P 13/00* | (2006.01) | |
| *C07D 207/12* | (2006.01) | |
| *C07D 237/16* | (2006.01) | |

(52) U.S. Cl.
CPC .......... *C07D 237/16* (2013.01); *A01N 43/36* (2013.01); *A01N 43/58* (2013.01); *A01P 13/00* (2021.08); *C07D 207/12* (2013.01)

(58) Field of Classification Search
CPC ..................................................... C07D 237/16
See application file for complete search history.

(56) References Cited

FOREIGN PATENT DOCUMENTS

| WO | 2009086041 A1 | 7/2009 |
|---|---|---|
| WO | 2011045271 A1 | 4/2011 |
| WO | 2013160126 A1 | 10/2013 |
| WO | 2015084796 A1 | 6/2015 |
| WO | 2016008816 A1 | 1/2016 |
| WO | 2018065311 A1 | 4/2018 |
| WO | 2019137851 A1 | 7/2019 |

OTHER PUBLICATIONS

GB Search Report for GB 1819747.5 mailed Jun. 4, 2019.
Written Opinon of the International Searching Authority and International Search Report of PCT/EP2019/082827, mailed Mar. 10, 2020.

*Primary Examiner* — Johann R Richter
*Assistant Examiner* — Danielle Johnson
(74) *Attorney, Agent, or Firm* — BakerHostetler; Toni-Junell Herbert

(57) ABSTRACT

The present invention relates to the use of herbicidal substituted phenyl-pyridazinediones and substituted phenyl-pyridazinone derivatives of formula (I), in combination with herbicidal pyrrolidinone derivatives of the formula (II) to control undesirable plant growth, in controlling weeds, including broad-leaved and/or narrow-leaved, monocotyledonous and/or dicotyledonous weeds, in crops of useful plants.

15 Claims, No Drawings

HERBICIDAL COMPOSITIONS

CROSS-REFERENCE TO RELATED APPLICATIONS

This application is a 371 National Stage application of International Application No. PCT/EP2019/082827 filed Nov. 28, 2019, claims priority to GB 1819747.5 filed Dec. 4, 2018, the entire contents of these applications are hereby incorporated by reference.

The present invention relates novel herbicidal compositions and their use in controlling plants or inhibiting plant growth.

Herbicidal pyridazinones are known from WO2009/086041. In addition, herbicidal 5/6 membered heterocyclyl-substituted pyridazinones are known from WO 2011/045271. Whilst WO2013/160126 describes indolyl-pyridazinone derivatives, which exhibit herbicidal activity.

Herbicidal pyrrolidinone derivatives of the formula

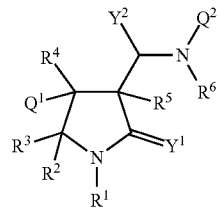

are described in WO2015/084796.

The present invention is based on the finding that substituted phenyl-pyridazine-diones and substituted phenyl-pyridazinone derivatives of formula (I) as defined infra, exhibit surprisingly good herbicidal activity, in particular in combination with herbicidal pyrrolidinone derivatives of formula (II) also described infra.

In one aspect, therefore, the present invention provides a composition comprising:

(A) a compound of formula (I)

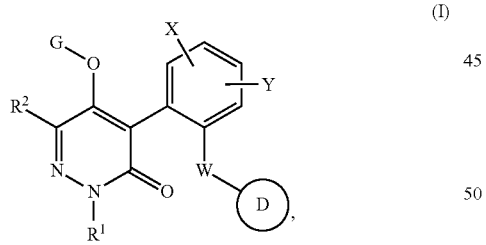

or a salt or N-oxide thereof, wherein $R^1$ is selected from the group consisting of $C_1$-$C_4$ alkyl, $C_3$-$C_6$cycloalkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, cyano-$C_1$-$C_4$alkyl, $C_2$-$C_4$ haloalkenyl, $C_2$-$C_4$ alkynyl and $C_2$-$C_4$ haloalkynyl;

$R^2$ is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, —S(O)$_m$$C_1$-$C_6$alkyl, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl; G is hydrogen, or C(O)R$^3$;

$R^3$ is selected from the group consisting of $C_1$-$C_6$alkyl, $C_1$-$C_6$alkenyl, $C_1$-$C_6$alkynyl, $C_1$-$C_6$alkyl-S—, —NR$^4$R$^5$ and phenyl optionally substituted by one or more R$^6$—;

$R^4$ and $R^5$ are independently selected from the group consisting of $C_1$-$C_6$ alkyl and $C_1$-$C_6$ alkoxy, or $R^4$ and $R^5$ together can form a morpholinyl ring;

$R^6$ is selected from the group consisting of halogen, cyano, nitro, $C_1$-$C_3$alkyl, $C_1$-$C_3$haloalky, $C_1$-$C_3$alkoxy and $C_1$-$C_3$haloalkoxy;

X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;

D is a substituted or unsubstituted monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$;

each $R^8$ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, $C_1$-$C_6$alkyl-S(O)$_m$—, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

m is an integer of 0, 1, or 2; and each $R^9$ is independently, $C_1$-$C_4$ alkyl, $C_3$-$C_6$alkoxy, $C_1$-$C_2$alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl or $C_2$-$C_4$ haloalkynyl;

or,

D is a substituted or unsubstituted phenyl ring (Dp),

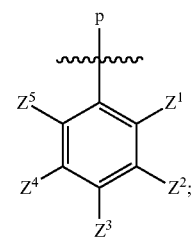

wherein p denotes the point of attachment of (Dp) to the rest of the molecule;

$Z^1$, $Z^2$, $Z^3$, $Z^4$, and $Z^5$ are each independently selected from hydrogen, $C_1$-$C_3$ alkyl, $C_1$-$C_3$ alkoxy, $C_1$-$C_3$haloalkyl, $C_1$-$C_3$haloalkoxy, or halogen;

and

W is either

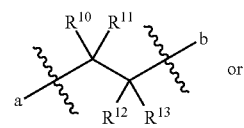

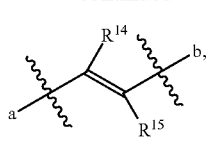

wherein
"a" denotes the point of attachment to the phenyl-pyridazinone/phenyl-pyridazine dione moiety,
"b" denotes the point of attachment to ring D,
$R^{10}$, $R^{12}$, $R^{14}$ and $R^{15}$ are each independently hydrogen, $C_1$-$C_3$alkyl, or $C_1$-$C_3$haloalkyl; or
$R^{10}$ and $R^{12}$ together with the carbon atoms to which they are joined form a $C_3$-$C_6$ carbocyclic ring;
$R^{11}$ and $R^{13}$ are each independently hydrogen, halogen, $C_1$-$C_3$alkyl, or $C_1$-$C_3$haloalkyl, provided that when one of $R^{11}$ or $R^{13}$ is halogen, $C_1$-$C_3$alkyl or $C_1$-$C_3$haloalkyl, the other is hydrogen;
and
(B) one or more compounds of formula (II)

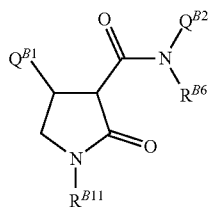

wherein,
$R^{B11}$ is H, $C_1$-$C_6$alkyl, $C_1$-$C_6$ haloalkyl or $C_4$-$C_8$ cycloalkyl;
$R^{B6}$ is H, $C_1$-$C_6$alkyl, or $C_1$-$C_6$alkoxy;
$Q^{B1}$ is an optionally substituted ring system, selected from the group consisting of phenyl, thienyl, pyridinyl, benzodioxolyl, naphthyl, naphthalenyl, benzofuranyl, furanyl, benzothiophenyl, and pyrazolyl, wherein when substituted said ring system is substituted by 1 to 3 $R^{B4}$;
$Q^{B2}$ is an optionally substituted ring system, selected from the group consisting of phenyl, pyridinyl, benzodioxolyl, pyridinone, thiadazolyl, thiazolyl, and oxazolyl, wherein when substituted said ring system is substituted by 1 to 3 $R^{B5}$;
each $R^{B4}$ is independently halogen, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, cyano, $C_1$-$C_6$alkylthio, $C_1$-$C_6$alkylsulphinyl, $C_1$-$C_6$alkylsulphonyl, $SF_5$, $NHR^{B8}$, phenyl optionally substituted by 1-3 $R^{B7}$, or pyrazolyl optionally substituted by 1-3 $R^{B7}$;
each $R^{B5}$ is independently halogen, $C_1$-$C_6$alkyl, $C_1$-$C_6$haloalkyl, $C_1$-$C_6$alkoxy, $C_1$-$C_6$haloalkoxy, cyano, nitro, $C_1$-$C_6$alkylthio, $C_1$-$C_6$alkylsulphinyl, or $C_1$-$C_6$alkylsulphonyl;
each $R^{B7}$ is independently $C_1$-$C_6$alkyl, halogen, or $C_1$-$C_6$haloalkyl; and
$R^{B8}$ is $C_1$-$C_4$alkoxycarbonyl; or an N-oxide, or a salt form thereof.

In a second aspect, the invention provides the use of a composition of the invention as a herbicide.

In a third aspect, the invention provides a method of controlling plants, comprising applying to the plants or to the locus of the plants, a herbicidally effective amount of a composition of the invention.

In a fourth aspect, the invention provides a method of inhibiting plant growth, comprising applying to the plants or to the locus thereof, a herbicidally effective amount of a composition of the invention.

In a fifth aspect, the invention provides a method of controlling weeds in crops of useful plants, comprising applying to the weeds or to the locus of the weeds, or to the useful plants or to the locus of the useful plants, a herbicidally effective amount of a composition of the invention.

In a sixth aspect, the invention provides a method of selectively controlling grasses and/or weeds in crops of useful plants which comprises applying to the useful plants or locus thereof or to the area of cultivation a herbicidally effective amount of a composition of the invention.

When active ingredients are combined, the activity to be expected (E) for any given active ingredient combination obeys the so-called Colby Formula and can be calculated as follows (Colby, S. R., Calculating synergistic and antagonistic responses of herbicide combination, Weeds, Vol. 15, pages 20-22; 1967):
ppm=milligrams of active ingredient (a.i.) per liter
X=% action by first active ingredient using p ppm of the active ingredient
Y=% action by second active ingredient sing q ppm of the active ingredient.
According to Colby, the expected action of active ingredients A+B using p+q ppm of active ingredient is represented by the following formula:

$$E = X + Y - \frac{X \cdot Y}{100}$$

If the action actually observed (O) is greater than the expected action E then the action of the combination is super-additive, i.e. there is a synergistic effect. In mathematical terms, synergism corresponds to a positive value for the difference of (O−E). In the case of purely complementary addition of activities (expected activity), said difference (O−E) is zero. A negative value of said difference (O−E) signals a loss of activity compared to the expected activity.

Compounds of formula (I) and formula (II) are both effective herbicidal compounds, as shown herein with respect to compounds of formula (I) and as shown in WO2015/084796 for compounds of formula (II). Accordingly, the combination of the present invention takes advantage of their additive activity, and certain embodiments may exhibit a synergistic effect. This occurs whenever the action of an active ingredient combination is greater than the sum of the actions of the individual components.

Furthermore, besides any actual synergistic action with respect to herbicidal activity, the composition according to the invention may also exhibit further surprising advantageous properties. Examples of such advantageous properties include improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

In addition, it is also possible that the composition of the invention may show increased crop tolerance, when compared with the effect of the compound A alone. This occurs when the action of an active ingredient combination is less damaging to a useful crop than the action of one of the active ingredients alone.

Compounds of formulae (I) and/or (II) may contain asymmetric centres and thus may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are di-substituted alkenes, these may be present in E or Z form or as mixtures of both in any proportion.

Furthermore, compounds of formula (I) may be in equilibrium with alternative tautomeric forms. For example, a compound of formula (I-i), i.e. a compound of formula (I) wherein $R^2$ is hydrogen and G is hydrogen, can be drawn in at least three tautomeric forms:

ring heteroatom and consists of a single ring. Preferably, single rings will contain 1, 2 or 3 ring heteroatoms selected independently from nitrogen, oxygen and sulfur. Typically "heteroaryl" is furyl, thienyl, pyrrolyl, pyrazolyl, imidazolyl, 1,2,3triazolyl, 1,2,4triazolyl, oxazolyl, isoxazolyl, thiazolyl, isothiazolyl, 1,2,4oxadiazolyl, 1,3,4oxadiazolyl, 1,2,5oxadiazolyl, 1,2,3thiadiazolyl, 1,2,4thiadiazolyl, 1,3,4thiadiazolyl, 1,2,5thiadiazolyl, pyridyl, pyrimidinyl, pyridazinyl, pyrazinyl, 1,2,3triazinyl, 1,2,4triazinyl, or 1,3,5triazinyl.

Heterocyclyl groups and heterocyclic rings (either alone or as part of a larger group, such as heterocyclyl-alkyl-) are ring systems containing at least one heteroatom and can be in mono- or bi-cyclic form. Preferably, heterocyclyl groups will contain up to two heteroatoms which will preferably be chosen from nitrogen, oxygen and sulfur. Examples of heterocyclic groups include oxetanyl, thietanyl, azetidinyl and 7-oxa-bicyclo[2.2.1]hept-2-yl. Heterocyclyl groups containing a single oxygen atom as heteroatom are most preferred. The heterocyclyl groups are preferably 3- to 8-membered, more preferably 3- to 6-membered rings.

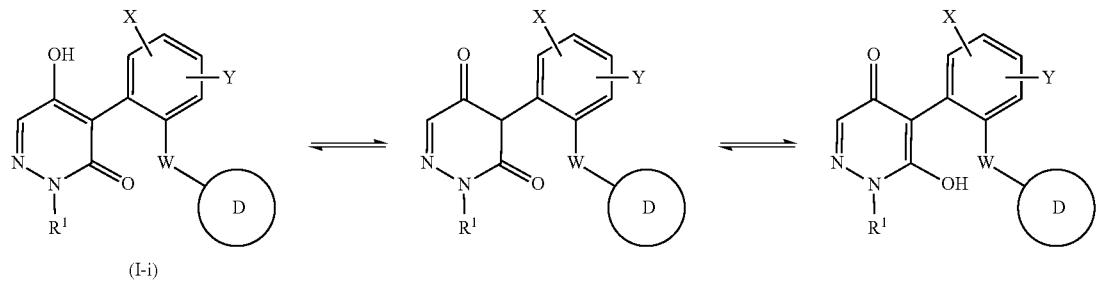

(I-i)

It should be appreciated that all tautomeric forms (single tautomer or mixtures thereof), racemic mixtures and single isomers of compounds of formula (I) and/or formula (II) may be incorporated in compositions of the invention and thus fall within the scope of the present invention.

The following terms are applicable to compounds of formula (I) and of formula (II).

Each alkyl moiety either alone or as part of a larger group (such as alkoxy, alkylthio, alkoxycarbonyl, alkylcarbonyl, alkylaminocarbonyl, or dialkylaminocarbonyl, et al.) may be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups are generally $C_1$-$C_6$alkyl groups (except where already defined more narrowly), but are preferably $C_1$-$C_4$alkyl or $C_1$-$C_3$alkyl groups, and, more preferably, are $C_1C_2$alkyl groups (such as methyl).

Alkenyl and alkynyl moieties can be in the form of straight or branched chains, and the alkenyl moieties, where appropriate, can be of either the (E)- or (Z)-configuration. The alkenyl or alkynyl moieties are typically $C_2$-$C_4$alkenyl or $C_2$-$C_4$alkynyl, more specifically vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Preferably, the term cycloalkyl refers to cyclopropyl, cyclobutyl, cyclopentyl or cyclohexyl.

In the context of the present specification the term "aryl" preferably means phenyl. The term "heteroaryl" as used herein means an aromatic ring system containing at least one Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents may be present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-$S(O)_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

As stated herein, compositions of the invention comprise (A) a compound of formula (I) and (B) a compound of formula (II). More details with respect to compounds of formula (I) are provided below.

The group Q

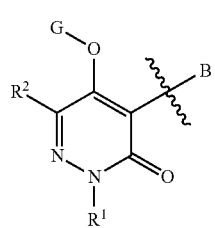

(Q)

is referred to herein as the pyridazine dione/pyridazinone moiety, wherein B denotes the point of attachment to the rest of the molecule (i.e. to the optionally substituted phenyl-W-D moiety).

The present invention also includes the use of agronomically acceptable salts that the compounds of formula (I) may form with amines (for example ammonia, dimethylamine and triethylamine), alkali metal and alkaline earth metal bases or quaternary ammonium bases.

Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used. The compounds of formula (I) for use in the invention also include hydrates which may be formed during the salt formation. Where the term "compound of formula (I)" is used with respect to the present invention, the skilled man would readily appreciate that this equally refers to any suitable agronomically acceptable salt and or hydrate of said compound.

Preferred values of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, W, Dp, G, X, Y, Z, and m are as set out below, and a compound of formula (I) according for use in the invention may comprise any combination of said values. The skilled man will appreciate that values for any specified set of embodiments may combined with values for any other set of embodiments where such combinations are not mutually exclusive.

Preferably $R^1$ is selected from the group consisting of methyl, ethyl, propyl (in particular n- or c-propyl), propargyl or $C_1$haloalkyl. More preferably $R^1$ is methyl, ethyl, cyclopropyl, propargyl or $C_1$fluoroalkyl. More preferably still $R^1$ is methyl, ethyl, cyclopropyl or propargyl.

Preferably $R^2$ is selected from the group consisting of hydrogen, $C_1$-$C_6$alkyl, $C_1$-$C_6$haloalkyl, $C_1$-$C_6$alkoxy, $C_1$-$C_3$alkoxy-$C_1$-$C_3$alkyl, $C_3$-$C_6$cycloalkyl, $C_2$-$C_6$ alkenyl, $C_2$-$C_6$ haloalkenyl, $C_2$-$C_6$ alkynyl and $C_2$-$C_6$ haloalkynyl. More preferably $R^2$ is selected from the group consisting of methyl, ethyl, cyclopropyl, trifluoromethyl and methoxymethyl, more preferably still cyclopropyl, trifluoromethyl or methyl, most preferably cyclopropyl or methyl. In one set of embodiments of the present invention $R^2$ is hydrogen. In a further set of embodiments $R^2$ is cyclopropyl, in a third set of embodiments $R^2$ is methyl, and in a fourth set of embodiments $R^2$ is trifluoromethyl.

As described herein, G may be hydrogen or —C(O)—$R^3$, and $R^3$ is selected from the group consisting of $C_1$-$C_6$alkyl, $C_2$-$C_6$alkenyl, $C_2$-$C_6$alkynyl, $C_1$-$C_6$alkyl-S—, $C_1$-$C_6$alkoxy, —NR$^4$R$^5$ and phenyl optionally substituted by one or more $R^6$. As defined herein, $R^4$ and $R^5$ are independently selected from the group consisting of $C_1$-$C_6$ alkyl, $C_1$-$C_6$ alkoxy-; or they can together form a morpholinyl ring. Preferably $R^4$ and $R^5$ are each independently selected from the group consisting of methyl, ethyl, propyl, methoxy, ethoxy and propoxy. $R^6$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy.

Preferably $R^3$ is $C_1$-$C_4$ alkyl, $C_2$-$C_3$alkenyl, $C_2$-$C_3$alkynyl, —$C_1$-$C_3$alkoxy, or —NR$^4$R$^5$ wherein $R^4$ and $R^5$ together form a morpholinyl ring. More preferably $R^3$ is isopropyl, t-butyl, methyl, ethyl, propargyl or methoxy.

In one set of embodiments G is hydrogen or —C(O)—$R^3$, wherein $R^3$ is $C_1$-$C_4$ alkyl, $C_2$-$C_3$alkenyl, $C_2$-$C_3$alkynyl or —$C_1$-$C_3$alkoxy. In a further set of embodiments G is hydrogen or —C(O)—$R^3$ wherein $R^3$ is isopropyl, t-butyl, methyl, ethyl, propargyl or methoxy. However, it is particularly preferred that G is hydrogen, or —C(O)—$R^3$ wherein $R^3$ is isopropyl.

X is preferably hydrogen, halogen, or $C_1$haloalkyl, more preferably hydrogen, fluoro, chloro, bromo, or $C_1$fluoroalkyl and more preferably still, hydrogen, fluoro, chloro or trifluoromethyl. In one set of embodiments it is preferred that X is ortho with respect to the pyridazinone/pyridazine-dione moiety (group Q). It is particularly preferred that X is fluoro, chloro or $C_1$-haloalkyl (in particular $C_1$fluoroalkyl) and is ortho with respect to pyridazinone/pyridazine-dione moiety (group Q).

Y is preferably hydrogen, $C_1$-$C_3$ alkyl, $C_1$-$C_3$haloalkyl, or halogen. More preferably Y is hydrogen, chloro, fluoro, or bromo.

In one set of embodiments it is preferred that Y is ortho with respect to the —W-D moiety.

In a further set of embodiments, Y is para with respect to the pyridazinone/pyridazine-dione moiety (group Q).

It is particularly preferred that Y is ortho with respect to the —W-D moiety and is halogen, in particular chloro or fluoro; more preferably chloro.

As described herein, D is an substituted or unsubstituted phenyl ring (Dp) or is a substituted or unsubstituted 5- or 6-membered monocyclic heteroaryl ring containing 1, 2, or 3 heteroatoms independently selected from oxygen, nitrogen and sulphur, and wherein when D is a substituted heteroaryl ring it is substituted on at least one ring carbon atom with $R^8$ and/or on a ring nitrogen atom with $R^9$. Where D is a substituted or unsubstituted 5- or 6-membered monocyclic heteroaryl ring, it is preferably a substituted (as described herein) or unsubstituted furyl, thienyl, pyrrolyl, pyrazolyl, imidazolyl, 1,2,3triazolyl, 1,2,4triazolyl, oxazolyl, isoxazolyl, thiazolyl, isothiazolyl, 1,2,4oxadiazolyl, 1,3,4oxadiazolyl, 1,2,5oxadiazolyl, 1,2,3thiadiazolyl, 1,2,4thiadiazolyl, 1,3,4thiadiazolyl, 1,2,5thiadiazolyl, pyridyl, pyridonyl, pyrimidinyl, pyridazinyl, pyrazinyl, 1,2,3triazinyl, 1,2,4triazinyl, or 1,3,5triazinyl ring.

More preferably in such embodiments, D is a substituted (as described herein) or unsubstituted pyrazolyl, imidazolyl, oxazolyl, isoxazolyl, thiazolyl, isothiazolyl, pyridyl, pyridonyl, pyrimidinyl, pyridazinyl, or pyrazinyl ring.

More preferably still in such embodiments, D is a substituted (as described herein) or unsubstituted, oxazolyl, thiazolyl, or, pyridyl, ring. In certain embodiments, D is a substituted or unsubstituted pyridyl-, or substituted or unsubstituted thiazolyl ring.

Preferably each $R^8$ is independently oxo, $C_1$-$C_4$alkyl, $C_1$-$C_4$haloalkyl, halogen, cyano, hydroxyl, $C_1$-$C_4$alkoxy, or $C_1$-$C_4$alkylthio, more preferably each $R^8$ is independently halogen, or $C_1$-$C_4$haloalkyl.

Preferably each $R^9$ is independently $C_1$-$C_4$alkyl, $C_1$-$C_4$haloalkyl, hydroxyl, $C_1$-$C_4$alkoxy, or $C_1$-$C_4$alkylthio.

In particular embodiments where D is a substituted or unsubstituted 5- or 6-membered monocyclic heteroaryl ring as described above, D is selected from the group consisting of 4-chloro-3-pyridyl, 4-trifluoromethylpyridyl, 3-pyridyl, and 2-chloro-thiazo-5-yl.

However, as stated above D may alternatively be a substituted or unsubstituted phenyl ring (Dp)

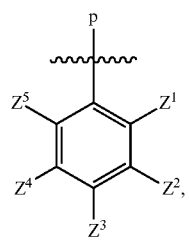

(Dp)

wherein $Z^1$, $Z^2$, $Z^3$, $Z^4$, and $Z^5$ are each independently selected from hydrogen, cyano, $C_1$-$C_3$ alkyl, $C_1$-$C_3$ alkoxy, $C_1$-$C_3$haloalkyl, $C_1$-$C_3$haloalkoxy, or halogen; and p is the point of attachment to the rest of the molecule.

Preferably $Z^1$, $Z^2$, $Z^3$, $Z^4$, and $Z^5$ are each independently selected from hydrogen, cyano, halogen (in particular chloro or fluoro), methyl, methoxy, and trifluoromethyl.

In one set of embodiments each of $Z^1$, $Z^2$, $Z^4$, and $Z^5$ are hydrogen, and $Z^3$ is not hydrogen. Preferably in this set of embodiments, $Z^3$ is halogen, more preferably chloro.

In a further set of embodiments, each of $Z^1$, $Z^4$ and $Z^5$ are hydrogen, and $Z^2$ and $Z^3$ are not hydrogen. In this set of embodiments it is particularly preferred that $Z^2$ and $Z^3$ are each independently halogen, and more preferred that $Z^2$ and $Z^3$ are both chloro.

In one particularly preferred set of embodiments $Z^1$, $Z^2$, $Z^3$, $Z^4$ and $Z^5$ all carry hydrogen.

In further embodiments, where D is Dp, Dp is selected from the group consisting of 4-chloro-phenyl, 4-trifluoromethyl-phenyl, 4-cyanophenyl, 4-fluoro-phenyl, 3,4-difluoro-phenyl, 2-trifluoromethyl-phenyl and 4-tolyl.

W acts as a linker moiety, linking ring D to the rest of the molecule (i.e. to the phenyl-pyridazinone/phenyl-pyridazine dione moiety). Compounds of formula (I) wherein the linker is W1 are herbicidal, whereas compounds of formula (I) wherein the linker is W2 may be not only herbicidal, but also useful intermediates in the production of compounds of formula (I) bearing W1 linkers. Thus, in one set of embodiments, W is W1, whereas in a second set of embodiments, W is W2.

Specific examples of W include —$CH_2$—$CH_2$—, and —CH═CH—, cis

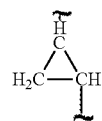

and trans

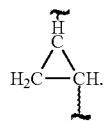

In preferred embodiments W is either —$CH_2$—$CH_2$—, or —CH═CH—.

Preferably $R^{10}$, $R^{11}$, $R^{12}$ and $R^{13}$ are each independently selected from hydrogen or $C_1$-$C_3$ alkyl. In one set of embodiments $R^{10}$, $R^{11}$, $R^{12}$, and $R^{13}$ are all hydrogen.

Preferably $R^{14}$ and $R^{15}$ are each independently selected from hydrogen or $C_1$-$C_3$alkyl. In one set of embodiments $R^{14}$ and $R^{15}$ are both hydrogen.

Table 1 below provides 308 specific examples of compounds of formula (I) for use as component in (A) in compositions of the invention.

TABLE 1

Herbicidal compounds of formula (I) for use as (A) in the present invention. The numbering system used to describe the positions of X and Y is shown for the purposes of clarity only.

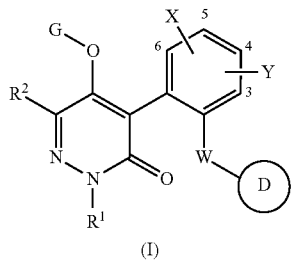

(I)

| Compound No. | $R^1$ | $R^2$ | G | X | Y | W | D |
|---|---|---|---|---|---|---|---|
| 1.001 | —Me | —Me | —H | 6-F | 3-Cl | —$CH_2$—$CH_2$— | —Ph |
| 1.002 | —Me | —Me | —H | 6-F | 3-Cl | (E) —CH═CH— | —Ph |

TABLE 1-continued

Herbicidal compounds of formula (I) for use as (A) in the present invention. The numbering system used to describe the positions of X and Y is shown for the purposes of clarity only.

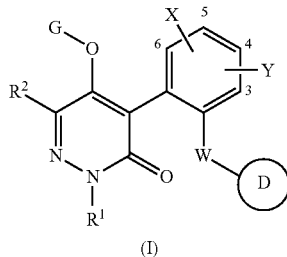

(I)

| Compound No. | R¹ | R² | G | X | Y | W | D |
|---|---|---|---|---|---|---|---|
| 1.003 | —Me | —Me | —H | 6-F | 3-Cl | trans cyclopropyl | —Ph |
| 1.004 | —Me | —Me | —H | 6-F | 3-Cl | cis cyclopropyl | —Ph |
| 1.005 | —Me | —Me | —H | 6-Cl | 3-Cl | —CH$_2$—CH$_2$— | —Ph |
| 1.006 | —Me | —Me | —H | 6-Cl | 3-Cl | trans cyclopropyl | —Ph |
| 1.007 | —Me | —Me | —H | 6-Cl | 3-Cl | cis cyclopropyl | —Ph |
| 1.008 | —CH$_2$—C≡CH | —Me | —H | 6-F | 3-Cl | —CH$_2$—CH$_2$— | —Ph |
| 1.009 | —cyclopropyl | —Me | —H | 6-F | 3-Cl | —CH$_2$—CH$_2$— | —Ph |
| 1.010 | —CH$_2$—C≡CH | —Me | —H | 6-Cl | 3-Cl | —CH$_2$—CH$_2$— | —Ph |
| 1.011 | —cyclopropyl | —Me | —H | 6-Cl | 3-Cl | —CH$_2$—CH$_2$— | —Ph |
| 1.012 | —Me | —Me | —H | 6-F | 3-Cl | —CH$_2$—CH$_2$— | 4-chloro-phenyl- |
| 1.013 | —CH$_2$—C≡CH | —Me | —H | 6-F | 3-Cl | —CH$_2$—CH$_2$— | 4-chloro-phenyl- |
| 1.014 | —cyclopropyl | —Me | —H | 6-F | 3-Cl | —CH$_2$—CH$_2$— | 4-chloro-phenyl- |
| 1.015 | —Me | —Me | —H | 6-Cl | 3-Cl | —CH$_2$—CH$_2$— | 4-chloro-phenyl- |
| 1.016 | —CH$_2$—C≡CH | —Me | —H | 6-Cl | 3-Cl | —CH$_2$—CH$_2$— | 4-chloro-phenyl- |
| 1.017 | —cyclopropyl | —Me | —H | 6-Cl | 3-Cl | —CH$_2$—CH$_2$— | 4-chloro-phenyl- |
| 1.018 | —Me | —Me | —H | 6-F | 3-Cl | —CH$_2$—CH$_2$— | 4-trifluoromethyl-phenyl- |
| 1.019 | —CH$_2$—C≡CH | —Me | —H | 6-F | 3-Cl | —CH$_2$—CH$_2$— | 4-trifluoromethyl-phenyl- |
| 1.020 | —cyclopropyl | —Me | —H | 6-F | 3-Cl | —CH$_2$—CH$_2$— | 4-trifluoromethyl-phenyl- |
| 1.021 | —Me | —Me | —H | 6-Cl | 3-Cl | —CH$_2$—CH$_2$— | 4-trifluoromethyl-phenyl- |
| 1.022 | —CH$_2$—C≡CH | —Me | —H | 6-Cl | 3-Cl | —CH$_2$—CH$_2$— | 4-trifluoromethyl-phenyl- |
| 1.023 | —cyclopropyl | —Me | —H | 6-Cl | 3-Cl | —CH$_2$—CH$_2$— | 4-trifluoromethyl-phenyl- |

TABLE 1-continued

Herbicidal compounds of formula (I) for use as (A) in the present invention. The numbering system used to describe the positions of X and Y is shown for the purposes of clarity only.

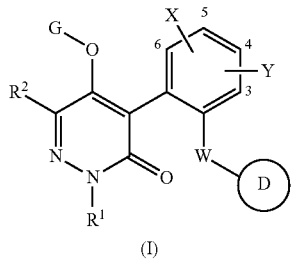

(I)

| Compound No. | R¹ | R² | G | X | Y | W | D |
|---|---|---|---|---|---|---|---|
| 1.024 | —Me | —Me | —H | 6-F | 3-Cl | —CH₂—CH₂— | 4-cyano-phenyl- |
| 1.025 | —CH₂—C≡CH | —Me | —H | 6-F | 3-Cl | —CH₂—CH₂— | 4-cyano-phenyl- |
| 1.026 | —cyclopropyl | —Me | —H | 6-F | 3-Cl | —CH₂—CH₂— | 4-cyano-phenyl- |
| 1.027 | —Me | —Me | —H | 6-Cl | 3-Cl | —CH₂—CH₂— | 4-cyano-phenyl- |
| 1.028 | —CH₂—C≡CH | —Me | —H | 6-Cl | 3-Cl | —CH₂—CH₂— | 4-cyano-phenyl- |
| 1.029 | —cyclopropyl | —Me | —H | 6-Cl | 3-Cl | —CH₂—CH₂— | 4-cyano-phenyl- |
| 1.030 | —Me | —Me | —H | 6-F | 3-Cl | —CH₂—CH₂— | 4-chloro-3-pyridyl- |
| 1.031 | —CH₂—C≡CH | —Me | —H | 6-F | 3-Cl | —CH₂—CH₂— | 4-chloro-3-pyridyl- |
| 1.032 | —cyclopropyl | —Me | —H | 6-F | 3-Cl | —CH₂—CH₂— | 4-chloro-3-pyridyl- |
| 1.033 | —Me | —Me | —H | 6-Cl | 3-Cl | —CH₂—CH₂— | 4-chloro-3-pyridyl- |
| 1.034 | —CH₂—C≡CH | —Me | —H | 6-Cl | 3-Cl | —CH₂—CH₂— | 4-chloro-3-pyridyl- |
| 1.035 | —cyclopropyl | —Me | —H | 6-Cl | 3-Cl | —CH₂—CH₂— | 4-chloro-3-pyridyl- |
| 1.036 | —Me | —Me | —H | 6-F | 3-Cl | —CH₂—CH₂— | 2-chlorothiazol-5-yl- |
| 1.037 | —CH₂—C≡CH | —Me | —H | 6-F | 3-Cl | —CH₂—CH₂— | 2-chlorothiazol-5-yl- |
| 1.038 | —cyclopropyl | —Me | —H | 6-F | 3-Cl | —CH₂—CH₂— | 2-chlorothiazol-5-yl- |
| 1.039 | —Me | —Me | —H | 6-Cl | 3-Cl | —CH₂—CH₂— | 2-chlorothiazol-5-yl- |
| 1.040 | —CH₂—C≡CH | —Me | —H | 6-Cl | 3-Cl | —CH₂—CH₂— | 2-chlorothiazol-5-yl- |
| 1.041 | —cyclopropyl | —Me | —H | 6-Cl | 3-Cl | —CH₂—CH₂— | 2-chlorothiazol-5-yl- |
| 1.042 | —Me | —Me | —H | 6-F | 3-Cl | —CH₂—CH₂— | 4-trifluoromethy1-3-pyridyl- |
| 1.043 | —CH₂—C≡CH | —Me | —H | 6-F | 3-Cl | —CH₂—CH₂— | 4-trifluoromethy1-3-pyridyl- |
| 1.044 | —cyclopropyl | —Me | —H | 6-F | 3-Cl | —CH₂—CH₂— | 4-trifluoromethy1-3-pyridyl- |
| 1.045 | —Me | —Me | —H | 6-Cl | 3-Cl | —CH₂—CH₂— | 4-trifluoromethy1-3-pyridyl- |
| 1.046 | —CH₂—C≡CH | —Me | —H | 6-Cl | 3-Cl | —CH₂—CH₂— | 4-trifluoromethy1-3-pyridyl- |
| 1.047 | —cyclopropyl | —Me | —H | 6-Cl | 3-Cl | —CH₂—CH₂— | 4-trifluoromethy1-3-pyridyl- |
| 1.048 | —Me | —Me | —H | 6-F | 3-Cl | —CH₂—CH₂— | 4-fluoro-phenyl- |
| 1.049 | —CH₂—C≡CH | —Me | —H | 6-F | 3-Cl | —CH₂—CH₂— | 4-fluoro-phenyl- |
| 1.050 | —cyclopropyl | —Me | —H | 6-F | 3-Cl | —CH₂—CH₂— | 4-fluoro-phenyl- |
| 1.051 | —Me | —Me | —H | 6-Cl | 3-Cl | —CH₂—CH₂— | 4-fluoro-phenyl- |
| 1.052 | —CH₂—C≡CH | —Me | —H | 6-Cl | 3-Cl | —CH₂—CH₂— | 4-fluoro-phenyl- |
| 1.053 | —cyclopropyl | —Me | —H | 6-Cl | 3-Cl | —CH₂—CH₂— | 4-fluoro-phenyl- |
| 1.054 | —Me | —Me | —H | 6-F | 3-Cl | —CH₂—CH₂— | 3-pyridyl- |
| 1.055 | —CH₂—C≡CH | —Me | —H | 6-F | 3-Cl | —CH₂—CH₂— | 3-pyridyl- |
| 1.056 | —cyclopropyl | —Me | —H | 6-F | 3-Cl | —CH₂—CH₂— | 3-pyridyl- |
| 1.057 | —Me | —Me | —H | 6-Cl | 3-Cl | —CH₂—CH₂— | 3-pyridyl- |
| 1.058 | —CH₂—C≡CH | —Me | —H | 6-Cl | 3-Cl | —CH₂—CH₂— | 3-pyridyl- |
| 1.059 | —cyclopropyl | —Me | —H | 6-Cl | 3-Cl | —CH₂—CH₂— | 3-pyridyl- |
| 1.060 | —Me | —Me | —H | 6-F | 3-Cl | —CH₂—CH₂— | 3,4-difluoro-phenyl- |
| 1.061 | —CH₂—C≡CH | —Me | —H | 6-F | 3-Cl | —CH₂—CH₂— | 3,4-difluoro-phenyl- |
| 1.062 | —cyclopropyl | —Me | —H | 6-F | 3-Cl | —CH₂—CH₂— | 3,4-difluoro-phenyl- |
| 1.063 | —Me | —Me | —H | 6-Cl | 3-Cl | —CH₂—CH₂— | 3,4-difluoro-phenyl- |
| 1.064 | —CH₂—C≡CH | —Me | —H | 6-Cl | 3-Cl | —CH₂—CH₂— | 3,4-difluoro-phenyl- |
| 1.065 | —cyclopropyl | —Me | —H | 6-Cl | 3-Cl | —CH₂—CH₂— | 3,4-difluoro-phenyl- |
| 1.066 | —Me | —Me | —H | 6-F | 3-Cl | —CH₂—CH₂— | 2-trifluoromethyl-phenyl- |
| 1.067 | —CH₂—C≡CH | —Me | —H | 6-F | 3-Cl | —CH₂—CH₂— | 2-trifluoromethyl-phenyl- |
| 1.068 | —cyclopropyl | —Me | —H | 6-F | 3-Cl | —CH₂—CH₂— | 2-trifluoromethyl-phenyl- |
| 1.069 | —Me | —Me | —H | 6-Cl | 3-Cl | —CH₂—CH₂— | 2-trifluoromethyl-phenyl- |
| 1.070 | —CH₂—C≡CH | —Me | —H | 6-Cl | 3-Cl | —CH₂—CH₂— | 2-trifluoromethyl-phenyl- |
| 1.071 | —cyclopropyl | —Me | —H | 6-Cl | 3-Cl | —CH₂—CH₂— | 2-trifluoromethyl-phenyl- |
| 1.072 | —Me | —Me | —H | 6-F | 3-Cl | —CH₂—CH₂— | 4-tolyl- |
| 1.073 | —CH₂—C≡CH | —Me | —H | 6-F | 3-Cl | —CH₂—CH₂— | 4-tolyl- |
| 1.074 | —cyclopropyl | —Me | —H | 6-F | 3-Cl | —CH₂—CH₂— | 4-tolyl- |
| 1.075 | —Me | —Me | —H | 6-Cl | 3-Cl | —CH₂—CH₂— | 4-tolyl- |
| 1.076 | —CH₂—C≡CH | —Me | —H | 6-Cl | 3-Cl | —CH₂—CH₂— | 4-tolyl- |
| 1.077 | —cyclopropyl | —Me | —H | 6-Cl | 3-Cl | —CH₂—CH₂— | 4-tolyl- |
| 1.078 | —Me | —Me | —(C═O)ⁱPr | 6-F | 3-Cl | —CH₂—CH₂— | —Ph |

TABLE 1-continued

Herbicidal compounds of formula (I) for use as (A) in the present invention. The numbering system used to describe the positions of X and Y is shown for the purposes of clarity only.

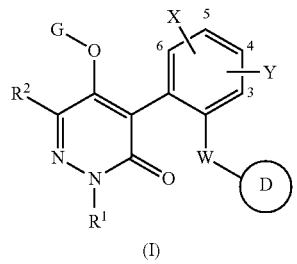

(I)

| Compound No. | R¹ | R² | G | X | Y | W | D |
|---|---|---|---|---|---|---|---|
| 1.079 | —Me | —Me | —(C=O)ⁱPr | 6-F | 3-Cl | (E) —CH=CH— | —Ph |
| 1.080 | —Me | —Me | —(C=O)ⁱPr | 6-F | 3-Cl | trans cyclopropyl | —Ph |
| 1.081 | —Me | —Me | —(C=O)ⁱPr | 6-F | 3-Cl | cis cyclopropyl | —Ph |
| 1.082 | —Me | —Me | —(C=O)ⁱPr | 6-Cl | 3-Cl | —CH₂—CH₂— | —Ph |
| 1.083 | —Me | —Me | —(C=O)ⁱPr | 6-Cl | 3-Cl | trans cyclopropyl | —Ph |
| 1.084 | —Me | —Me | —(C=O)ⁱPr | 6-Cl | 3-Cl | cis cyclopropyl | —Ph |
| 1.085 | —CH₂—C=CH—Me | —Me | —(C=O)ⁱPr | 6-F | 3-Cl | —CH₂—CH₂— | —Ph |
| 1.086 | —cyclopropyl | —Me | —(C=O)ⁱPr | 6-F | 3-Cl | —CH₂—CH₂— | —Ph |
| 1.087 | —CH₂—C=CH—Me | —Me | —(C=O)ⁱPr | 6-Cl | 3-Cl | —CH₂—CH₂— | —Ph |
| 1.088 | —cyclopropyl | —Me | —(C=O)ⁱPr | 6-Cl | 3-Cl | —CH₂—CH₂— | —Ph |
| 1.089 | —Me | —Me | —(C=O)ⁱPr | 6-F | 3-Cl | —CH₂—CH₂— | 4-chloro-phenyl- |
| 1.090 | —CH₂—C=CH—Me | —Me | —(C=O)ⁱPr | 6-F | 3-Cl | —CH₂—CH₂— | 4-chloro-phenyl- |
| 1.091 | —cyclopropyl | —Me | —(C=O)ⁱPr | 6-F | 3-Cl | —CH₂—CH₂— | 4-chloro-phenyl- |
| 1.092 | —Me | —Me | —(C=O)ⁱPr | 6-Cl | 3-Cl | —CH₂—CH₂— | 4-chloro-phenyl- |
| 1.093 | —CH₂—C=CH—Me | —Me | —(C=O)ⁱPr | 6-Cl | 3-Cl | —CH₂—CH₂— | 4-chloro-phenyl- |
| 1.094 | —cyclopropyl | —Me | —(C=O)ⁱPr | 6-Cl | 3-Cl | —CH₂—CH₂— | 4-chloro-phenyl- |
| 1.095 | —Me | —Me | —(C=O)ⁱPr | 6-F | 3-Cl | —CH₂—CH₂— | 4-trifluoromethyl-phenyl- |
| 1.096 | —CH₂—C=CH—Me | —Me | —(C=O)ⁱPr | 6-F | 3-Cl | —CH₂—CH₂— | 4-trifluoromethyl-phenyl- |
| 1.097 | —cyclopropyl | —Me | —(C=O)ⁱPr | 6-F | 3-Cl | —CH₂—CH₂— | 4-trifluoromethyl-phenyl- |
| 1.098 | —Me | —Me | —(C=O)ⁱPr | 6-Cl | 3-Cl | —CH₂—CH₂— | 4-trifluoromethyl-phenyl- |
| 1.099 | —CH₂—C=CH—Me | —Me | —(C=O)ⁱPr | 6-Cl | 3-Cl | —CH₂—CH₂— | 4-trifluoromethyl-phenyl- |

TABLE 1-continued

Herbicidal compounds of formula (I) for use as (A) in the present invention. The numbering system used to describe the positions of X and Y is shown for the purposes of clarity only.

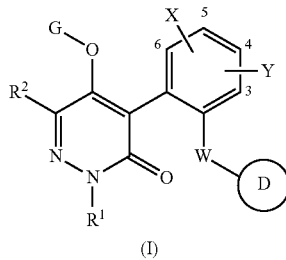

(I)

| Compound No. | R¹ | R² | G | X | Y | W | D |
|---|---|---|---|---|---|---|---|
| 1.100 | —cyclopropyl | —Me | —(C=O)ⁱPr | 6-Cl | 3-Cl | —CH₂—CH₂— | 4-trifluoromethyl-phenyl- |
| 1.101 | —Me | —Me | —(C=O)ⁱPr | 6-F | 3-Cl | —CH₂—CH₂— | 4-cyano-phenyl- |
| 1.102 | —CH₂—C=CH | —Me | —(C=O)ⁱPr | 6-F | 3-Cl | —CH₂—CH₂— | 4-cyano-phenyl- |
| 1.103 | —cyclopropyl | —Me | —(C=O)ⁱPr | 6-F | 3-Cl | —CH₂—CH₂— | 4-cyano-phenyl- |
| 1.104 | —Me | —Me | —(C=O)ⁱPr | 6-Cl | 3-Cl | —CH₂—CH₂— | 4-cyano-phenyl- |
| 1.105 | —CH₂—C=CH | —Me | —(C=O)ⁱPr | 6-Cl | 3-Cl | —CH₂—CH₂— | 4-cyano-phenyl- |
| 1.106 | —cyclopropyl | —Me | —(C=O)ⁱPr | 6-Cl | 3-Cl | —CH₂—CH₂— | 4-cyano-phenyl- |
| 1.107 | —Me | —Me | —(C=O)ⁱPr | 6-F | 3-Cl | —CH₂—CH₂— | 4-chloro-3-pyridyl- |
| 1.108 | —CH₂—C=CH | —Me | —(C=O)ⁱPr | 6-F | 3-Cl | —CH₂—CH₂— | 4-chloro-3-pyridyl- |
| 1.109 | —cyclopropyl | —Me | —(C=O)ⁱPr | 6-F | 3-Cl | —CH₂—CH₂— | 4-chloro-3-pyridyl- |
| 1.110 | —Me | —Me | —(C=O)ⁱPr | 6-Cl | 3-Cl | —CH₂—CH₂— | 4-chloro-3-pyridyl- |
| 1.111 | —CH₂—C=CH | —Me | —(C=O)ⁱPr | 6-Cl | 3-Cl | —CH₂—CH₂— | 4-chloro-3-pyridyl- |
| 1.112 | —cyclopropyl | —Me | —(C=O)ⁱPr | 6-Cl | 3-Cl | —CH₂—CH₂— | 4-chloro-3-pyridyl- |
| 1.113 | —Me | —Me | —(C=O)ⁱPr | 6-F | 3-Cl | —CH₂—CH₂— | 2-chlorothiazol-5-yl- |
| 1.114 | —CH₂—C=CH | —Me | —(C=O)ⁱPr | 6-F | 3-Cl | —CH₂—CH₂— | 2-chlorothiazol-5-yl- |
| 1.115 | —cyclopropyl | —Me | —(C=O)ⁱPr | 6-F | 3-Cl | —CH₂—CH₂— | 2-chlorothiazol-5-yl- |
| 1.116 | —Me | —Me | —(C=O)ⁱPr | 6-Cl | 3-Cl | —CH₂—CH₂— | 2-chlorothiazol-5-yl- |
| 1.117 | —CH₂—C=CH | —Me | —(C=O)ⁱPr | 6-Cl | 3-Cl | —CH₂—CH₂— | 2-chlorothiazol-5-yl- |
| 1.118 | —cyclopropyl | —Me | —(C=O)ⁱPr | 6-Cl | 3-Cl | —CH₂—CH₂— | 2-chlorothiazol-5-yl- |
| 1.119 | —Me | —Me | —(C=O)ⁱPr | 6-F | 3-Cl | —CH₂—CH₂— | 4-trifluoromethy1-3-pyridyl- |
| 1.120 | —CH₂—C=CH | —Me | —(C=O)ⁱPr | 6-F | 3-Cl | —CH₂—CH₂— | 4-trifluoromethy1-3-pyridyl- |
| 1.121 | —cyclopropyl | —Me | —(C=O)ⁱPr | 6-F | 3-Cl | —CH₂—CH₂— | 4-trifluoromethy1-3-pyridyl- |
| 1.122 | —Me | —Me | —(C=O)ⁱPr | 6-Cl | 3-Cl | —CH₂—CH₂— | 4-trifluoromethy1-3-pyridyl- |
| 1.123 | —CH₂—C=CH | —Me | —(C=O)ⁱPr | 6-Cl | 3-Cl | —CH₂—CH₂— | 4-trifluoromethy1-3-pyridyl- |
| 1.124 | —cyclopropyl | —Me | —(C=O)ⁱPr | 6-Cl | 3-Cl | —CH₂—CH₂— | 4-trifluoromethy1-3-pyridyl- |
| 1.125 | —Me | —Me | —(C=O)ⁱPr | 6-F | 3-Cl | —CH₂—CH₂— | 4-fluoro-phenyl- |
| 1.126 | —CH₂—C=CH | —Me | —(C=O)ⁱPr | 6-F | 3-Cl | —CH₂—CH₂— | 4-fluoro-phenyl- |
| 1.127 | —cyclopropyl | —Me | —(C=O)ⁱPr | 6-F | 3-Cl | —CH₂—CH₂— | 4-fluoro-phenyl- |
| 1.128 | —Me | —Me | —(C=O)ⁱPr | 6-Cl | 3-Cl | —CH₂—CH₂— | 4-fluoro-phenyl- |
| 1.129 | —CH₂—C=CH | —Me | —(C=O)ⁱPr | 6-Cl | 3-Cl | —CH₂—CH₂— | 4-fluoro-phenyl- |
| 1.130 | —cyclopropyl | —Me | —(C=O)ⁱPr | 6-Cl | 3-Cl | —CH₂—CH₂— | 4-fluoro-phenyl- |
| 1.131 | —Me | —Me | —(C=O)ⁱPr | 6-F | 3-Cl | —CH₂—CH₂— | 3-pyridyl- |
| 1.132 | —CH₂—C=CH | —Me | —(C=O)ⁱPr | 6-F | 3-Cl | —CH₂—CH₂— | 3-pyridyl- |
| 1.133 | —cyclopropyl | —Me | —(C=O)ⁱPr | 6-F | 3-Cl | —CH₂—CH₂— | 3-pyridyl- |
| 1.134 | —Me | —Me | —(C=O)ⁱPr | 6-Cl | 3-Cl | —CH₂—CH₂— | 3-pyridyl- |
| 1.135 | —CH₂—C=CH | —Me | —(C=O)ⁱPr | 6-Cl | 3-Cl | —CH₂—CH₂— | 3-pyridyl- |
| 1.136 | —cyclopropyl | —Me | —(C=O)ⁱPr | 6-Cl | 3-Cl | —CH₂—CH₂— | 3-pyridyl- |
| 1.137 | —Me | —Me | —(C=O)ⁱPr | 6-F | 3-Cl | —CH₂—CH₂— | 3,4-difluoro-phenyl- |
| 1.138 | —CH₂—C=CH | —Me | —(C=O)ⁱPr | 6-F | 3-Cl | —CH₂—CH₂— | 3,4-difluoro-phenyl- |
| 1.139 | —cyclopropyl | —Me | —(C=O)ⁱPr | 6-F | 3-Cl | —CH₂—CH₂— | 3,4-difluoro-phenyl- |
| 1.140 | —Me | —Me | —(C=O)ⁱPr | 6-Cl | 3-Cl | —CH₂—CH₂— | 3,4-difluoro-phenyl- |
| 1.141 | —CH₂—C=CH | —Me | —(C=O)ⁱPr | 6-Cl | 3-Cl | —CH₂—CH₂— | 3,4-difluoro-phenyl- |
| 1.142 | —cyclopropyl | —Me | —(C=O)ⁱPr | 6-Cl | 3-Cl | —CH₂—CH₂— | 3,4-difluoro-phenyl- |
| 1.143 | —Me | —Me | —(C=O)ⁱPr | 6-F | 3-Cl | —CH₂—CH₂— | 2-trifluoromethyl-phenyl- |
| 1.144 | —CH₂—C=CH | —Me | —(C=O)ⁱPr | 6-F | 3-Cl | —CH₂—CH₂— | 2-trifluoromethyl-phenyl- |
| 1.145 | —cyclopropyl | —Me | —(C=O)ⁱPr | 6-F | 3-Cl | —CH₂—CH₂— | 2-trifluoromethyl-phenyl- |
| 1.146 | —Me | —Me | —(C=O)ⁱPr | 6-Cl | 3-Cl | —CH₂—CH₂— | 2-trifluoromethyl-phenyl- |
| 1.147 | —CH₂—C=CH | —Me | —(C=O)ⁱPr | 6-Cl | 3-Cl | —CH₂—CH₂— | 2-trifluoromethyl-phenyl- |
| 1.148 | —cyclopropyl | —Me | —(C=O)ⁱPr | 6-Cl | 3-Cl | —CH₂—CH₂— | 2-trifluoromethyl-phenyl- |
| 1.149 | —Me | —Me | —(C=O)ⁱPr | 6-F | 3-Cl | —CH₂—CH₂— | 4-tolyl- |
| 1.150 | —CH₂—C=CH | —Me | —(C=O)ⁱPr | 6-F | 3-Cl | —CH₂—CH₂— | 4-tolyl- |
| 1.151 | —cyclopropyl | —Me | —(C=O)ⁱPr | 6-F | 3-Cl | —CH₂—CH₂— | 4-tolyl- |
| 1.152 | —Me | —Me | —(C=O)ⁱPr | 6-Cl | 3-Cl | —CH₂—CH₂— | 4-tolyl- |
| 1.153 | —CH₂—C=CH | —Me | —(C=O)ⁱPr | 6-Cl | 3-Cl | —CH₂—CH₂— | 4-tolyl- |
| 1.154 | —cyclopropyl | —Me | —(C=O)ⁱPr | 6-Cl | 3-Cl | —CH₂—CH₂— | 4-tolyl- |
| 1.155 | —Me | —Me | —H | 6-F | —H | —CH₂—CH₂— | —Ph |

TABLE 1-continued

Herbicidal compounds of formula (I) for use as (A) in the present invention. The numbering system used to describe the positions of X and Y is shown for the purposes of clarity only.

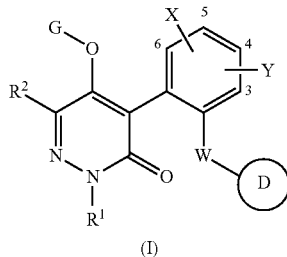

(I)

| Compound No. | $R^1$ | $R^2$ | G | X | Y | W | D |
|---|---|---|---|---|---|---|---|
| 1.156 | —Me | —Me | —H | 6-F | —H | (E) —CH=CH— | —Ph |
| 1.157 | —Me | —Me | —H | 6-F | —H | trans (cyclopropyl) | —Ph |
| 1.158 | —Me | —Me | —H | 6-F | —H | cis (cyclopropyl) | —Ph |
| 1.159 | —Me | —Me | —H | 6-Cl | —H | —CH$_2$—CH$_2$— | —Ph |
| 1.160 | —Me | —Me | —H | 6-Cl | —H | trans (cyclopropyl) | —Ph |
| 1.161 | —Me | —Me | —H | 6-Cl | —H | cis (cyclopropyl) | —Ph |
| 1.162 | —CH$_2$—C≡CH | —Me | —H | 6-F | —H | —CH$_2$—CH$_2$— | —Ph |
| 1.163 | —cyclopropyl | —Me | —H | 6-F | —H | —CH$_2$—CH$_2$— | —Ph |
| 1.164 | —CH$_2$—C≡CH | —Me | —H | 6-Cl | —H | —CH$_2$—CH$_2$— | —Ph |
| 1.165 | —cyclopropyl | —Me | —H | 6-Cl | —H | —CH$_2$—CH$_2$— | —Ph |
| 1.166 | —Me | —Me | —H | 6-F | —H | —CH$_2$—CH$_2$— | 4-chloro-phenyl- |
| 1.167 | —CH$_2$—C≡CH | —Me | —H | 6-F | —H | —CH$_2$—CH$_2$— | 4-chloro-phenyl- |
| 1.168 | —cyclopropyl | —Me | —H | 6-F | —H | —CH$_2$—CH$_2$— | 4-chloro-phenyl- |
| 1.169 | —Me | —Me | —H | 6-Cl | —H | —CH$_2$—CH$_2$— | 4-chloro-phenyl- |
| 1.170 | —CH$_2$—C≡CH | —Me | —H | 6-Cl | —H | —CH$_2$—CH$_2$— | 4-chloro-phenyl- |
| 1.171 | —cyclopropyl | —Me | —H | 6-Cl | —H | —CH$_2$—CH$_2$— | 4-chloro-phenyl- |
| 1.172 | —Me | —Me | —H | 6-F | —H | —CH$_2$—CH$_2$— | 4-trifluoromethyl-phenyl- |
| 1.173 | —CH$_2$—C≡CH | —Me | —H | 6-F | —H | —CH$_2$—CH$_2$— | 4-trifluoromethyl-phenyl- |
| 1.174 | —cyclopropyl | —Me | —H | 6-F | —H | —CH$_2$—CH$_2$— | 4-trifluoromethyl-phenyl- |
| 1.175 | —Me | —Me | —H | 6-Cl | —H | —CH$_2$—CH$_2$— | 4-trifluoromethyl-phenyl- |
| 1.176 | —CH$_2$—C≡CH | —Me | —H | 6-Cl | —H | —CH$_2$—CH$_2$— | 4-trifluoromethyl-phenyl- |
| 1.177 | —cyclopropyl | —Me | —H | 6-Cl | —H | —CH$_2$—CH$_2$— | 4-trifluoromethyl-phenyl- |

TABLE 1-continued

Herbicidal compounds of formula (I) for use as (A) in the present invention. The numbering system used to describe the positions of X and Y is shown for the purposes of clarity only.

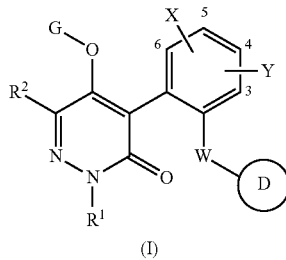

(I)

| Compound No. | R¹ | R² | G | X | Y | W | D |
|---|---|---|---|---|---|---|---|
| 1.178 | —Me | —Me | —H | 6-F | —H | —CH₂—CH₂— | 4-cyano-phenyl- |
| 1.179 | —CH₂—C≡CH | —Me | —H | 6-F | —H | —CH₂—CH₂— | 4-cyano-phenyl- |
| 1.180 | —cyclopropyl | —Me | —H | 6-F | —H | —CH₂—CH₂— | 4-cyano-phenyl- |
| 1.181 | —Me | —Me | —H | 6-Cl | —H | —CH₂—CH₂— | 4-cyano-phenyl- |
| 1.182 | —CH₂—C≡CH | —Me | —H | 6-Cl | —H | —CH₂—CH₂— | 4-cyano-phenyl- |
| 1.183 | —cyclopropyl | —Me | —H | 6-Cl | —H | —CH₂—CH₂— | 4-cyano-phenyl- |
| 1.184 | —Me | —Me | —H | 6-F | —H | —CH₂—CH₂— | 4-chloro-3-pyridyl- |
| 1.185 | —CH₂—C≡CH | —Me | —H | 6-F | —H | —CH₂—CH₂— | 4-chloro-3-pyridyl- |
| 1.186 | —cyclopropyl | —Me | —H | 6-F | —H | —CH₂—CH₂— | 4-chloro-3-pyridyl- |
| 1.187 | —Me | —Me | —H | 6-Cl | —H | —CH₂—CH₂— | 4-chloro-3-pyridyl- |
| 1.188 | —CH₂—C≡CH | —Me | —H | 6-Cl | —H | —CH₂—CH₂— | 4-chloro-3-pyridyl- |
| 1.189 | —cyclopropyl | —Me | —H | 6-Cl | —H | —CH₂—CH₂— | 4-chloro-3-pyridyl- |
| 1.190 | —Me | —Me | —H | 6-F | —H | —CH₂—CH₂— | 2-chlorothiazol-5-yl- |
| 1.191 | —CH₂—C≡CH | —Me | —H | 6-F | —H | —CH₂—CH₂— | 2-chlorothiazol-5-yl- |
| 1.192 | —cyclopropyl | —Me | —H | 6-F | —H | —CH₂—CH₂— | 2-chlorothiazol-5-yl- |
| 1.193 | —Me | —Me | —H | 6-Cl | —H | —CH₂—CH₂— | 2-chlorothiazol-5-yl- |
| 1.194 | —CH₂—C≡CH | —Me | —H | 6-Cl | —H | —CH₂—CH₂— | 2-chlorothiazol-5-yl- |
| 1.195 | —cyclopropyl | —Me | —H | 6-Cl | —H | —CH₂—CH₂— | 2-chlorothiazol-5-yl- |
| 1.196 | —Me | —Me | —H | 6-F | —H | —CH₂—CH₂— | 4-trifluoromethy1-3-pyridyl- |
| 1.197 | —CH₂—C≡CH | —Me | —H | 6-F | —H | —CH₂—CH₂— | 4-trifluoromethy1-3-pyridyl- |
| 1.198 | —cyclopropyl | —Me | —H | 6-F | —H | —CH₂—CH₂— | 4-trifluoromethy1-3-pyridyl- |
| 1.199 | —Me | —Me | —H | 6-Cl | —H | —CH₂—CH₂— | 4-trifluoromethy1-3-pyridyl- |
| 1.200 | —CH₂—C≡CH | —Me | —H | 6-Cl | —H | —CH₂—CH₂— | 4-trifluoromethy1-3-pyridyl- |
| 1.201 | —cyclopropyl | —Me | —H | 6-Cl | —H | —CH₂—CH₂— | 4-trifluoromethy1-3-pyridyl- |
| 1.202 | —Me | —Me | —H | 6-F | —H | —CH₂—CH₂— | 4-fluoro-phenyl- |
| 1.203 | —CH₂—C≡CH | —Me | —H | 6-F | —H | —CH₂—CH₂— | 4-fluoro-phenyl- |
| 1.204 | —cyclopropyl | —Me | —H | 6-F | —H | —CH₂—CH₂— | 4-fluoro-phenyl- |
| 1.205 | —Me | —Me | —H | 6-Cl | —H | —CH₂—CH₂— | 4-fluoro-phenyl- |
| 1.206 | —CH₂—C≡CH | —Me | —H | 6-Cl | —H | —CH₂—CH₂— | 4-fluoro-phenyl- |
| 1.207 | —cyclopropyl | —Me | —H | 6-Cl | —H | —CH₂—CH₂— | 4-fluoro-phenyl- |
| 1.208 | —Me | —Me | —H | 6-F | —H | —CH₂—CH₂— | 3-pyridyl- |
| 1.209 | —CH₂—C≡CH | —Me | —H | 6-F | —H | —CH₂—CH₂— | 3-pyridyl- |
| 1.210 | —cyclopropyl | —Me | —H | 6-F | —H | —CH₂—CH₂— | 3-pyridyl- |
| 1.211 | —Me | —Me | —H | 6-Cl | —H | —CH₂—CH₂— | 3-pyridyl- |
| 1.212 | —CH₂—C≡CH | —Me | —H | 6-Cl | —H | —CH₂—CH₂— | 3-pyridyl- |
| 1.213 | —cyclopropyl | —Me | —H | 6-Cl | —H | —CH₂—CH₂— | 3-pyridyl- |
| 1.214 | —Me | —Me | —H | 6-F | —H | —CH₂—CH₂— | 3,4-difluoro-phenyl- |
| 1.215 | —CH₂—C≡CH | —Me | —H | 6-F | —H | —CH₂—CH₂— | 3,4-difluoro-phenyl- |
| 1.216 | —cyclopropyl | —Me | —H | 6-F | —H | —CH₂—CH₂— | 3,4-difluoro-phenyl- |
| 1.217 | —Me | —Me | —H | 6-Cl | —H | —CH₂—CH₂— | 3,4-difluoro-phenyl- |
| 1.218 | —CH₂—C≡CH | —Me | —H | 6-Cl | —H | —CH₂—CH₂— | 3,4-difluoro-phenyl- |
| 1.219 | —cyclopropyl | —Me | —H | 6-Cl | —H | —CH₂—CH₂— | 3,4-difluoro-phenyl- |
| 1.220 | —Me | —Me | —H | 6-F | —H | —CH₂—CH₂— | 2-trifluoromethyl-phenyl- |
| 1.221 | —CH₂—C≡CH | —Me | —H | 6-F | —H | —CH₂—CH₂— | 2-trifluoromethyl-phenyl- |
| 1.222 | —cyclopropyl | —Me | —H | 6-F | —H | —CH₂—CH₂— | 2-trifluoromethyl-phenyl- |
| 1.223 | —Me | —Me | —H | 6-Cl | —H | —CH₂—CH₂— | 2-trifluoromethyl-phenyl- |
| 1.224 | —CH₂—C≡CH | —Me | —H | 6-Cl | —H | —CH₂—CH₂— | 2-trifluoromethyl-phenyl- |
| 1.225 | —cyclopropyl | —Me | —H | 6-Cl | —H | —CH₂—CH₂— | 2-trifluoromethyl-phenyl- |
| 1.226 | —Me | —Me | —H | 6-F | —H | —CH₂—CH₂— | 4-tolyl- |
| 1.227 | —CH₂—C≡CH | —Me | —H | 6-F | —H | —CH₂—CH₂— | 4-tolyl- |
| 1.228 | —cyclopropyl | —Me | —H | 6-F | —H | —CH₂—CH₂— | 4-tolyl- |
| 1.229 | —Me | —Me | —H | 6-Cl | —H | —CH₂—CH₂— | 4-tolyl- |
| 1.230 | —CH₂—C≡CH | —Me | —H | 6-Cl | —H | —CH₂—CH₂— | 4-tolyl- |
| 1.231 | —cyclopropyl | —Me | —H | 6-Cl | —H | —CH₂—CH₂— | 4-tolyl- |
| 1.232 | —Me | —Me | —(C=O)ⁱPr | 6-F | —H | —CH₂—CH₂— | —Ph |

TABLE 1-continued

Herbicidal compounds of formula (I) for use as (A) in the present invention. The numbering system used to describe the positions of X and Y is shown for the purposes of clarity only.

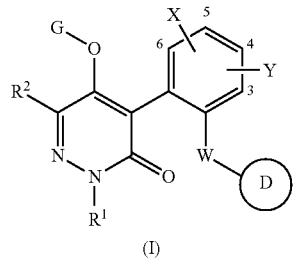

(I)

| Compound No. | R¹ | R² | G | X | Y | W | D |
|---|---|---|---|---|---|---|---|
| 1.233 | —Me | —Me | —(C=O)ⁱPr | 6-F | —H | (E) —CH=CH— | —Ph |
| 1.234 | —Me | —Me | —(C=O)ⁱPr | 6-F | —H | trans cyclopropyl | —Ph |
| 1.235 | —Me | —Me | —(C=O)ⁱPr | 6-F | —H | cis cyclopropyl | —Ph |
| 1.236 | —Me | —Me | —(C=O)ⁱPr | 6-Cl | —H | —CH₂—CH₂— | —Ph |
| 1.237 | —Me | —Me | —(C=O)ⁱPr | 6-Cl | —H | trans cyclopropyl | —Ph |
| 1.238 | —Me | —Me | —(C=O)ⁱPr | 6-Cl | —H | cis cyclopropyl | —Ph |
| 1.239 | —CH₂—C≡CH—Me | —Me | —(C=O)ⁱPr | 6-F | —H | —CH₂—CH₂— | —Ph |
| 1.240 | —cyclopropyl | —Me | —(C=O)ⁱPr | 6-F | —H | —CH₂—CH₂— | —Ph |
| 1.241 | —CH₂—C≡CH—Me | —Me | —(C=O)ⁱPr | 6-Cl | —H | —CH₂—CH₂— | —Ph |
| 1.242 | —cyclopropyl | —Me | —(C=O)ⁱPr | 6-Cl | —H | —CH₂—CH₂— | —Ph |
| 1.243 | —Me | —Me | —(C=O)ⁱPr | 6-F | —H | —CH₂—CH₂— | 4-chloro-phenyl- |
| 1.244 | —CH₂—C≡CH—Me | —Me | —(C=O)ⁱPr | 6-F | —H | —CH₂—CH₂— | 4-chloro-phenyl- |
| 1.245 | —cyclopropyl | —Me | —(C=O)ⁱPr | 6-F | —H | —CH₂—CH₂— | 4-chloro-phenyl- |
| 1.246 | —Me | —Me | —(C=O)ⁱPr | 6-Cl | —H | —CH₂—CH₂— | 4-chloro-phenyl- |
| 1.247 | —CH₂—C≡CH—Me | —Me | —(C=O)ⁱPr | 6-Cl | —H | —CH₂—CH₂— | 4-chloro-phenyl- |
| 1.248 | —cyclopropyl | —Me | —(C=O)ⁱPr | 6-Cl | —H | —CH₂—CH₂— | 4-chloro-phenyl- |
| 1.249 | —Me | —Me | —(C=O)ⁱPr | 6-F | —H | —CH₂—CH₂— | 4-trifluoromethyl-phenyl- |
| 1.250 | —CH₂—C≡CH—Me | —Me | —(C=O)ⁱPr | 6-F | —H | —CH₂—CH₂— | 4-trifluoromethyl-phenyl- |
| 1.251 | —cyclopropyl | —Me | —(C=O)ⁱPr | 6-F | —H | —CH₂—CH₂— | 4-trifluoromethyl-phenyl- |
| 1.252 | —Me | —Me | —(C=O)ⁱPr | 6-Cl | —H | —CH₂—CH₂— | 4-trifluoromethyl-phenyl- |
| 1.253 | —CH₂—C≡CH—Me | —Me | —(C=O)ⁱPr | 6-Cl | —H | —CH₂—CH₂— | 4-trifluoromethyl-phenyl- |

TABLE 1-continued

Herbicidal compounds of formula (I) for use as (A) in the present invention. The numbering system used to describe the positions of X and Y is shown for the purposes of clarity only.

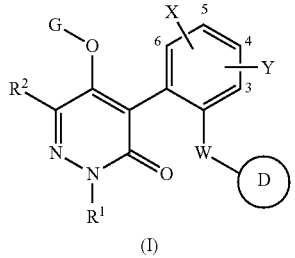

(I)

| Compound No. | R$^1$ | R$^2$ | G | X | Y | W | D |
|---|---|---|---|---|---|---|---|
| 1.254 | —cyclopropyl | —Me | —(C=O)$^i$Pr | 6-Cl | —H | —CH$_2$—CH$_2$— | 4-trifluoromethyl-phenyl- |
| 1.255 | —Me | —Me | —(C=O)$^i$Pr | 6-F | —H | —CH$_2$—CH$_2$— | 4-cyano-phenyl- |
| 1.256 | —CH$_2$—C=CH | —Me | —(C=O)$^i$Pr | 6-F | —H | —CH$_2$—CH$_2$— | 4-cyano-phenyl- |
| 1.257 | —cyclopropyl | —Me | —(C=O)$^i$Pr | 6-F | —H | —CH$_2$—CH$_2$— | 4-cyano-phenyl- |
| 1.258 | —Me | —Me | —(C=O)$^i$Pr | 6-Cl | —H | —CH$_2$—CH$_2$— | 4-cyano-phenyl- |
| 1.259 | —CH$_2$—C=CH | —Me | —(C=O)$^i$Pr | 6-Cl | —H | —CH$_2$—CH$_2$— | 4-cyano-phenyl- |
| 1.260 | —cyclopropyl | —Me | —(C=O)$^i$Pr | 6-Cl | —H | —CH$_2$—CH$_2$— | 4-cyano-phenyl- |
| 1.261 | —Me | —Me | —(C=O)$^i$Pr | 6-F | —H | —CH$_2$—CH$_2$— | 4-chloro-3-pyridyl- |
| 1.262 | —CH$_2$—C=CH | —Me | —(C=O)$^i$Pr | 6-F | —H | —CH$_2$—CH$_2$— | 4-chloro-3-pyridyl- |
| 1.263 | —cyclopropyl | —Me | —(C=O)$^i$Pr | 6-F | —H | —CH$_2$—CH$_2$— | 4-chloro-3-pyridyl- |
| 1.264 | —Me | —Me | —(C=O)$^i$Pr | 6-Cl | —H | —CH$_2$—CH$_2$— | 4-chloro-3-pyridyl- |
| 1.265 | —CH$_2$—C=CH | —Me | —(C=O)$^i$Pr | 6-Cl | —H | —CH$_2$—CH$_2$— | 4-chloro-3-pyridyl- |
| 1.266 | —cyclopropyl | —Me | —(C=O)$^i$Pr | 6-Cl | —H | —CH$_2$—CH$_2$— | 4-chloro-3-pyridyl- |
| 1.267 | —Me | —Me | —(C=O)$^i$Pr | 6-F | —H | —CH$_2$—CH$_2$— | 2-chlorothiazol-5-yl- |
| 1.268 | —CH$_2$—C=CH | —Me | —(C=O)$^i$Pr | 6-F | —H | —CH$_2$—CH$_2$— | 2-chlorothiazol-5-yl- |
| 1.269 | —cyclopropyl | —Me | —(C=O)$^i$Pr | 6-F | —H | —CH$_2$—CH$_2$— | 2-chlorothiazol-5-yl- |
| 1.270 | —Me | —Me | —(C=O)$^i$Pr | 6-Cl | —H | —CH$_2$—CH$_2$— | 2-chlorothiazol-5-yl- |
| 1.271 | —CH$_2$—C=CH | —Me | —(C=O)$^i$Pr | 6-Cl | —H | —CH$_2$—CH$_2$— | 2-chlorothiazol-5-yl- |
| 1.272 | —cyclopropyl | —Me | —(C=O)$^i$Pr | 6-Cl | —H | —CH$_2$—CH$_2$— | 2-chlorothiazol-5-yl- |
| 1.273 | —Me | —Me | —(C=O)$^i$Pr | 6-F | —H | —CH$_2$—CH$_2$— | 4-trifluoromethyl-3-pyridyl- |
| 1.274 | —CH$_2$—C=CH | —Me | —(C=O)$^i$Pr | 6-F | —H | —CH$_2$—CH$_2$— | 4-trifluoromethyl-3-pyridyl- |
| 1.275 | —cyclopropyl | —Me | —(C=O)$^i$Pr | 6-F | —H | —CH$_2$—CH$_2$— | 4-trifluoromethyl-3-pyridyl- |
| 1.276 | —Me | —Me | —(C=O)$^i$Pr | 6-Cl | —H | —CH$_2$—CH$_2$— | 4-trifluoromethyl-3-pyridyl- |
| 1.277 | —CH$_2$—C=CH | —Me | —(C=O)$^i$Pr | 6-Cl | —H | —CH$_2$—CH$_2$— | 4-trifluoromethyl-3-pyridyl- |
| 1.278 | —cyclopropyl | —Me | —(C=O)$^i$Pr | 6-Cl | —H | —CH$_2$—CH$_2$— | 4-trifluoromethyl-3-pyridyl- |
| 1.279 | —Me | —Me | —(C=O)$^i$Pr | 6-F | —H | —CH$_2$—CH$_2$— | 4-fluoro-phenyl- |
| 1.280 | —CH$_2$—C=CH | —Me | —(C=O)$^i$Pr | 6-F | —H | —CH$_2$—CH$_2$— | 4-fluoro-phenyl- |
| 1.281 | —cyclopropyl | —Me | —(C=O)$^i$Pr | 6-F | —H | —CH$_2$—CH$_2$— | 4-fluoro-phenyl- |
| 1.282 | —Me | —Me | —(C=O)$^i$Pr | 6-Cl | —H | —CH$_2$—CH$_2$— | 4-fluoro-phenyl- |
| 1.283 | —CH$_2$—C=CH | —Me | —(C=O)$^i$Pr | 6-Cl | —H | —CH$_2$—CH$_2$— | 4-fluoro-phenyl- |
| 1.284 | —cyclopropyl | —Me | —(C=O)$^i$Pr | 6-Cl | —H | —CH$_2$—CH$_2$— | 4-fluoro-phenyl- |
| 1.285 | —Me | —Me | —(C=O)$^i$Pr | 6-F | —H | —CH$_2$—CH$_2$— | 3-pyridyl- |
| 1.286 | —CH$_2$—C=CH | —Me | —(C=O)$^i$Pr | 6-F | —H | —CH$_2$—CH$_2$— | 3-pyridyl- |
| 1.287 | —cyclopropyl | —Me | —(C=O)$^i$Pr | 6-F | —H | —CH$_2$—CH$_2$— | 3-pyridyl- |
| 1.288 | —Me | —Me | —(C=O)$^i$Pr | 6-Cl | —H | —CH$_2$—CH$_2$— | 3-pyridyl- |
| 1.289 | —CH$_2$—C=CH | —Me | —(C=O)$^i$Pr | 6-Cl | —H | —CH$_2$—CH$_2$— | 3-pyridyl- |
| 1.290 | —cyclopropyl | —Me | —(C=O)$^i$Pr | 6-Cl | —H | —CH$_2$—CH$_2$— | 3-pyridyl- |
| 1.291 | —Me | —Me | —(C=O)$^i$Pr | 6-F | —H | —CH$_2$—CH$_2$— | 3,4-difluoro-phenyl- |
| 1.292 | —CH$_2$—C=CH | —Me | —(C=O)$^i$Pr | 6-F | —H | —CH$_2$—CH$_2$— | 3,4-difluoro-phenyl- |
| 1.293 | —cyclopropyl | —Me | —(C=O)$^i$Pr | 6-F | —H | —CH$_2$—CH$_2$— | 3,4-difluoro-phenyl- |
| 1.294 | —Me | —Me | —(C=O)$^i$Pr | 6-Cl | —H | —CH$_2$—CH$_2$— | 3,4-difluoro-phenyl- |
| 1.295 | —CH$_2$—C=CH | —Me | —(C=O)$^i$Pr | 6-Cl | —H | —CH$_2$—CH$_2$— | 3,4-difluoro-phenyl- |
| 1.296 | —cyclopropyl | —Me | —(C=O)$^i$Pr | 6-Cl | —H | —CH$_2$—CH$_2$— | 3,4-difluoro-phenyl- |
| 1.297 | —Me | —Me | —(C=O)$^i$Pr | 6-F | —H | —CH$_2$—CH$_2$— | 2-trifluoromethyl-phenyl- |
| 1.298 | —CH$_2$—C=CH | —Me | —(C=O)$^i$Pr | 6-F | —H | —CH$_2$—CH$_2$— | 2-trifluoromethyl-phenyl- |
| 1.299 | —cyclopropyl | —Me | —(C=O)$^i$Pr | 6-F | —H | —CH$_2$—CH$_2$— | 2-trifluoromethyl-phenyl- |
| 1.300 | —Me | —Me | —(C=O)$^i$Pr | 6-Cl | —H | —CH$_2$—CH$_2$— | 2-trifluoromethyl-phenyl- |
| 1.301 | —CH$_2$—C=CH | —Me | —(C=O)$^i$Pr | 6-Cl | —H | —CH$_2$—CH$_2$— | 2-trifluoromethyl-phenyl- |
| 1.302 | —cyclopropyl | —Me | —(C=O)$^i$Pr | 6-Cl | —H | —CH$_2$—CH$_2$— | 2-trifluoromethyl-phenyl- |
| 1.303 | —Me | —Me | —(C=O)$^i$Pr | 6-F | —H | —CH$_2$—CH$_2$— | 4-tolyl- |
| 1.304 | —CH$_2$—C=CH | —Me | —(C=O)$^i$Pr | 6-F | —H | —CH$_2$—CH$_2$— | 4-tolyl- |
| 1.305 | —cyclopropyl | —Me | —(C=O)$^i$Pr | 6-F | —H | —CH$_2$—CH$_2$— | 4-tolyl- |
| 1.306 | —Me | —Me | —(C=O)$^i$Pr | 6-Cl | —H | —CH$_2$—CH$_2$— | 4-tolyl- |
| 1.307 | —CH$_2$—C=CH | —Me | —(C=O)$^i$Pr | 6-Cl | —H | —CH$_2$—CH$_2$— | 4-tolyl- |
| 1.308 | —cyclopropyl | —Me | —(C=O)$^i$Pr | 6-Cl | —H | —CH$_2$—CH$_2$— | 4-tolyl- |

Particularly preferred compounds of formula (I) for use in the invention are compounds 1.001, 1.002, 1.012, 1.018, 1.024, 1.042, 1.048, 1.054, 1.060, 1.066, 1.089, 1.095, 1.125, and 1.149 as described herein.

The compounds of formula (I) may be prepared according to the following schemes, in which the substituents $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, W, D, Dp, G, X, Y, Z, and m have (unless otherwise stated explicitly) the definitions described hereinbefore.

Certain compounds (I-ii) of the present invention may be prepared from compounds (2) as shown in Reaction scheme 1. Compounds (I-ii) are compounds of formula (I) in which W is —$CH_2$—$CH_2$—.

Reaction scheme 1

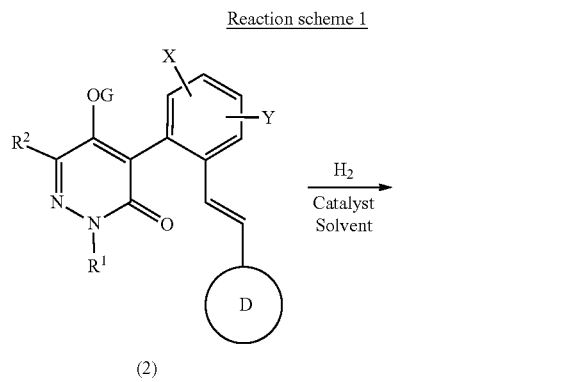

(2)

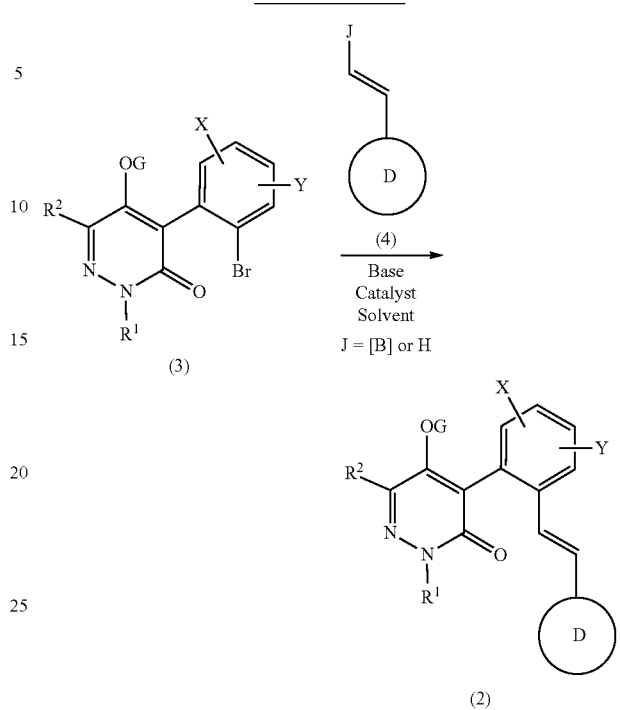

(I-ii)

Compounds (I-ii) may be prepared by catalytic hydrogenation of compounds (2) with hydrogen gas in a suitable solvent [such as tetrahydrofuran, methanol, ethanol, acetic acid or ethyl acetate] in the presence of a suitable catalyst [such as Pd/C, $Pd/CaCO_3$ or sponge nickel] at a temperature between −10 and 80° C.

Compounds (2) may be prepared from compounds (3) and compounds (4) as shown in Reaction scheme 2, according to either the Suzuki Protocol or the Heck Protocol described. When employing the Suzuki Protocol, compounds (4) are organoboron compounds such as boronic acids, boronic esters or trifluoroborate potassium salts. When employing the Heck Protocol, compounds (4) are styrenes.

Suzuki Protocol

Compounds (2) may be prepared by treatment of compounds (3) with compounds (4) in the presence of a suitable base and a suitable catalyst in a suitable solvent at a temperature between 10 and 150° C. Examples of suitable bases are potassium carbonate, potassium phosphate, sodium carbonate, sodium bicarbonate and potassium fluoride. Examples of suitable catalysts are 1,1'-bis(diphenylphosphino)ferrocene]dichloropalladium(II) dichloromethane complex [$PdCl_2$(dppf)·DCM], tetrakis(triphenylphosphine)palladium(0) [Pd(PPh$_3$)$_4$], and a catalytic system formed in-situ from a mixture of palladium (II)acetate and triphenylphosphine. Examples of suitable solvents are 1,4-dioxane, tetrahydrofuran, acetonitrile and toluene. Many compounds (4) are commercially available [such as trans-2-phenylvinylboronic acid, trans-2-(4-trifluoromethyl-phenyl)vinylboronic acid and trans-2-(4-chlorophenyl)vinylboronic acid] or can be made by known methods. Examples of compounds (3) with particular utility in the Suzuki Protocol are isobutyryl esters (3-i) wherein G is isobutyryl.

The skilled man will appreciate that the conditions of the Suzuki Protocol are liable to cleave ester groups, so that Reaction scheme 2 may also describe a reaction wherein starting material (3) contains an ester moiety [such that G is an acyl group], but product (2) does not [such that G is hydrogen].

Heck Protocol

Compounds (2) may be prepared by treatment of compounds (3) with compounds (4) in the presence of a suitable base and a suitable catalyst at a temperature between 10 and 150° C. An additional solvent may optionally be included. Examples of suitable bases are triethylamine, morpholine, N-methylmorpholine, diisopropylethylamine and pyridine. Examples of suitable catalysts are tetrakis(triphenylphosphine)palladium(0) [Pd(PPh$_3$)$_4$], a catalytic system formed in-situ from a mixture of palladium(II)acetate and triphenylphosphine, and a catalytic system formed in-situ from a mixture of tris(dibenzylideneacetone)dipalladium(0) and tri-tertbutylphosphonium tetrafluoroborate. Examples of the optional additional solvent are 1,4-dioxane, tetrahydrofuran, acetonitrile and toluene. Many compounds (4) are commercially available [such as 2-(trifluoromethyl)-5-vinyl-pyridine, 4-fluorostyrene, 4-cyanostyrene and 4-trifluoromethyl styrene] or can be made by known methods. Examples of compounds (3) with particular utility in the Heck Protocol are isobutyryl esters (3-i) wherein G is isobutyryl.

Compounds (3-i) may be prepared from compounds (5) as shown in Reaction scheme 3.

[such as dichloromethane, acetonitrile or toluene] in the presence of a suitable base [such as triethylamine, diisopropylethylamine or pyridine] at a temperature between −10 and 60° C. A catalyst [such as 4-(dimethylamino)pyridine] may optionally be included.

Compounds (5) may be prepared from compounds (6) as shown in Reaction scheme 4, by heating compounds (6) with a base (such as 1,8-diazabicyclo[5.4.0]undec-7-ene, sodium hexamethyldisilazide or lithium hexamethyldisilazide) in a solvent [such as acetonitrile, N,N-dimethylformamide or toluene] at a temperature between 50 and 200° C. Conventional heating or microwave heating may be used.

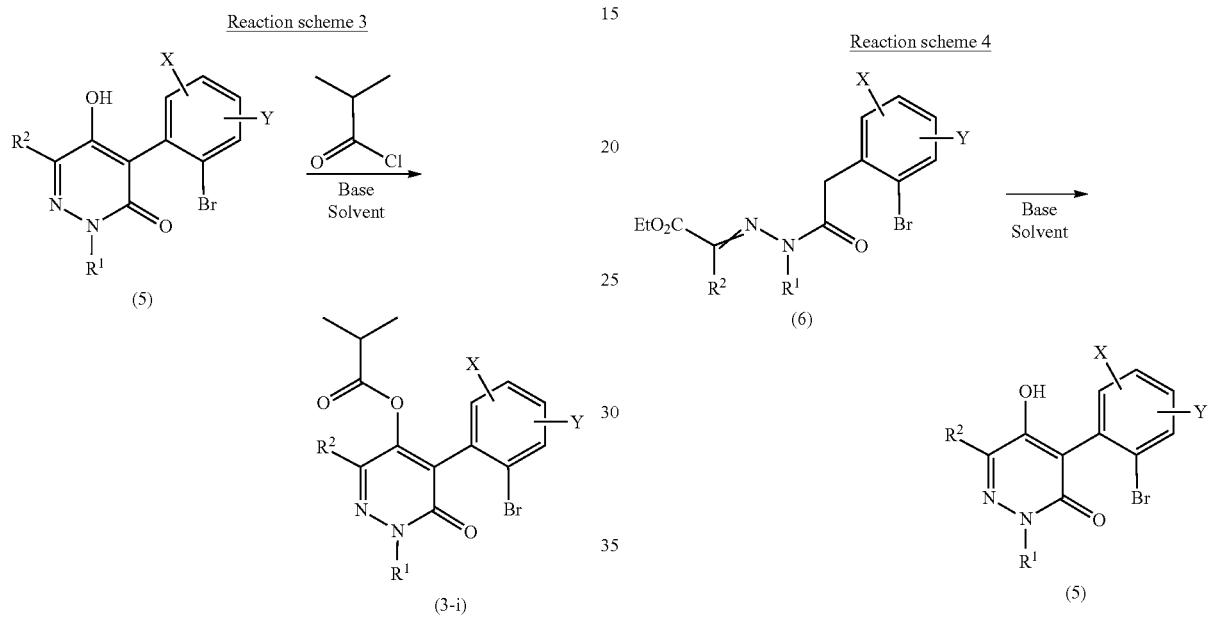

Compounds (3-i) may be prepared by treatment of compounds (5) with isobutyryl chloride in a suitable solvent Compounds (6) may be prepared from phenylacetic acids (7) as shown in Reaction scheme 5.

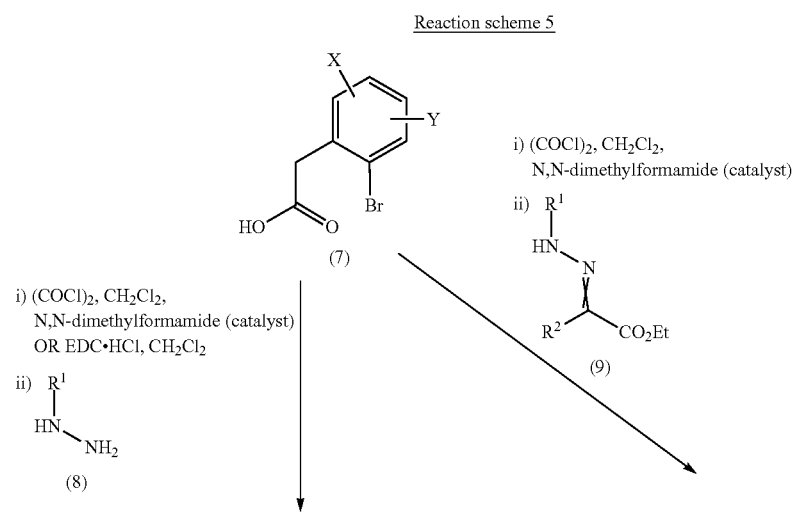

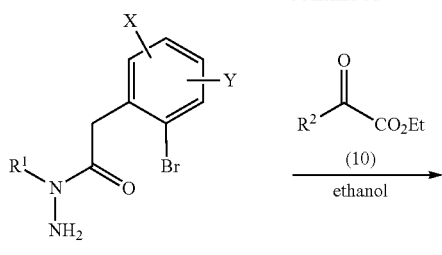 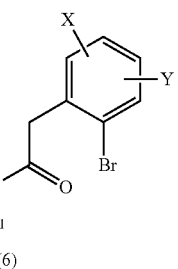

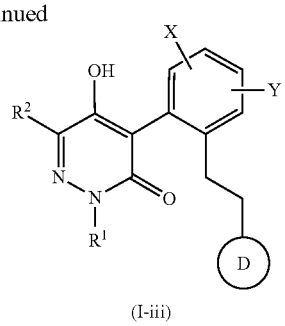

(I-iii)

With respect to Reaction scheme 5, an example of hydrazines (8) is methylhydrazine, and an example of ketoesters (10) is ethyl pyruvate. An example of hydrazones (9) is ethyl(2E/Z)-2-(methylhydrazono)propanoate, prepared according to methods described in PCT patent application WO2016/008816. An example of phenylacetic acids (7) is (2-bromo-6-fluoro-phenyl)acetic acid, which may be synthesised according to Reaction scheme 10. A further example of phenylacetic acids (7) is (2-bromo-3-chloro-6-fluoro-phenyl)acetic acid, which may be synthesised according to Reaction scheme 11.

Certain compounds (I-iii) of the present invention may be prepared from compounds (11) as shown in Reaction scheme 6 or from compounds (I-iv) as shown in Reaction scheme 12. Compounds (I-iii) are compounds of formula (I) in which W is —CH$_2$—CH$_2$— and G is hydrogen.

Reaction scheme 6

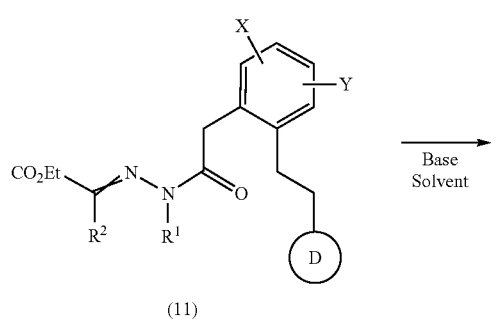

Compounds (I-iii) may be prepared by heating compounds (11) with a base (such as 1,8-diazabicyclo[5.4.0]undec-7-ene, sodium hexamethyldisilazide or lithium hexamethyldisilazide) in a solvent [such as acetonitrile, N,N-dimethylformamide or toluene] at a temperature between 50 and 200° C. Conventional heating or microwave heating may be used.

Reaction scheme 7
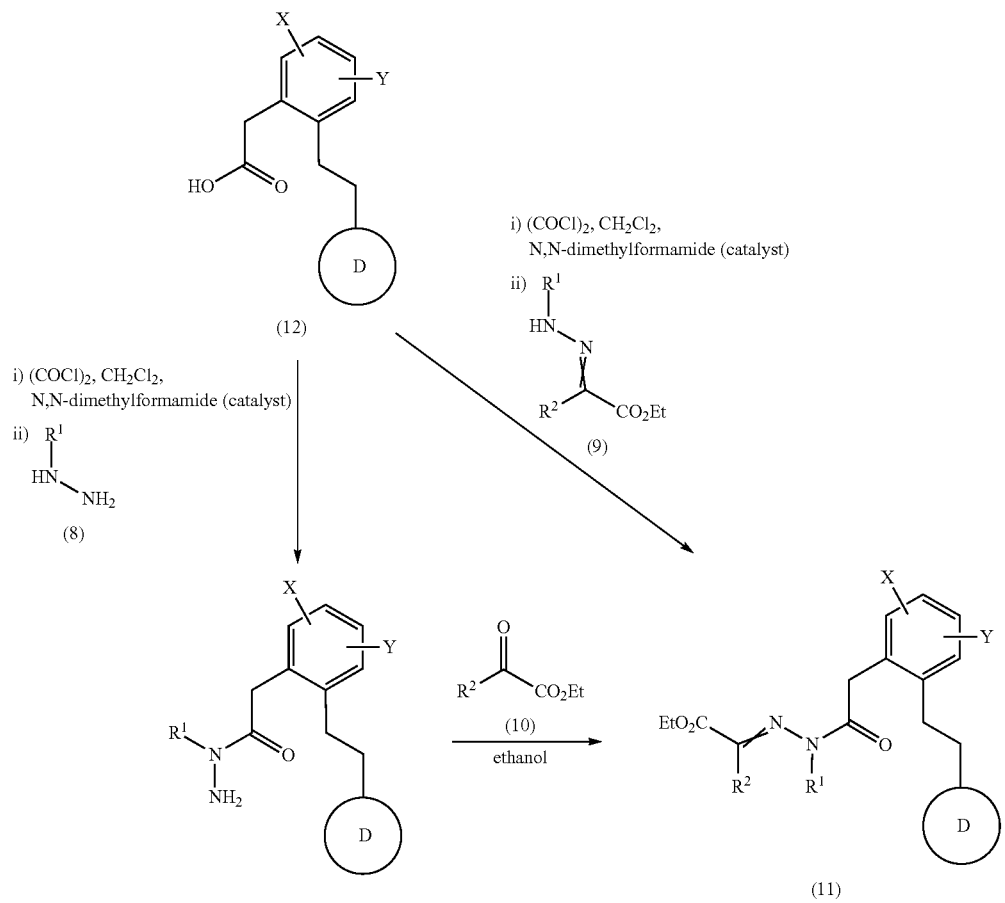
Compounds (11) may be prepared from compounds (12) as shown in Reaction scheme 7 above.
Compounds (12) can be prepared from compounds (13) as shown in Reaction scheme 8. Many compounds (13) are commercially available [such as methyl 2-phenylacetate and methyl 2-(2-fluorophenyl)acetate].
Reaction scheme 8
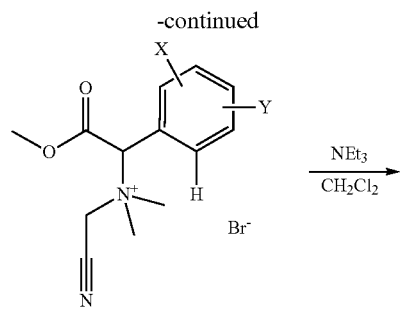
-continued
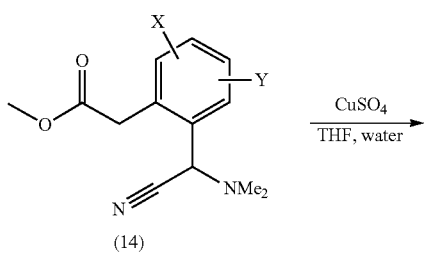

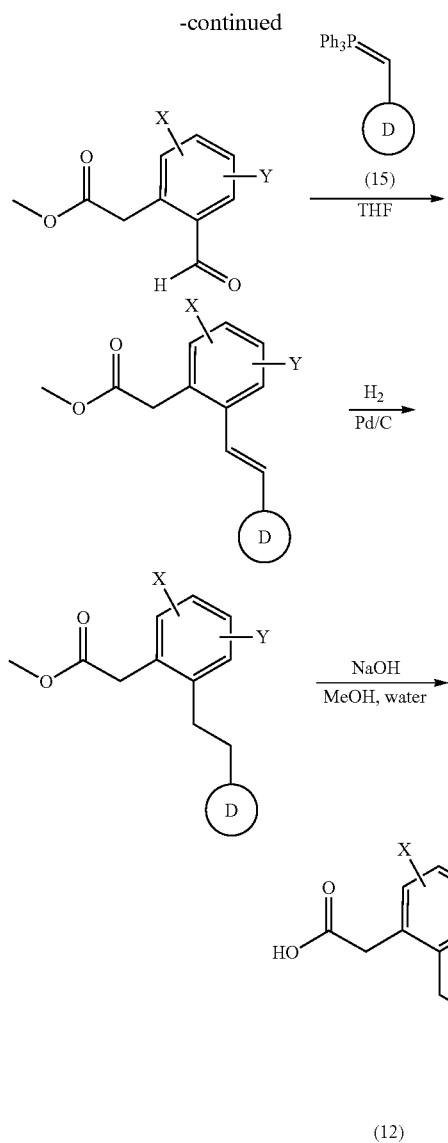

(12)

With respect to Reaction scheme 8, phosphoranes (15) can be made according to Reaction scheme 9.

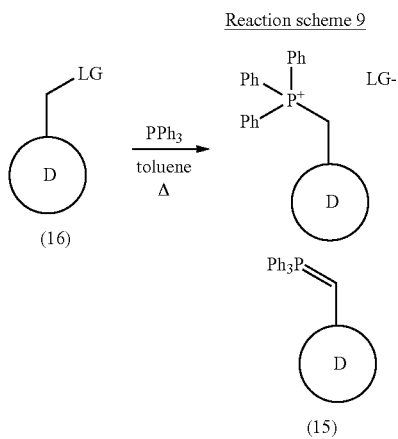

With respect to Reaction scheme 9, examples of suitable bases are sodium hydride, sodium hexamethyldisilazide and potassium tert-butoxide. Compounds (16) are electrophiles wherein LG is a Leaving Group [such as chloride, bromide, iodide, tosylate or mesylate]. Many compounds (16) are commercially available [such as 4-chlorobenzyl bromide or 2-chloro-5-chloromethylthiazole].

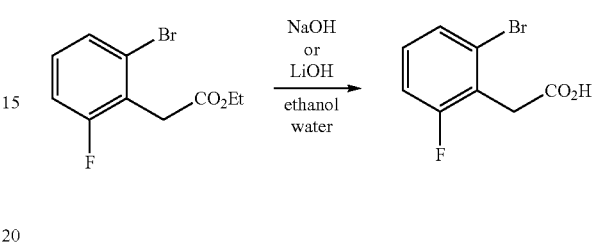

With respect to Reaction scheme 10, (2-Bromo-6-fluorophenyl)acetic acid ethyl ester may be prepared as described in Lundgren et al. *JACS* 2016, 138, 13826-13829.

With respect to Reaction scheme 11, 2-Bromo-1-chloro-4-fluoro-benzene is commercially available.

Reaction scheme 12

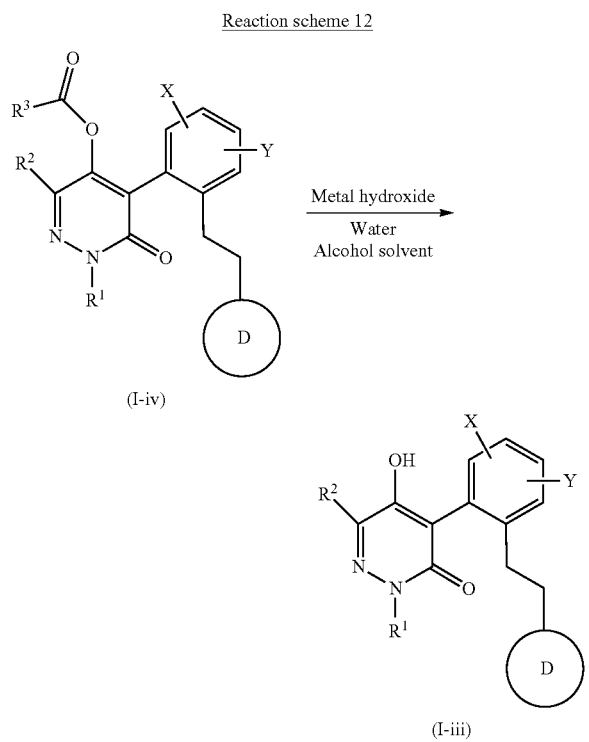

(I-iv)

(I-iii)

Compounds (I-iii) may be prepared by treating compounds (I-iv) with a metal hydroxide [such as sodium hydroxide, lithium hydroxide or potassium hydroxide] in a mixture of water and an alcohol solvent [such as methanol or ethanol] at a temperature between 0° C. and 100° C. Compounds (I-iv) are compounds of formula (I) in which W is —$CH_2$—$CH_2$— and G is $C(O)R^3$.

Compositions of the invention also comprise, as component (B), a compound of formula (II) as defined supra. Preferred substituents for compounds of formula (II) are as follows.

Preferably $R^{B11}$ is H, $C_1$-$C_6$ alkyl or $C_1$-$C_6$haloalkyl, more preferably methyl, ethyl or $CHF_2$, and more preferably still, H or methyl.

Preferably $R^{B6}$ is H.

Preferably $Q^{B1}$ is either a phenyl ring or a pyridinyl ring, each of which is optionally substituted by 1 to 3 $R^4$.

Preferably $Q^{B3}$ is a phenyl ring substituted by 1 to 2 $R^{B4}$.

Preferably $Q^{12}$ is a phenyl ring, optionally substituted by 1 to 3 $R^{B5}$. More preferably $Q^B$, is phenyl substituted by 1-3 $R^{B5}$.

Preferably each $R^{B4}$ is independently halogen, $C_1$-$C_4$ alkyl, $C_1$-$C_3$ haloalkyl, $C_1$-$C_3$alkoxy, or $C_1$-$C_3$haloalkoxy; more preferably chloro, fluoro, bromo, $C_1$-$C_2$haloalkyl, $C_1$-$C_2$haloalkoxy, or $C_1$-$C_2$alkoxy.

Preferably each $R^{B5}$ is independently halogen, $C_1$-$C_4$ alkyl, $C_1$-$C_3$ haloalkyl, $C_1$-$C_3$alkoxy, or $C_1$-$C_3$haloalkoxy; more preferably chloro, fluoro, bromo, $C_1$-$C_2$haloalkyl, $C_1$-$C_2$haloalkoxy, or $C_1$-$C_2$alkoxy; more preferably still fluoro.

Particularly preferred compounds of formula (II) for use as component B in compositions of the invention are shown below in Table 2.

Table 2

| Compound of formula (II) for use in compositions described herein. | | |
|---|---|---|
| Compound No. | Name | Structure |
| 2.1 | N-(2-fluorophenyl)-2-oxo-4-[3-(trifluoromethyl)phenyl]pyrrolidine-3-carboxamide | |
| 2.2 | N-(2,3-difluorophenyl)-2-oxo-4-[3-(trifluoromethyl)phenyl]pyrrolidine-3-carboxamide | |

Table 2-continued

Compound of formula (II) for use in compositions described herein.

| Compound No. | Name | Structure |
|---|---|---|
| 2.3 | 2-oxo-4-[3-(trifluoromethyl)phenyl]-N-(2,3,4-trifluorophenyl)pyrrolidine-3-carboxamide | 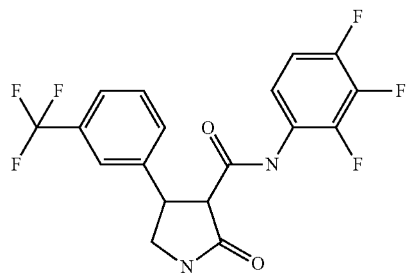 [SMILES: O=C1NCC(c2cccc(C(F)(F)F)c2)C1C(=O)Nc1ccc(F)c(F)c1F] |
| 2.4 | N-(2-fluorophenyl)-1-methyl-2-oxo-4-[3-(trifluoromethyl)phenyl]pyrrolidine-3-carboxamide | 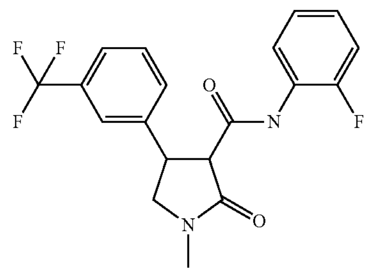 [SMILES: CN1CC(c2cccc(C(F)(F)F)c2)C(C(=O)Nc2ccccc2F)C1=O] |
| 2.5 | N-(2-fluorophenyl)-2-oxo-4-[4-(trifluoromethyl)phenyl]pyrrolidine-3-carboxamide | 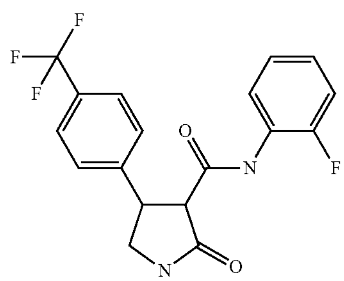 [SMILES: O=C1NCC(c2ccc(C(F)(F)F)cc2)C1C(=O)Nc1ccccc1F] |
| 2.6 | N-(2-fluorophenyl)-1-methyl-2-oxo-4-[4-(trifluoromethyl)phenyl]pyrrolidine-3-carboxamide | 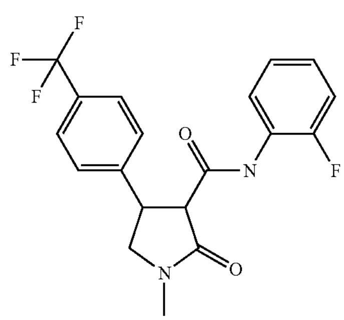 [SMILES: CN1CC(c2ccc(C(F)(F)F)cc2)C(C(=O)Nc2ccccc2F)C1=O] |
| 2.7 | N-(2,3-difluorophenyl)-2-oxo-4-[4-(trifluoromethyl)phenyl]pyrrolidine-3-carboxamide | 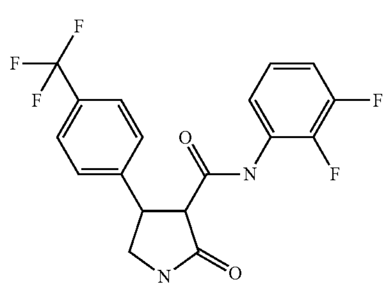 [SMILES: O=C1NCC(c2ccc(C(F)(F)F)cc2)C1C(=O)Nc1cccc(F)c1F] |

Table 2-continued

Compound of formula (II) for use in compositions described herein.

| Compound No. | Name | Structure |
|---|---|---|
| 2.8 | N-(2,3-difluorophenyl)-1-methyl-2-oxo-4-[4-(trifluoromethyl)phenyl]pyrrolidine-3-carboxamide | 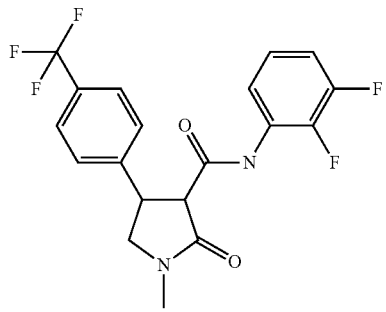 [SMILES: CN1CC(c2ccc(C(F)(F)F)cc2)C(C(=O)Nc2cccc(F)c2F)C1=O] |
| 2.9 | 2-oxo-4-[4-(trifluoromethyl)phenyl]-N-(2,3,4-trifluorophenyl)pyrrolidine-3-carboxamide | 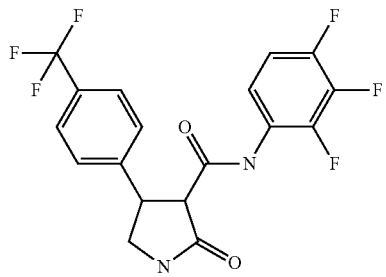 [SMILES: O=C1NCC(c2ccc(C(F)(F)F)cc2)C1C(=O)Nc1ccc(F)c(F)c1F] |
| 2.10 | N-(2-fluorophenyl)-4-(4-fluorophenyl)-1-methyl-2-oxo-pyrrolidine-3-carboxamide | 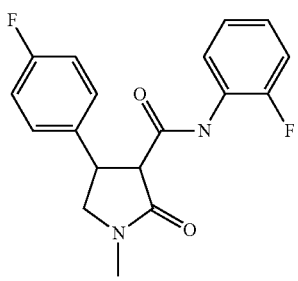 [SMILES: CN1CC(c2ccc(F)cc2)C(C(=O)Nc2ccccc2F)C1=O] |
| 2.11 | N-(2,3-difluorophenyl)-4-(3,4-difluorophenyl)-2-oxo-pyrrolidine-3-carboxamide | 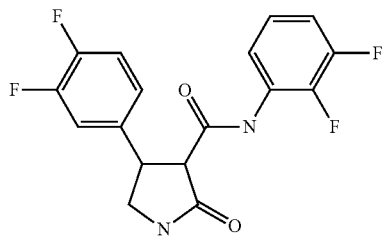 [SMILES: O=C1NCC(c2ccc(F)c(F)c2)C1C(=O)Nc1cccc(F)c1F] |
| 2.12 | 4-(3,4-difluorophenyl)-N-(2-fluorophenyl)-2-oxo-pyrrolidine-3-carboxamide | 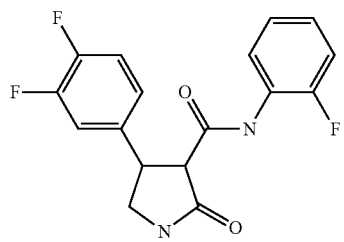 [SMILES: O=C1NCC(c2ccc(F)c(F)c2)C1C(=O)Nc1ccccc1F] |

Table 2-continued

Compound of formula (II) for use in compositions described herein.

| Compound No. | Name | Structure |
|---|---|---|
| 2.13 | N-(2,4-difluorophenyl)-4-(3,5-difluorophenyl)-2-oxo-pyrrolidine-3-carboxamide | 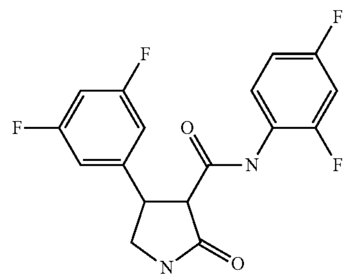 [SMILES: O=C1NCC(c2cc(F)cc(F)c2)C1C(=O)Nc1ccc(F)cc1F] |
| 2.14 | N-(2,3-difluorophenyl)-4-(3-isopropylphenyl)-2-oxo-pyrrolidine-3-carboxamide | 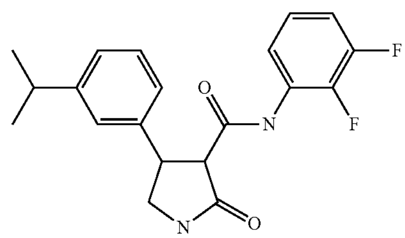 [SMILES: CC(C)c1cccc(C2CNC(=O)C2C(=O)Nc2cccc(F)c2F)c1] |
| 2.15 | N-(2,3-difluorophenyl)-2-oxo-4-[6-(trifluoromethyl)-3-pyridyl]pyrrolidine-3-carboxamide | 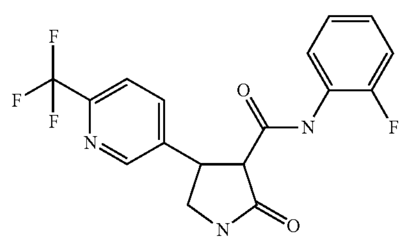 [SMILES: O=C1NCC(c2ccc(C(F)(F)F)nc2)C1C(=O)Nc1ccccc1F] |
| 2.16 | 4-(3,5-difluorophenyl)-N-[3-fluoro-2-(trifluoromethyl)phenyl]-1-methyl-2-oxo-pyrrolidine-3-carboxamide | 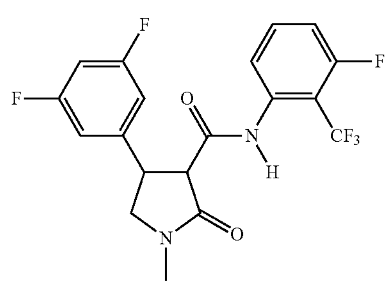 [SMILES: CN1CC(c2cc(F)cc(F)c2)C(C(=O)Nc2cccc(F)c2C(F)(F)F)C1=O] |
| 2.17 | N-(2,4-difluorophenyl)-4-(3,5-difluorophenyl)-1-methyl-2-oxo-pyrrolidine-3-carboxamide | 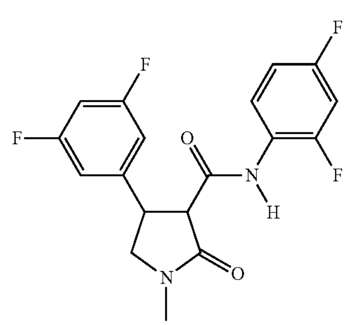 [SMILES: CN1CC(c2cc(F)cc(F)c2)C(C(=O)Nc2ccc(F)cc2F)C1=O] |

Table 2-continued

Compound of formula (II) for use in compositions described herein.

| Compound No. | Name | Structure |
|---|---|---|
| 2.18 | N-(2,3-difluorophenyl)-4-(3,5-difluorophenyl)-1-methyl-2-oxo-pyrrolidine-3-carboxamide | 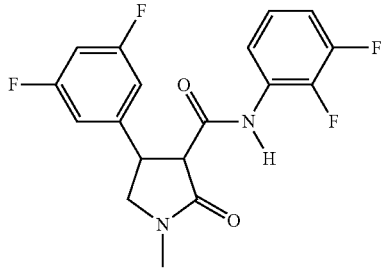 |

In one embodiment B is compound 2.1.
In one embodiment B is compound 2.2.
In one embodiment B is compound 2.3.
In one embodiment B is compound 2.4.
In one embodiment B is compound 2.5.
In one embodiment B is compound 2.6.
In one embodiment B is compound 2.7.
In one embodiment B is compound 2.8.
In one embodiment B is compound 2.9.
In one embodiment B is compound 2.10.
In one embodiment B is compound 2.11.
In one embodiment B is compound 2.12.
In one embodiment B is compound 2.13.
In one embodiment B is compound 2.14.
In one embodiment B is compound 2.15.
In one embodiment B is compound 2.16.
In one embodiment B is compound 2.17.
In one embodiment B is compound 2.18.

Compounds of formula (II) as described herein may be made as described in WO2015/084796 and WO 2016/094117.

Preferred compositions of the present invention are selected from the group consisting of those which comprise:

as (A) any one of compounds 1.001 to 1.308 from table 1 with compound 2.1 as (B);
as (A) any one of compounds 1.001 to 1.308 from table 1 with compound 2.2 as (B);
as (A) any one of compounds 1.001 to 1.308 from table 1 with compound 2.3 as (B);
as (A) any one of compounds 1.001 to 1.308 from table 1 with compound 2.4 as (B);
as (A) any one of compounds 1.001 to 1.308 from table 1 with compound 2.5 as (B);
as (A) any one of compounds 1.001 to 1.308 from table 1 with compound 2.6 as (B);
as (A) any one of compounds 1.001 to 1.308 from table 1 with compound 2.7 as (B);
as (A) any one of compounds 1.001 to 1.308 from table 1 with compound 2.8 as (B);
as (A) any one of compounds 1.001 to 1.308 from table 1 with compound 2.9 as (B);
as (A) any one of compounds 1.001 to 1.308 from table 1 with compound 2.10 as (B);
as (A) any one of compounds 1.001 to 1.308 from table 1 with compound 2.11 as (B);
as (A) any one of compounds 1.001 to 1.308 from table 1 with compound 2.12 as (B);
as (A) any one of compounds 1.001 to 1.308 from table 1 with compound 2.13 as (B);
as (A) any one of compounds 1.001 to 1.308 from table 1 with compound 2.14 as (B);
as (A) any one of compounds 1.001 to 1.308 from table 1 with compound 2.15 as (B);
as (A) any one of compounds 1.001 to 1.308 from table 1 with compound 2.16 as (B);
as (A) any one of compounds 1.001 to 1.308 from table 1 with compound 2.17 as (B); and
as (A) any one of compounds 1.001 to 1.308 from table 1 with compound 2.18 as (B).

Throughout this document the expression "composition" stands for the various mixtures or combinations of components (A) and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example killing, retardation, leaf burn, albinism, dwarfing and the like.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The term "safener" as used herein means a chemical that when used in combination with a herbicide reduces the undesirable effects of the herbicide on non-target organisms, for example, a safener protects crops from injury by herbicides but does not prevent the herbicide from killing the weeds.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

In all aspects of the invention, in any particular embodiment, the weeds, e.g. to be controlled and/or growth-inhibited, may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Compositions of this invention can also be mixed with one or more further pesticides including herbicides [typically different to the herbicides of formula (I) and formula (II)], fungicides, insecticides, nematocides, bactericides, acaricides, growth regulators, chemosterilants, semiochemicals, repellents, attractants, pheromones, feeding stimulants or other biologically active compounds to form a multicomponent pesticide giving an even broader spectrum of agricultural protection.

Similarly compositions of the invention (which includes those comprising one or more additional pesticide as described in the preceding paragraph) can further include one or more safeners. In particular, the following safeners are especially preferred: AD 67 (MON 4660), benoxacor, cloquintocet-mexyl, cyometrinil, cyprosulfamide, dichlormid, dicyclonon, diethatole, fenchlorazole-ethyl, fenclorim, flurazole, fluxofenim, furilazole, furilazome, isoxadifenethyl, mefenpyr-diethyl, mephenate, oxabetrinil, naphthalic anhydride (CAS RN 81-84-5), TI-35, N-isopropyl-4-(2-methoxy-benzoylsulfamoyl)-benzamide (CAS RN 221668-34-4) and N-(2-methoxybenzoyl)-4-[(methylaminocarbonyl)amino]benzenesulfonamide. Such safeners may also be used in the form of esters or salts, as mentioned e.g. in The Pesticide Manual, 15th Ed. (BCPC), 2009. Thus, the reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

In general, the mixing ratio (by weight) of the compound of formula (I) to the compound of formula (II) is from 0.01:1 to 100:1, more preferably from 0.05:1 to 20:1, even more preferably from 0.1:1 to 20:1 and most preferably from 0.2:1 to 20:1, for example, 0.3125:1, 0.625:1, 1.25:1, 2.5:1, 5:1, 10:1 and 20:1.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

When applied to the useful plants component (A) is typically applied at a rate of 50 to 2000 g a.i./ha, particularly 100 to 1000 g a.i./ha and more particularly 300 to 500 g a.i./ha e.g. 300, 350, 400, 450 or 500 g a.i./ha, typically in association with 50 to 2000 g a.i./ha of component (B).

In agricultural practice the application rates of the composition according to the invention depend on the type of effect desired, and typically range from 100 to 4000 g of total composition per hectare.

The compounds of the invention can be applied before or after planting of the crops, before weeds emerge (pre-emergence application) or after weeds emerge (post-emergence application).

Where a safener is combined with mixtures of the invention, it is preferred that the mixing ratio of compound of formula (I) to safener is from 100:1 to 1:10, especially from 20:1 to 1:1.

It is possible that the safener and the compositions of the invention are applied simultaneously. For example, the safener and the composition of the invention might be applied to the locus pre-emergence or might be applied to the crop post-emergence. It is also possible that the safener and the composition of the invention are applied sequentially. For example, the safener might be applied before sowing the seeds as a seed treatment and the composition of the invention might be applied to the locus pre-emergence or might be applied to the crop post-emergence.

The compositions of the invention can advantageously be used in the below-mentioned formulations (in which case "active ingredient" relates to the respective mixture of compound of formula (I) with a compound of formula (II) or, when a safener is also used, the respective mixture of the compound of formula (I) with the compound of formula (II) and the safener).

The individual components of the composition of the invention may be utilised as the technical active ingredient as produced. More typically however, the compositions according to the invention may be formulated in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The formulations generally comprise from 0.1 to 99% by weight, especially from 0.1 to 95% by weight, of compounds (A) and (B) and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %), wherein the term "active ingredient" refers to the total weight % of the combination of all active ingredients in the composition:

Emulsifiable Concentrates:
    active ingredient: 1 to 95%, preferably 60 to 90%
    surface-active agent: 1 to 30%, preferably 5 to 20%
    liquid carrier: 1 to 80%, preferably 1 to 35%

Dusts:
    active ingredient: 0.1 to 10%, preferably 0.1 to 5%
    solid carrier: 99.9 to 90%, preferably 99.9 to 99%

Suspension Concentrates:
    active ingredient: 5 to 75%, preferably 10 to 50%
    water: 94 to 24%, preferably 88 to 30%
    surface-active agent: 1 to 40%, preferably 2 to 30%

Wettable Powders:
    active ingredient: 0.5 to 90%, preferably 1 to 80%
    surface-active agent: 0.5 to 20%, preferably 1 to 15%
    solid carrier: 5 to 95%, preferably 15 to 90%

Granules:
    active ingredient: 0.1 to 30%, preferably 0.1 to 15%
    solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulphate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruded aranules | |
|---|---|
| Active ingredients | 15% |
| sodium lignosulfonate | 2% |
| Carboxymethylcellulose | 1% |
| Kaolin | 82% |

The combination is mixed and ground with the adjuvants, and the mixture is moistened with water. The mixture is extruded and then dried in a stream of air.

| Coated aranules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension

28 Parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Throughout this document the expression "composition" stands for the various mixtures or combinations of components (A) and (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components (A) and (B) is not essential for working the present invention.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example killing, retardation, leaf burn, albinism, dwarfing and the like.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The term "safener" as used herein means a chemical that when used in combination with a herbicide reduces the undesirable effects of the herbicide on non-target organisms, for example, a safener protects crops from injury by herbicides but does not prevent the herbicide from killing the weeds.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm;

ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compositions of the invention can typically be used to control a wide variety of monocotyledonous and dicotyledonous weed species. Examples of monocotyledonous species that can typically be controlled include *Alopecurus myosuroides, Avena fatua, Brachiaria plantaginea, Bromus tectorum, Cyperus esculentus, Digitaria sanguinalis, Echinochloa crus-galli, Lolium perenne, Lolium multiflorum, Panicum miliaceum, Poa annua, Setaria viridis, Setaria faberi* and *Sorghum bicolor*. Examples of dicotyledonous species that can be controlled include *Abutilon theophrasti, Amaranthus retroflexus, Bidens pilosa, Chenopodium album, Euphorbia heterophylla, Galium aparine, Ipomoea hederacea, Kochia scoparia, Polygonum convolvulus, Sida spinosa, Sinapis arvensis, Solanum nigrum, Stellaria media, Veronica persica* and *Xanthium strumarium*.

In all aspects of the invention, in any particular embodiment, the weeds, e.g. to be controlled and/or growth-inhibited, may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Compositions of this invention can also be mixed with one or more further pesticides including fungicides, insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection.

The compositions of the invention can advantageously be used in the above-mentioned formulations (in which case "active ingredient" relates to the respective mixture of compound of formula (I) with a compound of formula (II) or, when a safener is also used, the respective mixture of the compound of formula (I) with the compound of formula (II) and the safener).

In general, the mixing ratio (by weight) of the compound of formula (I) to the compound of formula (II) is from 0.01:1 to 100:1, more preferably from 0.05:1 to 20:1, even more preferably from 0.1:1 to 20:1 and most preferably from 0.2:1 to 20:1, for example, 1:4, 0.3125:1, 1:3, 1:2, 0.625:1, 2:3, 1:1, 1.25:1, 2:1, 2.5:1, 3:1, 4:1, 5:1, 10:1 and 20:1.

The amount of a composition according to the invention to be applied, will depend on various factors, such as the compounds employed; the subject of the treatment, such as, for example plants, soil or seeds; the type of treatment, such as, for example spraying, dusting or seed dressing; and the purpose of the treatment, such as, for example selective or non-selective control of unwanted plants, and/or pre- or and/or post-emergence weed control.

When applied to the useful plants, or the locus thereof, component (A) is typically applied at a rate of 50 to 2000 g a.i./ha, particularly 100 to 1000 g a.i./ha and more particularly 300 to 500 g a.i./ha e.g. 300, 350, 400, 450 or 500 g a.i./ha, typically in association with 50 to 2000 g a.i./ha of component (B).

In agricultural practice the application rates of the composition according to the invention depend on the type of effect desired, and typically range from 100 to 4000 g of total composition per hectare.

Preferably the mixing ratio of compound of formula (I) to safener is from 100:1 to 1:10, especially from 20:1 to 1:1.

The compounds of the invention can be applied before or after planting of the crops, before weeds emerge (pre-emergence application) or after weeds emerge (post-emergence application), and are particularly effective when applied pre-emergence to the weeds.

It is possible that the safener and the compositions of the invention are applied simultaneously. For example, the safener and the composition of the invention might be applied to the locus pre-emergence or might be applied to the crop post-emergence. It is also possible that the safener and the composition of the invention are applied sequentially. For example, the safener might be applied before sowing the seeds as a seed treatment and the composition of the invention might be applied to the locus pre-emergence or might be applied to the crop post-emergence.

Particularly preferred compositions of the invention comprise at least one compound of formula (I) as defined supra in the Examples. In one set of embodiments the composition of the invention will comprise A and B as described in Table 3 below.

TABLE 3

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 1 | 1.001 | 2.1 | 0.01:1 to 100:1 | 0.05:1 to 20:1 | 0.1:1 to 20:1 |
| 2 | 1.002 | 2.1 | 0.01:1 to 100:1 | 0.05:1 to 20:1 | 0.1:1 to 20:1 |
| 3 | 1.012 | 2.1 | 0.01:1 to 100:1 | 0.05:1 to 20:1 | 0.1:1 to 20:1 |
| 4 | 1.018 | 2.1 | 0.01:1 to 100:1 | 0.05:1 to 20:1 | 0.1:1 to 20:1 |
| 5 | 1.024 | 2.1 | 0.01:1 to 100:1 | 0.05:1 to 20:1 | 0.1:1 to 20:1 |
| 6 | 1.042 | 2.1 | 0.01:1 to 100:1 | 0.05:1 to 20:1 | 0.1:1 to 20:1 |
| 7 | 1.048 | 2.1 | 0.01:1 to 100:1 | 0.05:1 to 20:1 | 0.1:1 to 20:1 |
| 8 | 1.054 | 2.1 | 0.01:1 to 100:1 | 0.05:1 to 20:1 | 0.1:1 to 20:1 |
| 9 | 1.060 | 2.1 | 0.01:1 to 100:1 | 0.05:1 to 20:1 | 0.1:1 to 20:1 |
| 10 | 1.066 | 2.1 | 0.01:1 to 100:1 | 0.05:1 to 20:1 | 0.1:1 to 20:1 |
| 11 | 1.089 | 2.1 | 0.01:1 to 100:1 | 0.05:1 to 20:1 | 0.1:1 to 20:1 |
| 12 | 1.095 | 2.1 | 0.01:1 to 100:1 | 0.05:1 to 20:1 | 0.1:1 to 20:1 |
| 13 | 1.125 | 2.1 | 0.01:1 to 100:1 | 0.05:1 to 20:1 | 0.1:1 to 20:1 |
| 14 | 1.149 | 2.1 | 0.01:1 to 100:1 | 0.05:1 to 20:1 | 0.1:1 to 20:1 |
| 15 | 1.001 | 2.2 | 0.01:1 to 100:1 | 0.05:1 to 20:1 | 0.1:1 to 20:1 |
| 16 | 1.002 | 2.2 | 0.01:1 to 100:1 | 0.05:1 to 20:1 | 0.1:1 to 20:1 |
| 17 | 1.012 | 2.2 | 0.01:1 to 100:1 | 0.05:1 to 20:1 | 0.1:1 to 20:1 |
| 18 | 1.018 | 2.2 | 0.01:1 to 100:1 | 0.05:1 to 20:1 | 0.1:1 to 20:1 |
| 19 | 1.024 | 2.2 | 0.01:1 to 100:1 | 0.05:1 to 20:1 | 0.1:1 to 20:1 |
| 20 | 1.042 | 2.2 | 0.01:1 to 100:1 | 0.05:1 to 20:1 | 0.1:1 to 20:1 |
| 21 | 1.048 | 2.2 | 0.01:1 to 100:1 | 0.05:1 to 20:1 | 0.1:1 to 20:1 |
| 22 | 1.054 | 2.2 | 0.01:1 to 100:1 | 0.05:1 to 20:1 | 0.1:1 to 20:1 |
| 23 | 1.060 | 2.2 | 0.01:1 to 100:1 | 0.05:1 to 20:1 | 0.1:1 to 20:1 |
| 24 | 1.066 | 2.2 | 0.01:1 to 100:1 | 0.05:1 to 20:1 | 0.1:1 to 20:1 |
| 25 | 1.089 | 2.2 | 0.01:1 to 100:1 | 0.05:1 to 20:1 | 0.1:1 to 20:1 |
| 26 | 1.095 | 2.2 | 0.01:1 to 100:1 | 0.05:1 to 20:1 | 0.1:1 to 20:1 |
| 27 | 1.125 | 2.2 | 0.01:1 to 100:1 | 0.05:1 to 20:1 | 0.1:1 to 20:1 |
| 28 | 1.149 | 2.2 | 0.01:1 to 100:1 | 0.05:1 to 20:1 | 0.1:1 to 20:1 |
| 29 | 1.001 | 2.3 | 0.01:1 to 100:1 | 0.05:1 to 20:1 | 0.1:1 to 20:1 |
| 30 | 1.002 | 2.3 | 0.01:1 to 100:1 | 0.05:1 to 20:1 | 0.1:1 to 20:1 |
| 31 | 1.012 | 2.3 | 0.01:1 to 100:1 | 0.05:1 to 20:1 | 0.1:1 to 20:1 |
| 32 | 1.018 | 2. | 0.01:1 to 100:1 | 0.05:1 to 20:1 | 0.1:1 to 20:1 |
| 33 | 1.024 | 2.3 | 0.01:1 to 100:1 | 0.05:1 to 20:1 | 0.1:1 to 20:1 |
| 34 | 1.042 | 2.3 | 0.01:1 to 100:1 | 0.05:1 to 20:1 | 0.1:1 to 20:1 |
| 35 | 1.048 | 2.3 | 0.01:1 to 100:1 | 0.05:1 to 20:1 | 0.1:1 to 20:1 |
| 36 | 1.054 | 2.3 | 0.01:1 to 100:1 | 0.05:1 to 20:1 | 0.1:1 to 20:1 |
| 37 | 1.060 | 2.3 | 0.01:1 to 100:1 | 0.05:1 to 20:1 | 0.1:1 to 20:1 |
| 38 | 1.066 | 2.3 | 0.01:1 to 100:1 | 0.05:1 to 20:1 | 0.1:1 to 20:1 |
| 39 | 1.089 | 2.3 | 0.01:1 to 100:1 | 0.05:1 to 20:1 | 0.1:1 to 20:1 |
| 40 | 1.095 | 2.3 | 0.01:1 to 100:1 | 0.05:1 to 20:1 | 0.1:1 to 20:1 |
| 41 | 1.125 | 2.3 | 0.01:1 to 100:1 | 0.05:1 to 20:1 | 0.1:1 to 20:1 |
| 42 | 1.149 | 2.3 | 0.01:1 to 100:1 | 0.05:1 to 20:1 | 0.1:1 to 20:1 |
| 43 | 1.001 | 2.4 | 0.01:1 to 100:1 | 0.05:1 to 20:1 | 0.1:1 to 20:1 |
| 44 | 1.002 | 2.4 | 0.01:1 to 100:1 | 0.05:1 to 20:1 | 0.1:1 to 20:1 |
| 45 | 1.012 | 2.4 | 0.01:1 to 100:1 | 0.05:1 to 20:1 | 0.1:1 to 20:1 |
| 46 | 1.018 | 2.4 | 0.01:1 to 100:1 | 0.05:1 to 20:1 | 0.1:1 to 20:1 |
| 47 | 1.024 | 2.4 | 0.01:1 to 100:1 | 0.05:1 to 20:1 | 0.1:1 to 20:1 |
| 48 | 1.042 | 2.4 | 0.01:1 to 100:1 | 0.05:1 to 20:1 | 0.1:1 to 20:1 |
| 49 | 1.048 | 2.4 | 0.01:1 to 100:1 | 0.05:1 to 20:1 | 0.1:1 to 20:1 |
| 50 | 1.054 | 2.4 | 0.01:1 to 100:1 | 0.05:1 to 20:1 | 0.1:1 to 20:1 |
| 51 | 1.060 | 2.4 | 0.01:1 to 100:1 | 0.05:1 to 20:1 | 0.1:1 to 20:1 |
| 52 | 1.066 | 2.4 | 0.01:1 to 100:1 | 0.05:1 to 20:1 | 0.1:1 to 20:1 |
| 53 | 1.089 | 2.4 | 0.01:1 to 100:1 | 0.05:1 to 20:1 | 0.1:1 to 20:1 |
| 54 | 1.095 | 2.4 | 0.01:1 to 100:1 | 0.05:1 to 20:1 | 0.1:1 to 20:1 |
| 55 | 1.125 | 2.4 | 0.01:1 to 100:1 | 0.05:1 to 20:1 | 0.1:1 to 20:1 |
| 56 | 1.149 | 2.4 | 0.01:1 to 100:1 | 0.05:1 to 20:1 | 0.1:1 to 20:1 |
| 57 | 1.001 | 2.5 | 0.01:1 to 100:1 | 0.05:1 to 20:1 | 0.1:1 to 20:1 |
| 58 | 1.002 | 2.5 | 0.01:1 to 100:1 | 0.05:1 to 20:1 | 0.1:1 to 20:1 |
| 59 | 1.012 | 2.5 | 0.01:1 to 100:1 | 0.05:1 to 20:1 | 0.1:1 to 20:1 |
| 60 | 1.018 | 2.5 | 0.01:1 to 100:1 | 0.05:1 to 20:1 | 0.1:1 to 20:1 |
| 61 | 1.024 | 2.5 | 0.01:1 to 100:1 | 0.05:1 to 20:1 | 0.1:1 to 20:1 |
| 62 | 1.042 | 2.5 | 0.01:1 to 100:1 | 0.05:1 to 20:1 | 0.1:1 to 20:1 |
| 63 | 1.048 | 2.5 | 0.01:1 to 100:1 | 0.05:1 to 20:1 | 0.1:1 to 20:1 |
| 64 | 1.054 | 2.5 | 0.01:1 to 100:1 | 0.05:1 to 20:1 | 0.1:1 to 20:1 |
| 65 | 1.060 | 2.5 | 0.01:1 to 100:1 | 0.05:1 to 20:1 | 0.1:1 to 20:1 |
| 66 | 1.066 | 2.5 | 0.01:1 to 100:1 | 0.05:1 to 20:1 | 0.1:1 to 20:1 |
| 67 | 1.089 | 2.5 | 0.01:1 to 100:1 | 0.05:1 to 20:1 | 0.1:1 to 20:1 |
| 68 | 1.095 | 2.5 | 0.01:1 to 100:1 | 0.05:1 to 20:1 | 0.1:1 to 20:1 |
| 69 | 1.125 | 2.5 | 0.01:1 to 100:1 | 0.05:1 to 20:1 | 0.1:1 to 20:1 |
| 70 | 1.149 | 2.5 | 0.01:1 to 100:1 | 0.05:1 to 20:1 | 0.1:1 to 20:1 |
| 71 | 1.001 | 2.6 | 0.01:1 to 100:1 | 0.05:1 to 20:1 | 0.1:1 to 20:1 |
| 72 | 1.002 | 2.6 | 0.01:1 to 100:1 | 0.05:1 to 20:1 | 0.1:1 to 20:1 |
| 73 | 1.012 | 2.6 | 0.01:1 to 100:1 | 0.05:1 to 20:1 | 0.1:1 to 20:1 |
| 74 | 1.018 | 2.6 | 0.01:1 to 100:1 | 0.05:1 to 20:1 | 0.1:1 to 20:1 |
| 75 | 1.024 | 2.6 | 0.01:1 to 100:1 | 0.05:1 to 20:1 | 0.1:1 to 20:1 |

TABLE 3-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 76 | 1.042 | 2.6 | 0.01:1 to 100:1 | 0.05:1 to 20:1 | 0.1:1 to 20:1 |
| 77 | 1.048 | 2.6 | 0.01:1 to 100:1 | 0.05:1 to 20:1 | 0.1:1 to 20:1 |
| 78 | 1.054 | 2.6 | 0.01:1 to 100:1 | 0.05:1 to 20:1 | 0.1:1 to 20:1 |
| 79 | 1.060 | 2.6 | 0.01:1 to 100:1 | 0.05:1 to 20:1 | 0.1:1 to 20:1 |
| 80 | 1.066 | 2.6 | 0.01:1 to 100:1 | 0.05:1 to 20:1 | 0.1:1 to 20:1 |
| 81 | 1.089 | 2.6 | 0.01:1 to 100:1 | 0.05:1 to 20:1 | 0.1:1 to 20:1 |
| 82 | 1.095 | 2.6 | 0.01:1 to 100:1 | 0.05:1 to 20:1 | 0.1:1 to 20:1 |
| 83 | 1.125 | 2.6 | 0.01:1 to 100:1 | 0.05:1 to 20:1 | 0.1:1 to 20:1 |
| 84 | 1.149 | 2.6 | 0.01:1 to 100:1 | 0.05:1 to 20:1 | 0.1:1 to 20:1 |
| 85 | 1.001 | 2.7 | 0.01:1 to 100:1 | 0.05:1 to 20:1 | 0.1:1 to 20:1 |
| 86 | 1.002 | 2.7 | 0.01:1 to 100:1 | 0.05:1 to 20:1 | 0.1:1 to 20:1 |
| 87 | 1.012 | 2.7 | 0.01:1 to 100:1 | 0.05:1 to 20:1 | 0.1:1 to 20:1 |
| 88 | 1.018 | 2.7 | 0.01:1 to 100:1 | 0.05:1 to 20:1 | 0.1:1 to 20:1 |
| 89 | 1.024 | 2.7 | 0.01:1 to 100:1 | 0.05:1 to 20:1 | 0.1:1 to 20:1 |
| 90 | 1.042 | 2.7 | 0.01:1 to 100:1 | 0.05:1 to 20:1 | 0.1:1 to 20:1 |
| 91 | 1.048 | 2.7 | 0.01:1 to 100:1 | 0.05:1 to 20:1 | 0.1:1 to 20:1 |
| 92 | 1.054 | 2.7 | 0.01:1 to 100:1 | 0.05:1 to 20:1 | 0.1:1 to 20:1 |
| 93 | 1.060 | 2.7 | 0.01:1 to 100:1 | 0.05:1 to 20:1 | 0.1:1 to 20:1 |
| 94 | 1.066 | 2.7 | 0.01:1 to 100:1 | 0.05:1 to 20:1 | 0.1:1 to 20:1 |
| 95 | 1.089 | 2.7 | 0.01:1 to 100:1 | 0.05:1 to 20:1 | 0.1:1 to 20:1 |
| 96 | 1.095 | 2.7 | 0.01:1 to 100:1 | 0.05:1 to 20:1 | 0.1:1 to 20:1 |
| 97 | 1.125 | 2.7 | 0.01:1 to 100:1 | 0.05:1 to 20:1 | 0.1:1 to 20:1 |
| 98 | 1.149 | 2.7 | 0.01:1 to 100:1 | 0.05:1 to 20:1 | 0.1:1 to 20:1 |
| 99 | 1.001 | 2.8 | 0.01:1 to 100:1 | 0.05:1 to 20:1 | 0.1:1 to 20:1 |
| 100 | 1.002 | 2.8 | 0.01:1 to 100:1 | 0.05:1 to 20:1 | 0.1:1 to 20:1 |
| 101 | 1.012 | 2.8 | 0.01:1 to 100:1 | 0.05:1 to 20:1 | 0.1:1 to 20:1 |
| 102 | 1.018 | 2.8 | 0.01:1 to 100:1 | 0.05:1 to 20:1 | 0.1:1 to 20:1 |
| 103 | 1.024 | 2.8 | 0.01:1 to 100:1 | 0.05:1 to 20:1 | 0.1:1 to 20:1 |
| 104 | 1.042 | 2.8 | 0.01:1 to 100:1 | 0.05:1 to 20:1 | 0.1:1 to 20:1 |
| 105 | 1.048 | 2.8 | 0.01:1 to 100:1 | 0.05:1 to 20:1 | 0.1:1 to 20:1 |
| 106 | 1.054 | 2.8 | 0.01:1 to 100:1 | 0.05:1 to 20:1 | 0.1:1 to 20:1 |
| 107 | 1.060 | 2.8 | 0.01:1 to 100:1 | 0.05:1 to 20:1 | 0.1:1 to 20:1 |
| 108 | 1.066 | 2.8 | 0.01:1 to 100:1 | 0.05:1 to 20:1 | 0.1:1 to 20:1 |
| 109 | 1.089 | 2.8 | 0.01:1 to 100:1 | 0.05:1 to 20:1 | 0.1:1 to 20:1 |
| 110 | 1.095 | 2.8 | 0.01:1 to 100:1 | 0.05:1 to 20:1 | 0.1:1 to 20:1 |
| 111 | 1.125 | 2.8 | 0.01:1 to 100:1 | 0.05:1 to 20:1 | 0.1:1 to 20:1 |
| 112 | 1.149 | 2.8 | 0.01:1 to 100:1 | 0.05:1 to 20:1 | 0.1:1 to 20:1 |
| 113 | 1.001 | 2.9 | 0.01:1 to 100:1 | 0.05:1 to 20:1 | 0.1:1 to 20:1 |
| 114 | 1.002 | 2.9 | 0.01:1 to 100:1 | 0.05:1 to 20:1 | 0.1:1 to 20:1 |
| 115 | 1.012 | 2.9 | 0.01:1 to 100:1 | 0.05:1 to 20:1 | 0.1:1 to 20:1 |
| 116 | 1.018 | 2.9 | 0.01:1 to 100:1 | 0.05:1 to 20:1 | 0.1:1 to 20:1 |
| 117 | 1.024 | 2.9 | 0.01:1 to 100:1 | 0.05:1 to 20:1 | 0.1:1 to 20:1 |
| 118 | 1.042 | 2.9 | 0.01:1 to 100:1 | 0.05:1 to 20:1 | 0.1:1 to 20:1 |
| 119 | 1.048 | 2.9 | 0.01:1 to 100:1 | 0.05:1 to 20:1 | 0.1:1 to 20:1 |
| 120 | 1.054 | 2.9 | 0.01:1 to 100:1 | 0.05:1 to 20:1 | 0.1:1 to 20:1 |
| 121 | 1.060 | 2.9 | 0.01:1 to 100:1 | 0.05:1 to 20:1 | 0.1:1 to 20:1 |
| 122 | 1.066 | 2.9 | 0.01:1 to 100:1 | 0.05:1 to 20:1 | 0.1:1 to 20:1 |
| 123 | 1.089 | 2.9 | 0.01:1 to 100:1 | 0.05:1 to 20:1 | 0.1:1 to 20:1 |
| 124 | 1.095 | 2.9 | 0.01:1 to 100:1 | 0.05:1 to 20:1 | 0.1:1 to 20:1 |
| 125 | 1.125 | 2.9 | 0.01:1 to 100:1 | 0.05:1 to 20:1 | 0.1:1 to 20:1 |
| 126 | 1.149 | 2.9 | 0.01:1 to 100:1 | 0.05:1 to 20:1 | 0.1:1 to 20:1 |
| 127 | 1.001 | 2.10 | 0.01:1 to 100:1 | 0.05:1 to 20:1 | 0.1:1 to 20:1 |
| 128 | 1.002 | 2.10 | 0.01:1 to 100:1 | 0.05:1 to 20:1 | 0.1:1 to 20:1 |
| 129 | 1.012 | 2.10 | 0.01:1 to 100:1 | 0.05:1 to 20:1 | 0.1:1 to 20:1 |
| 130 | 1.018 | 2.10 | 0.01:1 to 100:1 | 0.05:1 to 20:1 | 0.1:1 to 20:1 |
| 131 | 1.024 | 2.10 | 0.01:1 to 100:1 | 0.05:1 to 20:1 | 0.1:1 to 20:1 |
| 132 | 1.042 | 2.10 | 0.01:1 to 100:1 | 0.05:1 to 20:1 | 0.1:1 to 20:1 |
| 133 | 1.048 | 2.10 | 0.01:1 to 100:1 | 0.05:1 to 20:1 | 0.1:1 to 20:1 |
| 134 | 1.054 | 2.10 | 0.01:1 to 100:1 | 0.05:1 to 20:1 | 0.1:1 to 20:1 |
| 135 | 1.060 | 2.10 | 0.01:1 to 100:1 | 0.05:1 to 20:1 | 0.1:1 to 20:1 |
| 136 | 1.066 | 2.10 | 0.01:1 to 100:1 | 0.05:1 to 20:1 | 0.1:1 to 20:1 |
| 137 | 1.089 | 2.10 | 0.01:1 to 100:1 | 0.05:1 to 20:1 | 0.1:1 to 20:1 |
| 138 | 1.095 | 2.10 | 0.01:1 to 100:1 | 0.05:1 to 20:1 | 0.1:1 to 20:1 |
| 139 | 1.125 | 2.10 | 0.01:1 to 100:1 | 0.05:1 to 20:1 | 0.1:1 to 20:1 |
| 140 | 1.149 | 2.10 | 0.01:1 to 100:1 | 0.05:1 to 20:1 | 0.1:1 to 20:1 |
| 141 | 1.001 | 2.11 | 0.01:1 to 100:1 | 0.05:1 to 20:1 | 0.1:1 to 20:1 |
| 142 | 1.002 | 2.11 | 0.01:1 to 100:1 | 0.05:1 to 20:1 | 0.1:1 to 20:1 |
| 143 | 1.012 | 2.11 | 0.01:1 to 100:1 | 0.05:1 to 20:1 | 0.1:1 to 20:1 |
| 144 | 1.018 | 2.11 | 0.01:1 to 100:1 | 0.05:1 to 20:1 | 0.1:1 to 20:1 |
| 145 | 1.024 | 2.11 | 0.01:1 to 100:1 | 0.05:1 to 20:1 | 0.1:1 to 20:1 |
| 146 | 1.042 | 2.11 | 0.01:1 to 100:1 | 0.05:1 to 20:1 | 0.1:1 to 20:1 |
| 147 | 1.048 | 2.11 | 0.01:1 to 100:1 | 0.05:1 to 20:1 | 0.1:1 to 20:1 |
| 148 | 1.054 | 2.11 | 0.01:1 to 100:1 | 0.05:1 to 20:1 | 0.1:1 to 20:1 |
| 149 | 1.060 | 2.11 | 0.01:1 to 100:1 | 0.05:1 to 20:1 | 0.1:1 to 20:1 |
| 150 | 1.066 | 2.11 | 0.01:1 to 100:1 | 0.05:1 to 20:1 | 0.1:1 to 20:1 |

TABLE 3-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 151 | 1.089 | 2.11 | 0.01:1 to 100:1 | 0.05:1 to 20:1 | 0.1:1 to 20:1 |
| 152 | 1.095 | 2.11 | 0.01:1 to 100:1 | 0.05:1 to 20:1 | 0.1:1 to 20:1 |
| 153 | 1.125 | 2.11 | 0.01:1 to 100:1 | 0.05:1 to 20:1 | 0.1:1 to 20:1 |
| 154 | 1.149 | 2.11 | 0.01:1 to 100:1 | 0.05:1 to 20:1 | 0.1:1 to 20:1 |
| 155 | 1.001 | 2.12 | 0.01:1 to 100:1 | 0.05:1 to 20:1 | 0.1:1 to 20:1 |
| 156 | 1.002 | 2.12 | 0.01:1 to 100:1 | 0.05:1 to 20:1 | 0.1:1 to 20:1 |
| 157 | 1.012 | 2.12 | 0.01:1 to 100:1 | 0.05:1 to 20:1 | 0.1:1 to 20:1 |
| 158 | 1.018 | 2.12 | 0.01:1 to 100:1 | 0.05:1 to 20:1 | 0.1:1 to 20:1 |
| 159 | 1.024 | 2.12 | 0.01:1 to 100:1 | 0.05:1 to 20:1 | 0.1:1 to 20:1 |
| 160 | 1.042 | 2.12 | 0.01:1 to 100:1 | 0.05:1 to 20:1 | 0.1:1 to 20:1 |
| 161 | 1.048 | 2.12 | 0.01:1 to 100:1 | 0.05:1 to 20:1 | 0.1:1 to 20:1 |
| 162 | 1.054 | 2.12 | 0.01:1 to 100:1 | 0.05:1 to 20:1 | 0.1:1 to 20:1 |
| 163 | 1.060 | 2.12 | 0.01:1 to 100:1 | 0.05:1 to 20:1 | 0.1:1 to 20:1 |
| 164 | 1.066 | 2.12 | 0.01:1 to 100:1 | 0.05:1 to 20:1 | 0.1:1 to 20:1 |
| 165 | 1.089 | 2.12 | 0.01:1 to 100:1 | 0.05:1 to 20:1 | 0.1:1 to 20:1 |
| 166 | 1.095 | 2.12 | 0.01:1 to 100:1 | 0.05:1 to 20:1 | 0.1:1 to 20:1 |
| 167 | 1.125 | 2.12 | 0.01:1 to 100:1 | 0.05:1 to 20:1 | 0.1:1 to 20:1 |
| 168 | 1.149 | 2.12 | 0.01:1 to 100:1 | 0.05:1 to 20:1 | 0.1:1 to 20:1 |
| 169 | 1.001 | 2.13 | 0.01:1 to 100:1 | 0.05:1 to 20:1 | 0.1:1 to 20:1 |
| 170 | 1.002 | 2.13 | 0.01:1 to 100:1 | 0.05:1 to 20:1 | 0.1:1 to 20:1 |
| 171 | 1.012 | 2.13 | 0.01:1 to 100:1 | 0.05:1 to 20:1 | 0.1:1 to 20:1 |
| 172 | 1.018 | 2.13 | 0.01:1 to 100:1 | 0.05:1 to 20:1 | 0.1:1 to 20:1 |
| 173 | 1.024 | 2.13 | 0.01:1 to 100:1 | 0.05:1 to 20:1 | 0.1:1 to 20:1 |
| 174 | 1.042 | 2.13 | 0.01:1 to 100:1 | 0.05:1 to 20:1 | 0.1:1 to 20:1 |
| 175 | 1.048 | 2.13 | 0.01:1 to 100:1 | 0.05:1 to 20:1 | 0.1:1 to 20:1 |
| 176 | 1.054 | 2.13 | 0.01:1 to 100:1 | 0.05:1 to 20:1 | 0.1:1 to 20:1 |
| 177 | 1.060 | 2.13 | 0.01:1 to 100:1 | 0.05:1 to 20:1 | 0.1:1 to 20:1 |
| 178 | 1.066 | 2.13 | 0.01:1 to 100:1 | 0.05:1 to 20:1 | 0.1:1 to 20:1 |
| 179 | 1.089 | 2.13 | 0.01:1 to 100:1 | 0.05:1 to 20:1 | 0.1:1 to 20:1 |
| 180 | 1.095 | 2.13 | 0.01:1 to 100:1 | 0.05:1 to 20:1 | 0.1:1 to 20:1 |
| 181 | 1.125 | 2.13 | 0.01:1 to 100:1 | 0.05:1 to 20:1 | 0.1:1 to 20:1 |
| 182 | 1.149 | 2.13 | 0.01:1 to 100:1 | 0.05:1 to 20:1 | 0.1:1 to 20:1 |
| 183 | 1.001 | 2.14 | 0.01:1 to 100:1 | 0.05:1 to 20:1 | 0.1:1 to 20:1 |
| 184 | 1.002 | 2.14 | 0.01:1 to 100:1 | 0.05:1 to 20:1 | 0.1:1 to 20:1 |
| 185 | 1.012 | 2.14 | 0.01:1 to 100:1 | 0.05:1 to 20:1 | 0.1:1 to 20:1 |
| 186 | 1.018 | 2.14 | 0.01:1 to 100:1 | 0.05:1 to 20:1 | 0.1:1 to 20:1 |
| 187 | 1.024 | 2.14 | 0.01:1 to 100:1 | 0.05:1 to 20:1 | 0.1:1 to 20:1 |
| 188 | 1.042 | 2.14 | 0.01:1 to 100:1 | 0.05:1 to 20:1 | 0.1:1 to 20:1 |
| 189 | 1.048 | 2.14 | 0.01:1 to 100:1 | 0.05:1 to 20:1 | 0.1:1 to 20:1 |
| 190 | 1.054 | 2.14 | 0.01:1 to 100:1 | 0.05:1 to 20:1 | 0.1:1 to 20:1 |
| 191 | 1.060 | 2.14 | 0.01:1 to 100:1 | 0.05:1 to 20:1 | 0.1:1 to 20:1 |
| 192 | 1.066 | 2.14 | 0.01:1 to 100:1 | 0.05:1 to 20:1 | 0.1:1 to 20:1 |
| 193 | 1.089 | 2.14 | 0.01:1 to 100:1 | 0.05:1 to 20:1 | 0.1:1 to 20:1 |
| 194 | 1.095 | 2.14 | 0.01:1 to 100:1 | 0.05:1 to 20:1 | 0.1:1 to 20:1 |
| 195 | 1.125 | 2.14 | 0.01:1 to 100:1 | 0.05:1 to 20:1 | 0.1:1 to 20:1 |
| 196 | 1.149 | 2.14 | 0.01:1 to 100:1 | 0.05:1 to 20:1 | 0.1:1 to 20:1 |
| 197 | 1.001 | 2.15 | 0.01:1 to 100:1 | 0.05:1 to 20:1 | 0.1:1 to 20:1 |
| 198 | 1.002 | 2.15 | 0.01:1 to 100:1 | 0.05:1 to 20:1 | 0.1:1 to 20:1 |
| 199 | 1.012 | 2.15 | 0.01:1 to 100:1 | 0.05:1 to 20:1 | 0.1:1 to 20:1 |
| 200 | 1.018 | 2.15 | 0.01:1 to 100:1 | 0.05:1 to 20:1 | 0.1:1 to 20:1 |
| 201 | 1.024 | 2.15 | 0.01:1 to 100:1 | 0.05:1 to 20:1 | 0.1:1 to 20:1 |
| 202 | 1.042 | 2.15 | 0.01:1 to 100:1 | 0.05:1 to 20:1 | 0.1:1 to 20:1 |
| 203 | 1.048 | 2.15 | 0.01:1 to 100:1 | 0.05:1 to 20:1 | 0.1:1 to 20:1 |
| 204 | 1.054 | 2.15 | 0.01:1 to 100:1 | 0.05:1 to 20:1 | 0.1:1 to 20:1 |
| 205 | 1.060 | 2.15 | 0.01:1 to 100:1 | 0.05:1 to 20:1 | 0.1:1 to 20:1 |
| 206 | 1.066 | 2.15 | 0.01:1 to 100:1 | 0.05:1 to 20:1 | 0.1:1 to 20:1 |
| 207 | 1.089 | 2.15 | 0.01:1 to 100:1 | 0.05:1 to 20:1 | 0.1:1 to 20:1 |
| 208 | 1.095 | 2.15 | 0.01:1 to 100:1 | 0.05:1 to 20:1 | 0.1:1 to 20:1 |
| 209 | 1.125 | 2.15 | 0.01:1 to 100:1 | 0.05:1 to 20:1 | 0.1:1 to 20:1 |
| 210 | 1.149 | 2.15 | 0.01:1 to 100:1 | 0.05:1 to 20:1 | 0.1:1 to 20:1 |
| 211 | 1.001 | 2.16 | 0.01:1 to 100:1 | 0.05:1 to 20:1 | 0.1:1 to 20:1 |
| 212 | 1.002 | 2.16 | 0.01:1 to 100:1 | 0.05:1 to 20:1 | 0.1:1 to 20:1 |
| 213 | 1.012 | 2.16 | 0.01:1 to 100:1 | 0.05:1 to 20:1 | 0.1:1 to 20:1 |
| 214 | 1.018 | 2.16 | 0.01:1 to 100:1 | 0.05:1 to 20:1 | 0.1:1 to 20:1 |
| 215 | 1.024 | 2.16 | 0.01:1 to 100:1 | 0.05:1 to 20:1 | 0.1:1 to 20:1 |
| 216 | 1.042 | 2.16 | 0.01:1 to 100:1 | 0.05:1 to 20:1 | 0.1:1 to 20:1 |
| 217 | 1.048 | 2.16 | 0.01:1 to 100:1 | 0.05:1 to 20:1 | 0.1:1 to 20:1 |
| 218 | 1.054 | 2.16 | 0.01:1 to 100:1 | 0.05:1 to 20:1 | 0.1:1 to 20:1 |
| 219 | 1.060 | 2.16 | 0.01:1 to 100:1 | 0.05:1 to 20:1 | 0.1:1 to 20:1 |
| 220 | 1.066 | 2.16 | 0.01:1 to 100:1 | 0.05:1 to 20:1 | 0.1:1 to 20:1 |
| 221 | 1.089 | 2.16 | 0.01:1 to 100:1 | 0.05:1 to 20:1 | 0.1:1 to 20:1 |
| 222 | 1.095 | 2.16 | 0.01:1 to 100:1 | 0.05:1 to 20:1 | 0.1:1 to 20:1 |
| 223 | 1.125 | 2.16 | 0.01:1 to 100:1 | 0.05:1 to 20:1 | 0.1:1 to 20:1 |
| 224 | 1.149 | 2.16 | 0.01:1 to 100:1 | 0.05:1 to 20:1 | 0.1:1 to 20:1 |
| 225 | 1.001 | 2.17 | 0.01:1 to 100:1 | 0.05:1 to 20:1 | 0.1:1 to 20:1 |

TABLE 3-continued

Compositions of the Invention

| Composition Number | A Cmpd of formula (I) | B Cmpd of formula (II) | Typical Weight Ratio | Preferred Weight Ratio | More Preferred Weight Ratio |
|---|---|---|---|---|---|
| 226 | 1.002 | 2.17 | 0.01:1 to 100:1 | 0.05:1 to 20:1 | 0.1:1 to 20:1 |
| 227 | 1.012 | 2.17 | 0.01:1 to 100:1 | 0.05:1 to 20:1 | 0.1:1 to 20:1 |
| 228 | 1.018 | 2.17 | 0.01:1 to 100:1 | 0.05:1 to 20:1 | 0.1:1 to 20:1 |
| 229 | 1.024 | 2.17 | 0.01:1 to 100:1 | 0.05:1 to 20:1 | 0.1:1 to 20:1 |
| 230 | 1.042 | 2.17 | 0.01:1 to 100:1 | 0.05:1 to 20:1 | 0.1:1 to 20:1 |
| 231 | 1.048 | 2.17 | 0.01:1 to 100:1 | 0.05:1 to 20:1 | 0.1:1 to 20:1 |
| 232 | 1.054 | 2.17 | 0.01:1 to 100:1 | 0.05:1 to 20:1 | 0.1:1 to 20:1 |
| 233 | 1.060 | 2.17 | 0.01:1 to 100:1 | 0.05:1 to 20:1 | 0.1:1 to 20:1 |
| 234 | 1.066 | 2.17 | 0.01:1 to 100:1 | 0.05:1 to 20:1 | 0.1:1 to 20:1 |
| 235 | 1.089 | 2.17 | 0.01:1 to 100:1 | 0.05:1 to 20:1 | 0.1:1 to 20:1 |
| 236 | 1.095 | 2.17 | 0.01:1 to 100:1 | 0.05:1 to 20:1 | 0.1:1 to 20:1 |
| 237 | 1.125 | 2.17 | 0.01:1 to 100:1 | 0.05:1 to 20:1 | 0.1:1 to 20:1 |
| 238 | 1.149 | 2.17 | 0.01:1 to 100:1 | 0.05:1 to 20:1 | 0.1:1 to 20:1 |
| 239 | 1.001 | 2.18 | 0.01:1 to 100:1 | 0.05:1 to 20:1 | 0.1:1 to 20:1 |
| 240 | 1.002 | 2.18 | 0.01:1 to 100:1 | 0.05:1 to 20:1 | 0.1:1 to 20:1 |
| 241 | 1.012 | 2.18 | 0.01:1 to 100:1 | 0.05:1 to 20:1 | 0.1:1 to 20:1 |
| 242 | 1.018 | 2.18 | 0.01:1 to 100:1 | 0.05:1 to 20:1 | 0.1:1 to 20:1 |
| 243 | 1.024 | 2.18 | 0.01:1 to 100:1 | 0.05:1 to 20:1 | 0.1:1 to 20:1 |
| 244 | 1.042 | 2.18 | 0.01:1 to 100:1 | 0.05:1 to 20:1 | 0.1:1 to 20:1 |
| 245 | 1.048 | 2.18 | 0.01:1 to 100:1 | 0.05:1 to 20:1 | 0.1:1 to 20:1 |
| 246 | 1.054 | 2.18 | 0.01:1 to 100:1 | 0.05:1 to 20:1 | 0.1:1 to 20:1 |
| 247 | 1.060 | 2.18 | 0.01:1 to 100:1 | 0.05:1 to 20:1 | 0.1:1 to 20:1 |
| 248 | 1.066 | 2.18 | 0.01:1 to 100:1 | 0.05:1 to 20:1 | 0.1:1 to 20:1 |
| 249 | 1.089 | 2.18 | 0.01:1 to 100:1 | 0.05:1 to 20:1 | 0.1:1 to 20:1 |
| 250 | 1.095 | 2.18 | 0.01:1 to 100:1 | 0.05:1 to 20:1 | 0.1:1 to 20:1 |
| 251 | 1.125 | 2.18 | 0.01:1 to 100:1 | 0.05:1 to 20:1 | 0.1:1 to 20:1 |
| 252 | 1.149 | 2.18 | 0.01:1 to 100:1 | 0.05:1 to 20:1 | 0.1:1 to 20:1 |

The skilled man will appreciate that the most preferred ratio range of A:B for any one of composition numbers 1 to 252 described in Table X above is from 0.2:1 to 20:1, and that each one of composition numbers 1 to 252 described in Table X may used at the ratio of A:B of 0.3125:1, or at the ratio of A:B of 0.625:1, or at the ratio of A:B of 1.25:1, or at the ratio of A:B of 2.5:1, or at the ratio of A:B of 5:1, or at the ratio of A:B of 10:1, or at the ratio of A:B of 20:1.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

PREPARATION EXAMPLES FOR COMPOUNDS OF FORMULA (1)

Example 1 Preparation of 4-(3-chloro-6-fluoro-2-phenethyl-phenyl)-5-hydroxy-2,6-dimethyl-pyridazin-3-one

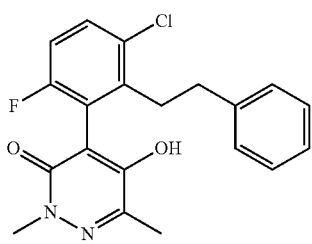 [SMILES: Cc1nn(C)c(=O)c(-c2c(F)ccc(Cl)c2CCc2ccccc2)c1O]

1.1 3-allyl-2-bromo-1-chloro-4-fluoro-benzene

A solution of lithium diisopropylamide (2M in tetrahydrofuran, 3.6 ml, 7.2 mmol) was cooled to −78° C. under $N_2$. A solution of 2-bromo-1-chloro-4-fluoro-benzene (1.0 g, 4.8 mmol) in tetrahydrofuran was added dropwise at −78° C. The mixture was stirred for 45 minutes at the same temperature before being treated with allyl bromide (0.3 ml, 5.7 mmol). The reaction was continued at −78° C. for 2 h then allowed to warm to rt. The reaction was quenched with sat. $NH_4Cl$ (aq) and extracted with ethyl acetate. The organics were separated and kept, then washed with brine. The organics were dried over sodium sulfate and concentrated under reduced pressure to give 3-allyl-2-bromo-1-chloro-4-fluoro-benzene (1.2 g, 100%) as an oil.

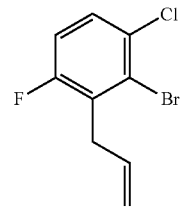

$^1$H NMR (400 MHz, $CDCl_3$) $\delta_H$: 7.34-7.30 (m, 1H), 7.01-6.96 (m, 1H), 5.94-5.83 (m, 1H), 5.10-5.00 (m, 2H), 3.64-3.58 (m, 2H).

1.2 2-(2-bromo-3-chloro-6-fluoro-phenyl)acetic Acid

A solution of 3-allyl-2-bromo-1-chloro-4-fluoro-benzene (15.0 g, 60.1 mmol) in dichloromethane (200 mL) in a 2-necked flask was cooled to −78° C. One side neck was connected to a trap containing an aqueous solution of KI.

Ozone was bubbled through the solution until the starting material was fully consumed (5 hours). Air was bubbled through the solution for 10 minutes to remove excess ozone. Dimethyl sulfide (44 ml, 601 mmol) was added and the mixture allowed to warm to rt. The reaction was continued for 16 h at rt.

The mixture was washed with brine (2×100 mL) and the organic layer kept. The organics were dried over $Na_2SO_4$, filtered and concentrated under reduced pressure to give crude 2-(2-bromo-3-chloro-6-fluoro-phenyl)acetaldehyde (15.3 g) which was used for the next step without further purification.

Crude 2-(2-bromo-3-chloro-6-fluoro-phenyl)acetaldehyde (15.3 g, 60.8 mmol) was dissolved in a mixture of tert-butanol (92 mL) and water (46 mL) then cooled to 0° C. 2-methylbut-2-ene (64.5 mL, 608 mmol), sodium dihydrogen phosphate (34.6 g, 243 mmol) and sodium chlorite (16.5 g, 163 mmol) were added. The mixture was stirred for 2 h then diluted with brine (150 mL) and 2M hydrochloric acid (150 mL). The mixture was extracted with ethyl acetate (3×100 mL). The combined organic extracts were washed with a saturated aqueous solution of sodium metabisulfite (100 mL) then dried over $Na_2SO_4$, filtered and concentrated under reduced pressure to provide a pale yellow solid. The crude solid was dissolved in a mixture of water (100 mL) and 2.0M NaOH (30 mL). The aqueous solution was washed with ethyl acetate (100 mL) and the organics discarded. The aqueous layer was acidified by addition of concentrated hydrochloric acid (20 mL) resulting in the formation of a white suspension. The mixture was extracted with ethyl acetate (3×200 mL). The combined organics were washed with brine, dried over $Na_2SO_4$, filtered and evaporated to provide 2-(2-bromo-3-chloro-6-fluoro-phenyl)acetic acid (8.0 g, 49%) as a white solid.

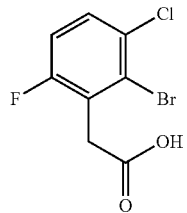

$^1$H NMR (400 MHz, DMSO-d6) $\delta_H$: 12.79 (br.s, 1H), 7.67-7.59 (m, 1H), 7.39-7.31 (m, 1H), 3.82 (s, 2H).

1.3 2-(2-bromo-3-chloro-6-fluoro-phenyl)-N-methyl-acetohydrazide

To a stirred solution of 2-(2-bromo-3-chloro-6-fluoro-phenyl)acetic acid (2.0 g, 7.5 mmol) in dichloromethane (20 ml) at 0° C. was added N-(3-Dimethylaminopropyl)-N'-ethylcarbodiimide hydrochloride [EDC·HCl] (1.4 g, 9.0 mmol), followed by dropwise addition of methyl hydrazine (0.4 ml, 7.5 mmol). The temperature of the reaction mixture was maintained at 0° C. for 3 h. The reaction was then quenched with water and extracted into dichloromethane. The organics were separated, washed with brine and dried over $Na_2SO_4$. Concentration under reduced pressure gave crude 2-(2-bromo-3-chloro-6-fluoro-phenyl)-N-methyl-acetohydrazide (1.8 g, 81%) which was used in the next step without further purification.

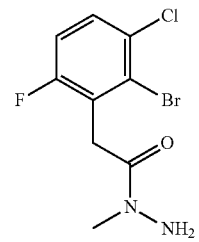

$^1$H NMR (400 MHz, DMSO-d6) $\delta_H$: 7.59 (dd, J=8.9 and 5.4, 1H), 7.30 (t, J=8.9, 1H), 4.91 (s, 2H), 4.10 (br. s, 2H), 3.02 (s, 3H).

1.4 2-{[2-(2-Bromo-3-chloro-6-fluoro-phenyl)-acetyl]-methyl-hydrazono}-propionic Acid ethyl ester To a stirred solution of 2-(2-bromo-3-chloro-6-fluoro-phenyl)-N-methyl-acetohydrazide (1.8 g, 6.09 mmol) in ethanol (5 ml) was added ethyl pyruvate (0.7 ml, 6.7 mmol) dropwise. The reaction was heated at 80° C. for 4 h. The reaction mixture was then allowed to cool to rt, and evaporated under reduced pressure. The residue was purified by column chromatography on silica gel (eluent an ethyl acetate/hexane gradient) to give the desired compound 2-{[2-(2-Bromo-3-chloro-6-fluoro-phenyl)-acetyl]-methyl-hydrazono}-propionic acid ethyl ester (1.8 g, 75%) as an off-white solid.

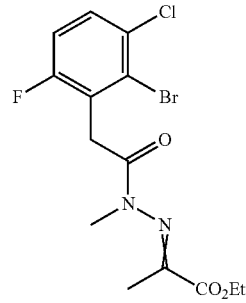 [SMILES: CCOC(=O)C(C)=NN(C)C(=O)Cc1c(F)ccc(Cl)c1Br]

$^1$H NMR (400 MHz, CDCl$_3$) $\delta_H$:7.40-7.35 (m, 1H), 7.04-6.98 (m, 1H), 4.32 (q, J=7.1, 2H), 4.24 (s, 2H), 3.41 (s, 3H), 2.32 (s, 3H), 1.36 (t, J=7.1, 3H).

1.5 4-(2-bromo-3-chloro-6-fluoro-phenyl)-5-hydroxy-2,6-dimethyl-pyridazin-3-one 2-{[2-(2-Bromo-3-chloro-6-fluoro-phenyl)-acetyl]-methyl-hydrazono}-propionic acid ethyl ester (500 mg, 1.27 mmol) was dissolved in acetonitrile (2.5 ml) and treated with 1,8-diazabicyclo[5.4.0]undec-7-ene [DBU] (0.47 ml, 3.2 mmol). The mixture was heated to 125° C. using microwave irradiation for 1 h. The reaction mixture was then evaporated under reduced pressure. The residue was dissolved in water and acidified to pH 1 with 2N hydrochloric acid. The mixture was extracted with DCM, the organics separated and washed with brine solution. The organic solution was dried over $Na_2SO_4$ and concentrated under reduced pressure to give crude product. The crude was purified by column chromatography on silica gel (eluent an ethyl acetate/hexane gradient) to give 4-(2-bromo-3-chloro-6-fluoro-phenyl)-5-hydroxy-2,6-dimethyl-pyridazin-3-one (340 mg, 77.1%) as an off-white solid.

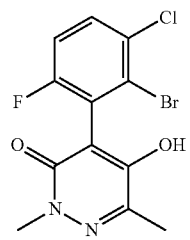 [SMILES: Cc1nn(C)c(=O)c(-c2c(F)ccc(Cl)c2Br)c1O]

¹H NMR (400 MHz, DMSO-d6) δ$_H$: 11.01 (s, 1H), 7.77-7.73 (m, 1H), 7.39 (t, J=8.7, 1H), 3.58 (s, 3H), 2.24 (s, 3H).

1.6 [5-(2-bromo-3-chloro-6-fluoro-phenyl)-1,3-dimethyl-6-oxo-pyridazin-4-yl] 2-methylpropanoate To a stirred solution of 4-(2-bromo-3-chloro-6-fluoro-phenyl)-5-hydroxy-2,6-dimethyl-pyridazin-3-one (1.4 g, 4.02 mmol) in dichloromethane (32 ml) at rt were added triethylamine (1.1 ml, 8.06 mmol), 4-(dimethylamino)pyridine [DMAP] (49 mg, 0.40 mmol) and isobutyryl chloride (0.6 ml, 4.83 mmol).

Once judged complete, the reaction was diluted with dichloromethane and water. The organic layer was separated, dried over Na$_2$SO$_4$, and concentrated under reduced pressure to give crude product. The crude was purified by column chromatography on silica gel (eluent an ethyl acetate/hexane gradient) to give [5-(2-bromo-3-chloro-6-fluoro-phenyl)-1,3-dimethyl-6-oxo-pyridazin-4-yl] 2-methylpropanoate (1.47 g, 87%).

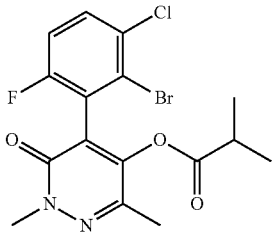 [SMILES: Cc1nn(C)c(=O)c(-c2c(F)ccc(Cl)c2Br)c1OC(=O)C(C)C]

¹H NMR (400 MHz, CDCl$_3$) δ$_H$: 7.51-7.47 (m, 1H), 7.10-7.05 (m, 1H), 3.82 (s, 3H), 2.60-2.55 (m, 1H), 2.25 (s, 3H), 1.02-0.98 (m, 6H).

1.7 4-[3-chloro-6-fluoro-2-[(E)-styryl]phenyl]-5-hydroxy-2,6-dimethyl-pyridazin-3-one Solid K$_2$CO$_3$ (298 mg, 2.16 mmol), trans-2-phenylvinylboronic acid (213 mg, 1.43 mmol) and PdCl$_2$(dppf).DCM (118 mg, 0.143 mmol) were placed under argon atmosphere. A solution of [5-(2-bromo-3-chloro-6-fluoro-phenyl)-1,3-dimethyl-6-oxo-pyridazin-4-yl] 2-methylpropanoate (250 mg, 0.72 mmol) in 1,4-dioxane (4 ml) was added and the mixture stirred at 95° C. for 18 h.

The reaction mixture was evaporated directly under reduced pressure to give a residue which was purified by column chromatography on silica gel (eluent an ethyl acetate/hexane gradient to give 4-[3-chloro-6-fluoro-2-[(E)-styryl]phenyl]-5-hydroxy-2,6-dimethyl-pyridazin-3-one (160 mg, 72%).

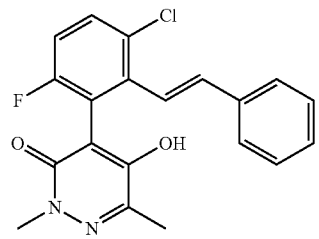 [SMILES: Cc1nn(C)c(=O)c(-c2c(F)ccc(Cl)c2/C=C/c2ccccc2)c1O]

¹H NMR (DMSO-d6) δ$_H$: 10.8 (s, 1H), 7.62 (m, 1H), 7.37-7.24 (m, 6H), 6.94 (d, J=16.5, 1H), 6.57 (d, J=16.5, 1H), 6.53 (s, 3H), 2.18 (s, 3H).

1.8 4-(3-chloro-6-fluoro-2-phenethyl-phenyl)-5-hydroxy-2,6-dimethyl-pyridazin-3-one A stirred mixture of 4-[3-chloro-6-fluoro-2-[(E)-styryl]phenyl]-5-hydroxy-2,6-di methyl-pyridazin-3-one (200 mg, 0.54 mmol) and Pd/C (40 mg) in tetrahydrofuran (10 ml) was treated with hydrogen under balloon pressure for 21 h.

The catalyst was removed by filtration and the reaction solution evaporated to dryness. The residue was purified by flash column chromatography on silica gel (eluent an ethyl acetate/hexanes gradient) to give 4-(3-chloro-6-fluoro-2-phenethyl-phenyl)-5-hydroxy-2,6-dimethyl-pyridazin-3-one (110 mg, 55%) as a white solid.

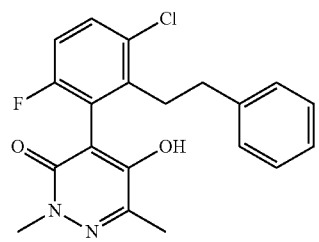 [SMILES: Cc1nn(C)c(=O)c(-c2c(F)ccc(Cl)c2CCc2ccccc2)c1O]

¹H NMR (DMSO-d6) δ$_H$: 10.85 (s, 1H), 7.57-7.53 (m, 1H), 7.27-7.15 (m, 4H), 7.0 (d, J=7.2, 2H), 3.60 (s, 3H), 2.73-2.50 (m, 4H), 2.25 (s, 3H).

Example 2 Preparation of 4-[3-chloro-6-fluoro-2-[2-(4-fluorophenyl)ethyl]phenyl]-5-hydroxy-2,6-dimethyl-pyridazin-3-one

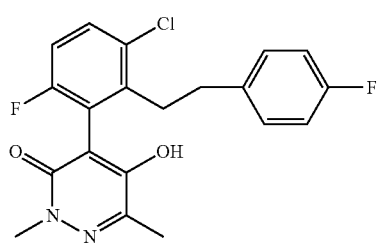 [SMILES: Cc1nn(C)c(=O)c(-c2c(F)ccc(Cl)c2CCc2ccc(F)cc2)c1O]

2.1 [5-[3-chloro-6-fluoro-2-[(E)-2-(4-fluorophenyl)vinyl]phenyl]-1,3-dimethyl-6-oxo-pyridazin-4-yl] 2-methylpropanoate A mixture of [5-(2-bromo-3-chloro-6-fluoro-phenyl)-1,3-dimethyl-6-oxo-pyridazin-4-yl] 2-methylpropanoate (0.50 g, 1.20 mmol, 1.0 equiv.) [prepared as described in Example 1], tris(dibenzylideneacetone)dipalladium(0) (27 mg, 0.030 mmol, 0.025 equiv.) and tri-tertbutylphosphonium tetrafluoroborate (35 mg, 0.12 mmol, 0.1 equiv.) was treated with degassed triethylamine (12 mL). 1-fluoro-4-vinyl-benzene (0.43 mL, 0.44 g, 3.59 mmol, 3.0 equiv.) was added and the mixture heated to 95° C. for 18.5 hrs.

Heating was halted and LC/MS analysis showed high conversion to the target stilbene. The reaction mixture was diluted with dichloromethane and filtered through celite, washing with further dichloromethane. The liquors were concentrated to dryness. The crude product was partially purified by flash column chromatography (silica, eluent ethyl acetate/isohexane) to afford desired stilbene [5-[3-chloro-6-fluoro-2-[(E)-2-(4-fluorophenyl)vinyl]phenyl]-1,3-dimethyl-6-oxo-pyridazin-4-yl] 2-methylpropanoate (0.36 g, 0.774 mmol, 65% yield) as a colourless gum.

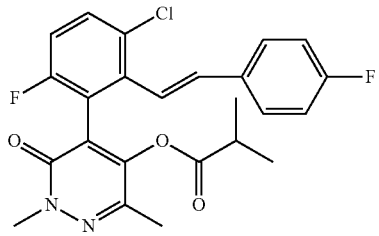

$^1$H NMR (400 MHz, CDCl$_3$) δ$_H$=7.45-7.41 (m, 1H), 7.35-7.30 (m, 2H), 7.04-6.98 (m, 3H), 6.93 (d, 1H), 6.61 (d, 1H), 3.71 (s, 3H), 2.64 (sept, 1H), 2.23 (s, 3H), 1.09 (dd, 6H).

2.2 [5-[3-chloro-6-fluoro-2-[2-(4-fluorophenyl)ethyl]phenyl]-1,3-dimethyl-6-oxo-pyridazin-4-yl] 2-methylpropanoate

[5-[3-chloro-6-fluoro-2-[(E)-2-(4-fluorophenyl)vinyl]phenyl]-1,3-dimethyl-6-oxo-pyridazin-4-yl] 2-methylpropanoate (130 mg, 0.283 mmol) was subjected to catalytic hydrogenation in tetrahydrofuran (3 mL) over 5% Pd/C catalyst (60 mg) at 3 barg H$_2$.

After 1.5 hrs, LC/MS showed complete reaction. The reaction mixture was filtered through a pad of celite, washing with ethyl acetate. The liquors were concentrated in-vacuo to afford a crude residue.

The residue was adsorbed onto silica and purified by flash column chromatography (silica, eluent ethyl acetate/isohexane) to give [5-[3-chloro-6-fluoro-2-[2-(4-fluorophenyl)ethyl]phenyl]-1,3-dimethyl-6-oxo-pyridazin-4-yl] 2-methylpropanoate (85 mg, 65% yield) as a colourless gum.

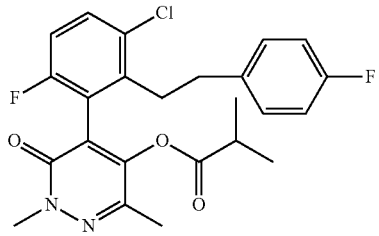 [SMILES: Cc1nn(C)c(=O)c(-c2c(F)ccc(Cl)c2CCc2ccc(F)cc2)c1OC(=O)C(C)C]

$^1$H NMR (400 MHz, CDCl$_3$) δ$_H$=7.42 (dd, 1H), 7.11-7.06 (m, 2H), 6.99 (t, 1H), 6.97-6.90 (m, 2H), 3.84 (s, 3H), 2.86-2.68 (m, 4H), 2.55 (sept, 1H), 2.26 (s, 3H), 0.98 (dd, 6H).

2.3 4-[3-chloro-6-fluoro-2-[2-(4-fluorophenyl)ethyl]phenyl]-5-hydroxy-2,6-dimethyl-pyridazin-3-one

[5-[3-chloro-6-fluoro-2-[2-(4-fluorophenyl)ethyl]phenyl]-1,3-dimethyl-6-oxo-pyridazin-4-yl]2-methylpropanoate (108 mg, 0.234 mmol, 1.0 equiv.) was dissolved in ethanol (7.5 mL). The mixture was treated with a solution of lithium hydroxide (17 mg, 0.703 mmol, 3.0 equiv.) in water (2.5 mL). The reaction was stirred at rt for 2 hrs.

LC/MS showed complete conversion. The reaction mixture was concentrated in-vacuo to remove ethanol. The remaining aqueous solution was acidified with 1M HCl (30 mL) and extracted with EtOAc (3×30 mL). The combined organics were dried over MgSO$_4$, filtered and concentrated in-vacuo to afford crude product.

Purification by flash column chromatography (silica, eluent ethyl acetate/isohexane) gave 4-[3-chloro-6-fluoro-2-[2-(4-fluorophenyl)ethyl]phenyl]-5-hydroxy-2,6-dimethyl-pyridazin-3-one (83 mg, 91% yield) as a white solid.

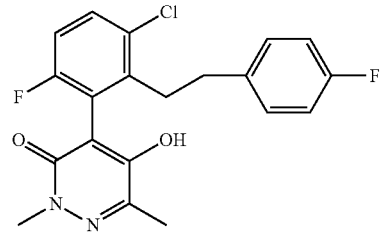 [SMILES: Cc1nn(C)c(=O)c(-c2c(F)ccc(Cl)c2CCc2ccc(F)cc2)c1O]

$^1$H NMR (400 MHz, CDCl$_3$) δ$_H$=7.44 (dd, 1H), 7.01-6.88 (m, 5H), 5.91 (br s, 1H), 3.73 (s, 3H), 2.81-2.65 (m 4H), 2.30 (s, 3H).

Example 3 Preparation of 4-[3-chloro-6-fluoro-2-[2-[6-(trifluoromethyl)-3-pyridyl]ethyl]phenyl]-5-hydroxy-2,6-dimethyl-pyridazin-3-one

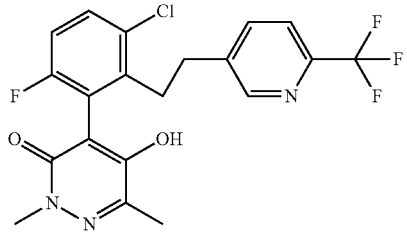 [SMILES: Cc1nn(C)c(=O)c(-c2c(F)ccc(Cl)c2CCc2ccc(C(F)(F)F)nc2)c1O]

3.1 [5-[3-chloro-6-fluoro-2-[(E)-2-[6-(trifluoromethyl)-3-pyridyl]vinyl]phenyl]-1,3-dimethyl-6-oxo-pyridazin-4-yl] 2-methylpropanoate Triethylamine (12 mL) was sparged with nitrogen for 2 minutes. It was then added to a mixture of [5-(2-bromo-3-chloro-6-fluoro-phenyl)-1,3-dimethyl-6-oxo-pyridazin-4-yl] 2-methylpropanoate (1.65 g, 3.95 mmol, 1.0 eq.) [prepared as described in Example 1], Pd$_2$(dba)$_3$ (90 mg, 0.099 mmol, 0.025 eq.) and tri tert-butylphosphonium tetrafluoroborate (115 mg, 0.40 mmol, 0.1 eq.). 2-(trifluoromethyl)-5-vinyl-pyridine (1.71 g, 9.88 mmol, 2.5 eq.) was added and the mixture heated at 95° C. for 6 hours.

The mixture was allowed to cool to room temperature then diluted with dichloromethane (20 mL). The mixture was washed with hydrochloric acid (20 mL, 2.0 M). The organics were dried over MgSO$_4$, filtered and concentrated in vacuo. The crude product was purified by flash column chromatography to provide [5-[3-chloro-6-fluoro-2-[(E)-2-[6-(trifluoromethyl)-3-pyridyl]vinyl]phenyl]-1,3-dimethyl-6-oxo-pyridazin-4-yl] 2-methylpropanoate (1.41 g, 2.76 mmol, 70% yield) as an orange oil.

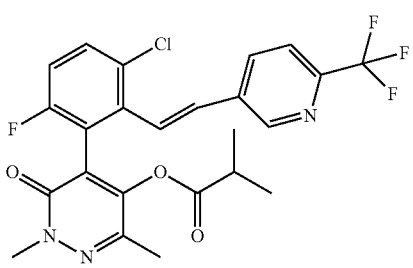 [SMILES: Cc1nn(C)c(=O)c(-c2c(F)ccc(Cl)c2/C=C/c2ccc(C(F)(F)F)nc2)c1OC(=O)C(C)C]

$^1$H NMR (400 MHz, CDCl$_3$) δ$_H$: 8.65 (d, J=1.6, 1H), 7.87 (dd, J=8.2 and 2.1, 1H), 7.64 (d, J=8.2, 1H), 7.47 (dd, J=8.9 and 5.0, 1H), 7.17 (d, J=16.5, 1H), 7.08 (t, J=8.7, 1H), 6.75 (d, J=16.5, 1H), 3.71 (s, 3H), 2.66 (spt, J=7.0, 1H), 2.24 (s, 3H), 1.11 (d, J=7.0, 3H), 1.08 (d, J=7.1, 3H).

3.2 [5-[3-chloro-6-fluoro-2-[2-[6-(trifluoromethyl)-3-pyridyl]ethyl]phenyl]-1,3-dimethyl-6-oxo-pyridazin-4-yl] 2-methylpropanoate Tetrahydrofuran (12 mL) was added to a mixture of [5-[3-chloro-6-fluoro-2-[(E)-2-[6-(trifluoromethyl)-3-pyridyl]vinyl]phenyl]-1,3-dimethyl-6-oxo-pyridazin-4-yl] 2-methylpropanoate (1.2 g, 2.4 mmol, 1.0 eq.) and 10% palladium on activated charcoal catalyst (0.25 g) under nitrogen atmosphere. The mixture was subjected to hydrogenation at 4 bar hydrogen for 16 hours.

The mixture was filtered through celite, washing with further tetrahydrofuran, and the filtrate was concentrated in vacuo. The crude product was purified by flash column chromatography to provide [5-[3-chloro-6-fluoro-2-[2-[6-(trifluoromethyl)-3-pyridyl]ethyl]phenyl]-1,3-dimethyl-6-oxo-pyridazin-4-yl] 2-methylpropanoate (1.1 g, 91% yield) as a colourless oil.

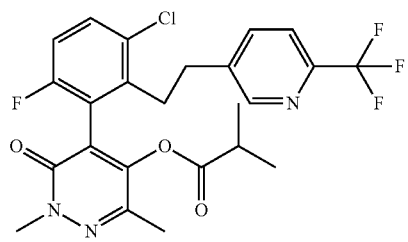 [SMILES: Cc1nn(C)c(=O)c(-c2c(F)ccc(Cl)c2CCc2ccc(C(F)(F)F)nc2)c1OC(=O)C(C)C]

$^1$H NMR (400 MHz, CDCl$_3$) δ$_H$: 8.53 (d, J=1.2, 1H), 7.69-7.63 (m, 1H), 7.62-7.55 (m, 1H), 7.44 (dd, J=8.8 and 5.1, 1H), 7.02 (t, J=8.6, 1H), 3.86 (s, 3H), 3.10-2.98 (m, 1H), 2.97-2.81 (m, 2H), 2.76-2.64 (m, 1H), 2.55 (spt, J=7.0, 1H), 2.26 (s, 3H), 0.99 (d, J=7.0, 3H), 0.95 (d, J=7.0, 3H).

3.3 4-[3-chloro-6-fluoro-2-[2-[6-(trifluoromethyl)-3-pyridyl]ethyl]phenyl]-5-hydroxy-2,6-dimethyl-pyridazin-3-one Lithium hydroxide (0.13 g, 5.3 mmol, 3.0 eq.) was added to a solution of [5-[3-chloro-6-fluoro-2-[2-[6-(trifluoromethyl)-3-pyridyl]ethyl]phenyl]-1,3-dimethyl-6-oxo-pyridazin-4-yl] 2-methylpropanoate (0.90 g, 1.8 mmol, 1.0 eq.) in a mixture of ethanol (13 mL) and water (4.4 mL). The mixture was stirred at room temperature for 2 days.

The mixture was concentrated in vacuo. The mixture was acidified to pH 1 by addition of hydrochloric acid (6.0 mL, 2.0 M) resulting in formation of a precipitate. The solid was isolated by filtration and re-dissolved in dichloromethane (40 mL). The dichloromethane solution was dried over MgSO$_4$, filtered and concentrated in vacuo to afford crude product. Purification by flash column chromatography gave impure title compound as a white foam. The material was further purified by reverse phase column chromatography to provide 4-[3-chloro-6-fluoro-2-[2-[6-(trifluoromethyl)-3-pyridyl]ethyl]phenyl]-5-hydroxy-2,6-dimethyl-pyridazin-3-one (0.232 g, 0.525 mmol, 30% yield) as a white foam.

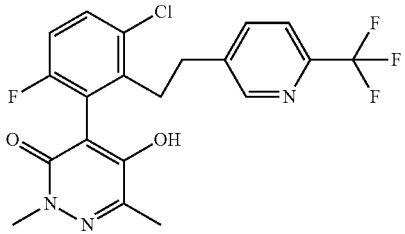 [SMILES: Cc1nn(C)c(=O)c(-c2c(F)ccc(Cl)c2CCc2ccc(C(F)(F)F)nc2)c1O]

$^1$H NMR (400 MHz, CDCl$_3$) δ$_H$: 8.30 (s, 1H), 7.54 (d, J=1.2, 2H), 7.37 (dd, J=8.8 and 5.1, 1H), 6.95 (t, J=8.5, 1H), 3.69 (s, 3H), 2.92-2.65 (m, 4H), 2.28 (s, 3H).

Compounds 1.001, 1.002, 1.012, 1.018, 1.024, 1.042, 1.048, 1.054, 1.060, 1.066, 1.089, 1.095, 1.125 and 1.149 were prepared using the general methods as described supra. Table 4 below shows the structure of these compounds and NMR characterising data.

TABLE 4

Preparation examples of compounds of formula (I). The numbering system used to describe the positions of X and Y is shown for the purposes of clarity only.

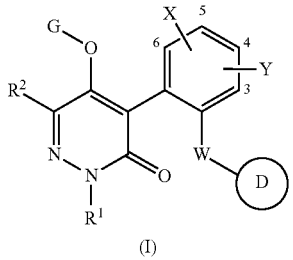

(I)

| Compound | R$^1$ | R$^2$ | G | X | Y | W | D | NMR details |
|---|---|---|---|---|---|---|---|---|
| 1.001 | —Me | —Me | —H | 6-F | 3-Cl | —CH$_2$—CH$_2$— | —Ph | $^1$H NMR (DMSO-d6) δ$_H$: 10.85 (s, 1H), 7.57-7.53 (m, 1H), 7.27-7.15 (m, 4H), 7.0 (d, J = 7.2, 2H), 3.60 (s, 3H), 2.73-2.50 (m, 4H), 2.25 (s, 3H). |
| 1.002 | —Me | —Me | —H | 6-F | 3-Cl | (E)—CH=CH— | —Ph | $^1$H NMR (DMSO-d6) δ$_H$: 10.8 (s, 1H), 7.62 (m, 1H), 7.37-7.24 (m, 6H) 6.94 (d, J = 16.5, 1H), 6.57 (d, J = 16.5, 1H), 6.53 (s, 3H), 2.18 (s, 3H). |
| 1.012 | —Me | —Me | —H | 6-F | 3-Cl | —CH$_2$—CH$_2$— | 4-chloro-phenyl- | $^1$H NMR (400 MHz, chloroform) δ = 7.51-7.44 (m, 1H), 7.21-7.15 (m, 2H), 7.07-6.98 (m, 1H), 6.93 (d, J = 8.4 Hz, 2H), 5.43-5.18 (m, 1H), 3.76 (s, 3H), 2.86-2.67 (m, 4H), 2.31 (s, 3H). |
| 1.018 | —Me | —Me | —H | 6-F | 3-Cl | —CH$_2$—CH$_2$— | 6-trifluoromethyl-phenyl- | $^1$H NMR (400 MHz, CDCl$_3$) δ ppm 2.29 (d, J = 4.16 Hz, 3 H) 2.70-2.93 (m, 4 H) 3.65-3.81 (m, 3 H) 6.95-7.06 (m, 1 H) 7.12 (br d, J = 6.48 Hz, 2 H) 7.48 (d, J = 8.07 Hz, 3 H). |
| 1.024 | —Me | —Me | —H | 6-F | 3-Cl | —CH$_2$—CH$_2$— | 4-cyano-phenyl- | $^1$H NMR (400 MHz, CDCl3) δ ppm 7.46-7.51 (m, 2 H) 7.26-7.31 (m, 1 H) 7.08 (d, J = 8.19 Hz, 2 H) 6.86 (t, J = 8.50 Hz, 1 H) 3.63 (s, 3 H) 2.61-2.77 (m, 4 H) 2.24 (s, 3 H). |
| 1.042 | —Me | —Me | —H | 6-F | 3-Cl | —CH$_2$—CH$_2$— | 4-trifluoromethyl-3-pyridyl- | $^1$H NMR (400 MHz, CDCl$_3$) δ = 8.30 (s, 1H), 7.54 (d, J = 1.2, 2H), 7.37 (dd, J = 8.8 and 5.1, 1H), 6.95 (t, J = 8.5, 1H), 3.69 (s, 3H), 2.92-2.65 (m, 4H), 2.28 (s, 3H). |
| 1.048 | —Me | —Me | —H | 6-F | 3-Cl | —CH$_2$—CH$_2$— | 4-fluoro-phenyl- | $^1$H NMR (400 MHz, CDCl$_3$) δ ppm 7.44 (dd, 1H), 7.01-6.88 (m, 5H), 5.91 (br s, 1H), 3.73 (s, 3H), 2.81-2.65 (m, 4H), 2.30 (s, 3H). |
| 1.054 | —Me | —Me | —H | 6-F | 3-Cl | —CH$_2$—CH$_2$— | 3-pyridyl | $^1$H NMR (400 MHz, DMSO-d6) δ ppm 2.26 (s, 3 H) 2.58-2.82 (m, 4 H) 3.61 (s, 3 H) 7.22 (t, J = 8.80 Hz, 1 H) 7.26-7.32 (m, 1 H) 7.46 (dt, J = 7.79, 1.79 Hz, 1 H) 7.43-7.49 (m, 1 H) 7.53 (dd, J = 8.86, 5.20 Hz, 1 H) 8.24 (s, 1 H) 8.40 (br d, J = 3.79 Hz, 1 H). |

TABLE 4-continued

Preparation examples of compounds of formula (I). The numbering system used to describe the positions of X and Y is shown for the purposes of clarity only.

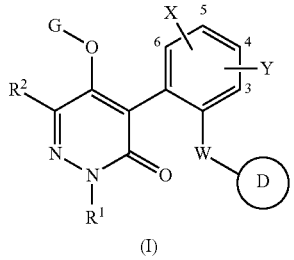

(I)

| Compound | R¹ | R² | G | X | Y | W | D | NMR details |
|---|---|---|---|---|---|---|---|---|
| 1.060 | —Me | —Me | —H | 6-F | 3-Cl | —CH₂—CH₂— | 3,4-difluoro-phenyl- | ¹H NMR (400 MHz, CDCl₃) δ = 7.44 (dd, J = 5.2, 8.6 Hz, 1H), 7.04-6.95 (m, 2H), 6.86-6.77 (m, 1H), 6.77-6.63 (m, 1H), 3.78-3.70 (m, 3H), 2.83-2.64 (m, 4H), 2.31 (s, 3H). |
| 1.066 | —Me | —Me | —H | 6-F | 3-Cl | —CH₂—CH₂— | 2-trifluoromethyl-phenyl- | ¹H NMR (400 MHz, CDCl₃) δ = 7.53 (br. d, J = 7.5 Hz, 1H), 7.43 (br. t, J = 7.5 Hz, 1H), 7.33 (dd, J = 5.1, 8.5 Hz, 1H), 7.29-7.22 (m, 2H), 6.89 (t, J = 8.5 Hz, 1H), 3.65 (s, 3H), 2.83-2.65 (m, 4H), 2.26 (s, 3H). |
| 1.089 | —Me | —Me | —(C=O)ⁱPr | 6-F | 3-Cl | —CH₂—CH₂— | 4-chloro-phenyl- | ¹H NMR (400 MHz, CDCl₃) δ = 7.41 (dd, J = 5.1, 8.9 Hz, 1H), 7.23-7.18 (m, 2H), 7.07-7.03 (m, 2H), 6.98 (t, J = 8.6 Hz, 1H), 3.83 (s, 3H), 2.86-2.67 (m, 4H), 2.54 (m, 1H), 2.24 (s, 3H), 0.97 (d, J = 7.0 Hz, 3H), 0.96 (d, J = 7.0 Hz, 3H). |
| 1.095 | —Me | —Me | —(C=O)ⁱPr | 6-F | 3-Cl | —CH₂—CH₂— | 4-trifluoromethyl-phenyl- | ¹H NMR (400 MHz, CDCl₃) δ_H = 7.50 (d, J = 8.0, 2H), 7.43 (dd, J = 8.9 & 5.1, 1H), 7.24 (d, J = 8.0, 2H), 7.00 (t, J = 8.6, 1H), 3.84 (s, 3H), 2.99-2.80 (m, 3H), 2.73 (dd, J = 11.0 & 6.2, 1H), 2.54 (hep, J = 7.0, 1H), 2.25 (s, 3H), 0.98 (d, J = 7.0, 3H), 0.95 (d, J = 7.0, 3H). |
| 1.125 | —Me | —Me | —(C=O)ⁱPr | 6-F | 3-Cl | —CH₂—CH₂— | 4-fluoro-phenyl- | ¹H NMR (400 MHz, CDCl₃) δ = 7.42 (dd, 1H), 7.11-7.06 (m, 2H), 6.99 (t, 1H), 6.97-6.90 (m, 2H), 3.84 (s, 3H), 2.86-2.68 (m, 4H), 2.55 (sept, 1H), 2.26 (s, 3H), 0.98 (dd, 6H). |
| 1.149 | —Me | —Me | —(C=O)ⁱPr | 6-F | 3-Cl | —CH₂—CH₂— | p-tolyl- | ¹H NMR (400 MHz, CDCl₃) δ = 7.41 (dd, J = 8.8 & 5.1, 1H), 7.10-6.92 (m, 5H), 3.83 (s, 3H), 2.86-2.68 (m, 4H), 2.54 (sep, J = 7.0, 1H), 2.31 (s, 3H), 2.24 (s, 3H), 0.96 (d, J = 7.0, 6H). |

Biological Efficacy for Compounds of Formula (I)

B1 Post-Emergence Efficacy—Test 1

Seeds of a variety of test species are sown in standard soil in pots:—*Solanum nigrum* (SOLNI), *Amaranthus retoflexus* (AMARE), *Setaria faberi* (SETFA), *Alopecurus myosuroides* (ALOMY), *Echinochloa crus-galli* (ECHCG), *Ipomoea hederacea* (IPOHE), *Lolium perenne* (LOLPE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethylene sorbitan monolaurate, CAS RN 9005-64-5). Compounds are applied at 1000 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are assessed on a five point scale (5=80-100%; 4=60-79%; 3=40-59%; 2=20-39%; 1=0-19%). Results are shown in Table 5 below. A blank value in the table is indicative that the compound was not tested on that species.

TABLE 5

Control of weed species by compounds of formula (I) after post-emergence application

| Compound | AMARE | SOLNI | SETFA | LOLPE | ECHCG | IPOHE |
|---|---|---|---|---|---|---|
| 1.001 | 5 | 5 | 5 | 5 | 5 | 5 |
| 1.002 | 4 | 5 | 3 | 4 | 4 | 5 |
| 1.012 | 5 | 5 | 5 | 5 | 5 | 5 |
| 1.018 | 5 | 5 | 5 | 5 | 5 | 5 |
| 1.024 | 5 | 5 | 5 | 5 | 5 | 5 |
| 1.042 | 5 | 5 | 5 | 5 | 5 | 5 |
| 1.048 | 5 | 5 | 5 | 5 | 5 | 5 |
| 1.054 | 5 | 5 | 5 | 5 | 5 | 5 |
| 1.060 | 5 | 5 | 5 | 5 | 5 | 5 |
| 1.066 | 5 | 5 | 5 | 4 | 5 | 5 |
| 1.089 | 5 | 5 | 5 | 5 | 5 | 5 |
| 1.095 | 5 | 5 |   | 5 | 5 | 5 |
| 1.125 | 5 | 5 | 5 | 5 | 5 | 5 |
| 1.149 | 5 | 5 | 5 | 5 | 5 | 5 |

B2 Post-Emergence Efficacy—Test 2

Seeds of a variety of test species (see Table B1) were sown in standard soil in pots. After cultivation for 12 days (post-emergence) under controlled conditions in a glasshouse (at 24/18° C. or 20/16° C., at day/night; 16 hours light; 65% humidity), the plants were sprayed with an aqueous spray solution derived from the formulation of the technical active ingredient dissolved in IF50 (see Table B2 for composition) and adjuvant (Genapol XO80) was added to the spray solution at a rate of 0.2% v/v.

TABLE B1

Plant species under test and abbreviations used

|  | Abbreviation |
|---|---|
| Cool climate plant species: |  |
| *Hordeum vulgare* | HORVW |
| *Triticum aestivum* | TRZAW |
| *Brassica napus* | BRSNN |
| *Beta vulgaris* | BEAVA |
| *Alopecurus myosuroides* | ALOMY |
| *Avena fatua* | AVEFA |
| *Bromus tectorum* | BROTE |

TABLE B1-continued

Plant species under test and abbreviations used

|  | Abbreviation |
|---|---|
| *Lolium perenne* | LOLPE |
| *Poa annua* | POAAN |
| *Chenopodium album* | CHEAL |
| *Galium aparine* | GALAP |
| *Kochia scoparia* | KSHSC |
| *Polygonum convolvulus* | POLCO |
| *Sinapis arvensis* | SINAR |
| *Stellaria media* | STEME |
| *Veronica persica* | VERPE |
| Warm climate species: |  |
| *Orysa sativa* | ORYSA |
| *Zea mays* | ZEAMX |
| *Glycine max* | GLXMA |
| *Brachiaria plantaginea* | BRAPL |
| *Digitaria sanguinalis* | DIGSA |
| *Echinochloa crus galli* | ECHCG |
| *Eleisine indica* | ELEIN |
| *Panicum miliaceum* | PANMI |
| *Setaria faberi* | SETFA |
| *Sorghum bicolour* | SORVU |
| *Abutilon theophrasti* | ABUTH |
| *Amaranthus retroflexus* | AMARE |
| *Bidens pilosa* | BIDPI |
| *Euphorbia hetrophylla* | EPHHL |
| *Ipomoea hederacea* | IPOHE |
| *Sida spinosa* | SIDSP |
| *Xanthium strumarium* | XANST |
| *Cyperus esculentus* | CYPES |

TABLE B2

Chemical composition of IF50

| Component | Chemical description | Function | CAS Registry number | Amount (% w/w) |
|---|---|---|---|---|
| Emulsogen EL360 ™ | Castor oil ethoxylate | Emulsifier | 61791-12-6 | 11.12 |
| N-methyl-pyrrolidone | 1-Methyl-2-pyrrolidone | Solvent | 872-50-4 | 44.44 |
| Dowanol DPM glycol ether | Dipropylene glycol mono-methyl ether | Solvent | 34590-94-8 | 44.44 |

After application, the test plants were grown in a glasshouse under controlled conditions (as above) and watered twice daily. Herbicidal activity was evaluated 15 days after application on a 0-100 scale. The results, where 0=no damage to test plant and 100=total kill of test plant are shown below in Tables 6 to 9.

TABLE 6

Control of warm season plant species by compounds of Formula (I) after post-emergence application

| Compound ID | Rate (g/Ha) | ZEAMX | GLXMA | ORYSA | SETFA | PANMI | SORVU | DIGSA | ECHCG | BRAPL | ELEIN |
|---|---|---|---|---|---|---|---|---|---|---|---|
| 1.024 | 500 | 100 | 100 | 40 | 100 | 100 | 100 | 90 | 100 | 90 | 80 |
| | 250 | 70 | 100 | 20 | 90 | 90 | 90 | 90 | 90 | 70 | 80 |
| | 125 | 40 | 90 | 0 | 90 | 90 | 80 | 80 | 90 | 70 | 60 |
| | 60 | 20 | 90 | 0 | 80 | 80 | 70 | 40 | 80 | 70 | 40 |
| | 30 | 10 | 80 | 0 | 70 | 70 | 10 | 20 | 80 | 60 | 40 |
| | 15 | 0 | 70 | 0 | 20 | 0 | 0 | 0 | 70 | 30 | 0 |
| 1.042 | 500 | 90 | 100 | 50 | 100 | 100 | 100 | 90 | 100 | 90 | 90 |
| | 250 | 70 | 100 | 20 | 90 | 100 | 90 | 80 | 100 | 90 | 80 |
| | 125 | 60 | 90 | 0 | 90 | 90 | 90 | 70 | 90 | 90 | 80 |
| | 60 | 20 | 90 | 0 | 90 | 80 | 80 | 70 | 90 | 90 | 70 |
| | 30 | 10 | 80 | 0 | 80 | 60 | 70 | 60 | 90 | 80 | 70 |
| | 15 | 0 | 60 | 0 | 40 | 10 | 0 | 0 | 80 | 80 | 0 |
| 1.048 | 500 | 100 | 100 | 30 | 100 | 100 | 90 | 70 | 100 | 100 | 80 |
| | 250 | 70 | 90 | 10 | 80 | 100 | 80 | 50 | 90 | 90 | 80 |
| | 125 | 50 | 90 | 0 | 70 | 80 | 70 | 20 | 90 | 80 | 60 |
| | 60 | 50 | 90 | 0 | 40 | 30 | 70 | 20 | 80 | 80 | 60 |
| | 30 | 10 | 80 | 0 | 40 | 20 | 30 | 10 | 80 | 60 | 50 |
| | 15 | 0 | 70 | 0 | 0 | 0 | 0 | 0 | 60 | 20 | 0 |
| 1.066 | 500 | 70 | 90 | 40 | 90 | 100 | 100 | 70 | 90 | 100 | 80 |
| | 250 | 30 | 90 | 20 | 90 | 100 | 90 | 70 | 90 | 70 | 70 |
| | 125 | 20 | 70 | 10 | 80 | 80 | 80 | 40 | 90 | 80 | 70 |
| | 60 | 20 | 70 | 0 | 70 | 60 | 60 | 20 | 90 | — | 70 |
| | 30 | 20 | 40 | 0 | 70 | 50 | 20 | 20 | 80 | 60 | 20 |
| | 15 | 0 | 20 | 0 | 0 | 0 | 0 | 0 | 20 | 0 | 0 |
| 1.089 | 500 | 100 | 100 | 50 | 80 | 90 | 90 | 30 | 100 | 90 | 90 |
| | 250 | 90 | 100 | 20 | 60 | 80 | 90 | 40 | 90 | 90 | 90 |
| | 125 | 30 | — | 10 | 60 | 60 | 90 | 10 | 90 | — | 80 |
| | 60 | 30 | 80 | 0 | 30 | 50 | 70 | 0 | 80 | — | 70 |
| | 30 | 20 | 70 | 0 | 20 | 20 | 60 | 0 | 80 | 90 | 0 |
| | 15 | 0 | — | 0 | 0 | 0 | 0 | 0 | 80 | 80 | 0 |
| 1.125 | 500 | 70 | 90 | 0 | 100 | 80 | 90 | 70 | 100 | 80 | 80 |
| | 250 | 40 | 90 | 0 | 20 | 70 | 80 | 30 | 90 | 70 | 80 |
| | 125 | 20 | — | 0 | 20 | 50 | 70 | 10 | 80 | 80 | 70 |
| 1.125 | 60 | 30 | 70 | 0 | 20 | 50 | 50 | 0 | 80 | 80 | 70 |
| | 30 | 20 | 70 | 0 | 10 | 30 | 50 | 0 | 80 | — | 40 |
| | 15 | 0 | 40 | 0 | 0 | 20 | 0 | 0 | 70 | 80 | 40 |

TABLE 7

Control of warm season plant species by compounds of Formula (I) after post-emergence application

| Compound ID | Rate (g/Ha) | ZEAMX | GLXMA | ORYSA | EPHHL | SIDSP | ABUTH | XANST | IPOHE | BIDPI | AMARE |
|---|---|---|---|---|---|---|---|---|---|---|---|
| 1.024 | 500 | 100 | 100 | 40 | 100 | 100 | 100 | 100 | 100 | 90 | 100 |
| | 250 | 70 | 100 | 20 | 100 | 100 | 100 | — | 100 | 80 | 100 |
| | 125 | 40 | 90 | 0 | 90 | 100 | 100 | 80 | 100 | 80 | 100 |
| | 60 | 20 | 90 | 0 | 90 | 90 | 100 | 80 | 100 | 80 | 90 |
| | 30 | 10 | 80 | 0 | 90 | 90 | 90 | — | 100 | 80 | 90 |
| | 15 | 0 | 70 | 0 | 70 | 80 | 90 | — | — | 80 | 80 |
| 1.042 | 500 | 90 | 100 | 50 | 100 | 100 | 100 | 100 | 100 | 90 | 100 |
| | 250 | 70 | 100 | 20 | 100 | 100 | 100 | 100 | 100 | 80 | 100 |
| | 125 | 60 | 90 | 0 | 100 | — | 100 | 90 | 100 | 70 | 100 |
| | 60 | 20 | 90 | 0 | 90 | 100 | 100 | — | 100 | 70 | 100 |
| | 30 | 10 | 80 | 0 | 90 | 90 | 90 | — | 100 | 70 | 100 |
| | 15 | 0 | 60 | 0 | 80 | 90 | 80 | 80 | 100 | 70 | — |
| 1.048 | 500 | 100 | 100 | 30 | 100 | 90 | 100 | 100 | 100 | 100 | 100 |
| | 250 | 70 | 90 | 10 | 100 | 90 | 90 | 90 | 100 | 100 | 100 |
| | 125 | 50 | 90 | 0 | 90 | 90 | 90 | 90 | 100 | 70 | 90 |
| | 60 | 50 | 90 | 0 | 90 | 80 | 90 | 90 | 100 | 70 | 90 |
| | 30 | 10 | 80 | 0 | 70 | 80 | 80 | — | 80 | 70 | 80 |
| | 15 | 0 | 70 | 0 | 50 | 80 | 60 | — | 70 | 70 | 60 |
| 1.066 | 500 | 70 | 90 | 40 | 100 | 100 | 100 | 100 | 100 | 90 | 100 |
| | 250 | 30 | 90 | 20 | 100 | 90 | 90 | 100 | 100 | 90 | 100 |
| | 125 | 20 | 70 | 10 | 90 | 90 | 90 | — | 100 | 80 | 100 |
| | 60 | 20 | 70 | 0 | 80 | 80 | 50 | 90 | 90 | 70 | 90 |
| | 30 | 20 | 40 | 0 | 70 | 80 | 50 | — | 90 | 60 | 90 |
| | 15 | 0 | 20 | 0 | 60 | 40 | 20 | — | 70 | 50 | 90 |

TABLE 7-continued

Control of warm season plant species by compounds of Formula (I) after post-emergence application

| Compound ID | Rate (g/Ha) | Warm Season Plant Species | | | | | | | | | |
|---|---|---|---|---|---|---|---|---|---|---|---|
| | | ZEAMX | GLXMA | ORYSA | EPHHL | SIDSP | ABUTH | XANST | IPOHE | BIDPI | AMARE |
| 1.089 | 500 | 100 | 100 | 50 | 100 | 100 | 100 | 100 | 100 | 100 | 100 |
| | 250 | 90 | 100 | 20 | 100 | 100 | 100 | 90 | 100 | 80 | 100 |
| | 125 | 30 | — | 10 | 100 | 100 | 100 | 90 | 100 | 80 | 100 |
| | 60 | 30 | 80 | 0 | 100 | 90 | 100 | 80 | 100 | 70 | 90 |
| | 30 | 20 | 70 | 0 | 100 | 80 | 90 | 90 | 100 | 60 | 80 |
| | 15 | 0 | — | 0 | 80 | — | 70 | — | 100 | 70 | 80 |
| 1.125 | 500 | 70 | 90 | 0 | 100 | 100 | 100 | 100 | 100 | 100 | 100 |
| | 250 | 40 | 90 | 0 | 100 | 90 | 100 | 90 | 100 | 80 | 100 |
| | 125 | 20 | — | 0 | 100 | 90 | 90 | 90 | 100 | 70 | 100 |
| | 60 | 30 | 70 | 0 | 100 | 80 | 90 | 90 | 100 | 70 | 90 |
| | 30 | 20 | 70 | 0 | 90 | — | 90 | 90 | 100 | 60 | 90 |
| | 15 | 0 | 40 | 0 | 90 | — | 80 | — | 90 | 60 | 80 |

TABLE 8

Control of cool season plant species by compounds of Formula (I) after post-emergence application

| Compound ID | Rate (g/Ha) | Cool Season Plant Species | | | | | | | | | |
|---|---|---|---|---|---|---|---|---|---|---|---|
| | | HORVW | TRZAW | BRSNN | BEAVA | ALOMY | AVEFA | BROTE | LOLPE | POAAN | CHEAL |
| 1.024 | 500 | 20 | 70 | 90 | 100 | 70 | 80 | 70 | 90 | 90 | 100 |
| | 250 | 10 | 60 | 90 | 80 | 70 | 70 | 40 | 90 | 80 | 90 |
| | 125 | 10 | 30 | 90 | 80 | 70 | 60 | 20 | 90 | 80 | 90 |
| | 60 | 10 | 20 | 90 | 80 | 50 | 30 | 10 | 70 | 30 | 90 |
| | 30 | 10 | 0 | 90 | 70 | 30 | 20 | 0 | 70 | 20 | 90 |
| | 15 | 0 | 0 | 80 | 70 | 10 | 10 | 0 | 10 | 10 | 60 |
| 1.042 | 500 | 80 | 80 | 90 | 90 | 90 | 90 | 90 | 90 | 90 | 100 |
| | 250 | 80 | 80 | 90 | 90 | 90 | 90 | 80 | 90 | 90 | 100 |
| | 125 | 40 | 70 | 90 | 90 | 80 | 80 | 80 | 90 | 90 | 90 |
| | 60 | 20 | 60 | 90 | 80 | 80 | 80 | 70 | 70 | 80 | 90 |
| | 30 | 20 | 30 | 90 | 70 | 60 | 60 | 30 | 70 | 70 | 90 |
| | 15 | 10 | 20 | 90 | 80 | 20 | 30 | 20 | 60 | 20 | — |
| 1.048 | 500 | 80 | 80 | 90 | 90 | 90 | 90 | 70 | 90 | 90 | 100 |
| | 250 | 40 | 50 | 90 | 90 | 80 | 90 | 60 | 90 | 90 | 90 |
| | 125 | 40 | 20 | 90 | 90 | 80 | 80 | 50 | 90 | 80 | 70 |
| | 60 | 10 | 20 | 90 | 80 | 70 | 60 | 20 | 90 | 80 | — |
| | 30 | 10 | 10 | 90 | 80 | 30 | 30 | 10 | 40 | 30 | — |
| | 15 | 10 | 0 | 90 | 70 | 20 | 10 | 0 | 20 | 30 | — |
| 1.066 | 500 | 90 | 80 | 90 | 90 | 90 | 90 | 90 | 100 | 90 | 100 |
| | 250 | 80 | 70 | 90 | 80 | 90 | 90 | 80 | 90 | 90 | 100 |
| | 125 | 70 | 60 | 90 | 80 | 80 | 90 | 70 | 90 | 90 | 90 |
| | 60 | 20 | 40 | 90 | 80 | 70 | 40 | 60 | 80 | 80 | 90 |
| | 30 | 10 | 10 | 90 | 80 | 50 | 20 | 20 | 20 | 70 | 90 |
| | 15 | 0 | 0 | 90 | 80 | 20 | 0 | 0 | 10 | 20 | — |
| 1.089 | 500 | 60 | 70 | 90 | 90 | 90 | 90 | 70 | 90 | 70 | 100 |
| | 250 | 30 | 60 | 90 | 90 | 80 | 90 | 60 | 90 | 80 | 100 |
| | 125 | 20 | 30 | 90 | 80 | 80 | 80 | 30 | 90 | 90 | 100 |
| | 60 | 20 | 20 | 90 | 80 | 50 | 70 | 10 | 80 | 70 | 90 |
| | 30 | 10 | 0 | 80 | 80 | 50 | 70 | 0 | 70 | 40 | 90 |
| | 15 | 10 | 0 | 80 | 90 | 20 | 30 | 0 | 40 | 20 | 80 |
| 1.125 | 500 | 10 | 50 | 90 | 70 | 40 | 80 | 10 | 90 | 60 | 90 |
| | 250 | 10 | 30 | 90 | 70 | 60 | 70 | 10 | 80 | 70 | 90 |
| | 125 | 10 | 20 | 90 | 70 | 30 | 70 | 0 | 70 | 60 | 90 |
| | 60 | 10 | 10 | 80 | 60 | 30 | 60 | 0 | 60 | 20 | 90 |
| | 30 | 0 | 10 | 80 | 60 | 10 | 40 | 0 | 50 | 10 | 90 |
| | 15 | 0 | 0 | 80 | 70 | 10 | 30 | 0 | 40 | 0 | 90 |

TABLE 9

Control of cool season plant species by compounds of Formula (I) after post-emergence application

| Compound ID | Rate (g/Ha) | HORVW | TRZAW | POLCO | KCHSC | SINAR | STEME | GALAP | VERPE |
|---|---|---|---|---|---|---|---|---|---|
| 1.024 | 500 | 20 | 70 | 100 | 20 | 100 | 100 | 90 | 100 |
|  | 250 | 10 | 60 | 90 | 10 | 90 | 90 | 90 | 100 |
|  | 125 | 10 | 30 | 90 | 10 | — | 90 | 60 | 80 |
|  | 60 | 10 | 20 | 90 | 0 | 80 | 90 | 20 | 90 |
|  | 30 | 10 | 0 | — | 0 | 80 | 90 | 20 | 80 |
|  | 15 | 0 | 0 | 80 | 0 | 80 | 90 | — | 80 |
| 1.042 | 500 | 80 | 80 | 100 | 60 | 90 | 100 | 90 | 100 |
|  | 250 | 80 | 80 | 90 | 30 | 90 | 100 | 80 | 100 |
|  | 125 | 40 | 70 | 90 | 20 | 90 | 100 | 80 | 100 |
|  | 60 | 20 | 60 | 90 | 10 | 90 | 90 | 60 | 100 |
|  | 30 | 20 | 30 | 80 | 10 | 90 | 100 | 30 | 90 |
|  | 15 | 10 | 20 | 80 | 0 | 80 | 100 | 10 | 80 |
| 1.048 | 500 | 80 | 80 | 90 | 80 | 90 | 100 | 80 | 100 |
|  | 250 | 40 | 50 | 90 | 50 | 90 | 100 | 60 | 100 |
|  | 125 | 40 | 20 | 90 | 20 | 90 | 100 | 60 | 80 |
|  | 60 | 10 | 20 | 90 | 10 | 80 | 90 | 50 | 90 |
|  | 30 | 10 | 10 | 70 | 0 | 80 | 90 | 30 | 80 |
|  | 15 | 10 | 0 | 60 | 0 | 40 | 90 | 20 | 60 |
| 1.066 | 500 | 90 | 80 | 100 | 20 | 90 | 100 | 90 | 100 |
|  | 250 | 80 | 70 | 100 | 20 | 90 | 90 | 30 | 100 |
|  | 125 | 70 | 60 | 90 | 10 | 90 | 90 | 20 | 100 |
|  | 60 | 20 | 40 | 90 | 0 | 80 | 90 | 20 | 100 |
|  | 30 | 10 | 10 | 80 | 0 | 60 | 60 | 20 | 90 |
|  | 15 | 0 | 0 | 70 | 0 | 60 | 80 | 20 | 80 |
| 1.089 | 500 | 60 | 70 | — | 60 | 90 | 90 | 90 | 100 |
|  | 250 | 30 | 60 | — | 60 | 90 | 90 | 30 | 100 |
|  | 125 | 20 | 30 | — | 60 | 90 | 90 | 30 | 90 |
|  | 60 | 20 | 20 | — | 50 | 90 | 90 | — | 90 |
|  | 30 | 10 | 0 | — | 20 | 80 | 90 | 20 | 80 |
|  | 15 | 10 | 0 | — | 10 | 70 | 90 | 10 | 70 |
| 1.125 | 500 | 10 | 50 | 90 | 70 | 90 | 90 | 70 | 90 |
|  | 250 | 10 | 30 | 90 | 60 | 90 | 90 | 40 | 80 |
|  | 125 | 10 | 20 | 90 | 50 | 90 | 90 | 30 | 80 |
|  | 60 | 10 | 10 | 90 | 30 | 80 | 90 | 20 | 70 |
|  | 30 | 0 | 10 | 90 | 20 | 60 | 90 | 20 | 70 |
|  | 15 | 0 | 0 | 90 | 0 | 60 | 90 | — | 70 |

The invention claimed is:

1. A composition comprising:
(A) a compound of formula (I)

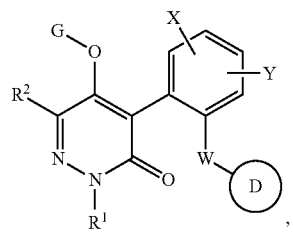

or a salt or N-oxide thereof, wherein $R^1$ is selected from the group consisting of $C_1$-$C_4$ alkyl, $C_3$-$C_6$cycloalkyl, $C_3$-$C_6$alkoxy, $C_1$-$C_2$ alkoxy-$C_1$-$C_2$ alkyl, $C_2$-$C_4$ alkenyl, $C_1$-$C_4$ haloalkyl, cyano-$C_1$-$C_4$alkyl, $C_2$-$C_4$ haloalkenyl, $C_2$-$C_4$ alkynyl and $C_2$-$C_4$ haloalkynyl;

$R^2$ is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, —S(O)$_m$$C_1$-$C_6$alkyl, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;

G is hydrogen, or C(O)$R^3$;

$R^3$ is selected from the group consisting of $C_1$-$C_6$alkyl, $C_1$-$C_6$alkenyl, $C_1$-$C_6$alkynyl, $C_1$-$C_6$alkyl-S—, —NR$^4$R$^5$ and phenyl optionally substituted by one or more $R^6$;

$R^4$ and $R^5$ are independently selected from the group consisting of $C_1$-$C_6$ alkyl and $C_1$-$C_6$ alkoxy, or $R^4$ and $R^5$ together can form a morpholinyl ring;

$R^6$ is selected from the group consisting of halogen, cyano, nitro, $C_1$-$C_3$alkyl, $C_1$-$C_3$haloalky, $C_1$-$C_3$alkoxy and $C_1$-$C_3$haloalkoxy;

X and Y are each independently hydrogen, $C_1$-$C_3$ alkyl, $C_1$-$C_3$ alkoxy, $C_1$-$C_3$haloalkyl, $C_1$-$C_3$haloalkoxy, or halogen;

D is a substituted or unsubstituted monocyclic heteroaryl ring containing 1, 2, or 3 heteroatoms independently selected from oxygen, nitrogen and sulphur, and wherein when D is substituted it is substituted on at least one ring carbon atom with $R^8$ and/or on a ring nitrogen atom with $R^9$;

each $R^8$ is independently oxygen, hydroxyl, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1-C_6$alkylcarbonyl-, $C_1-C_6$alkyl-S(O)$_m$—, amino, $C_1-C_6$alkylamino, $C_1-C_6$dialkylamino, —C($C_1$-$C_3$alkyl)=N—O—$C_1-C_3$alkyl and $C_2-C_6$ haloalkynyl;

m is an integer of 0, 1, or 2; and each $R^9$ is independently, $C_1-C_4$ alkyl, $C_3-C_6$alkoxy, $C_1-C_2$ alkoxy-$C_1-C_2$ alkyl, $C_2-C_4$ alkenyl, $C_1-C_4$ haloalkyl, $C_2-C_4$ haloalkenyl, $C_2-C_4$ alkynyl or $C_2-C_4$ haloalkynyl; or, D is a substituted or unsubstituted phenyl ring (Dp),

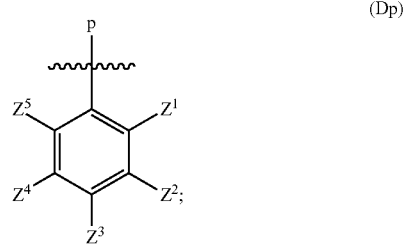

(Dp)

wherein p denotes the point of attachment of (Dp) to the rest of the molecule;

$Z^1$, $Z^2$, $Z^3$, $Z^4$, and $Z^5$ are each independently selected from hydrogen, $C_1-C_3$ alkyl, $C_1-C_3$ alkoxy, $C_1-C_3$haloalkyl, $C_1-C_3$haloalkoxy, or halogen;

and

W is either

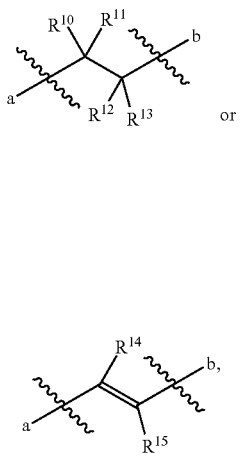

W1

W2 wherein

"a" denotes the point of attachment to the phenyl-pyridazinone/phenyl-pyridazine dione moiety, "b" denotes the point of attachment to ring D, $R^{10}$, $R^{12}$, $R^{14}$ and $R^{15}$ are each independently hydrogen, $C_1-C_3$alkyl, or $C_1-C_3$haloalkyl; or $R^{10}$ and $R^{12}$ together with the carbon atoms to which they are joined form a $C_3-C_6$ carbocyclic ring;

$R^{11}$ and $R^{13}$ are each independently hydrogen, halogen, $C_1-C_3$alkyl, or $C_1-C_3$haloalkyl, provided that when one of $R^{11}$ or $R^{13}$ is halogen, $C_1-C_3$alkyl or $C_1-C_3$ haloalkyl, the other is hydrogen;

and (B) one or more compounds of formula (II)

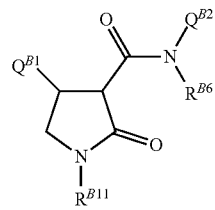

(II)

wherein, $R^{B11}$ is H, $C_1-C_6$alkyl, $C_1-C_6$ haloalkyl or $C_4-C_8$ cycloalkyl;

$R^{B6}$ is H, $C_1-C_6$alkyl, or $C_1-C_6$alkoxy;

$Q^{B1}$ is an optionally substituted ring system, selected from the group consisting of phenyl, thienyl, pyridinyl, benzodioxolyl, naphthyl, naphthalenyl, benzofuranyl, furanyl, benzothiophenyl, and pyrazolyl, wherein when substituted said ring system is substituted by 1 to 3 $RB^4$;

$Q^{B2}$ is an optionally substituted ring system, selected from the group consisting of phenyl, pyridinyl, benzodioxolyl, pyridinone, thiadazolyl, thiazolyl, and oxazolyl, wherein when substituted said ring system is substituted by 1 to 3 $R^{B5}$;

each $R^{B4}$ is independently halogen, $C_1-C_6$alkyl, $C_1-C_6$haloalkyl, $C_1-C_6$alkoxy, $C_1-C_6$haloalkoxy, $C_3-C_8$cycloalkyl, cyano, $C_1-C_6$alkylthio, $C_1-C_6$alkylsulphinyl, $C_1-C_6$alkylsulphonyl, $SF_5$, $NHR^{B8}$, phenyl optionally substituted by 1-3 $R^{B7}$, or pyrazolyl optionally substituted by 1-3 $R^{B7}$;

each $R^{B5}$ is independently halogen, $C_1-C_6$alkyl, $C_1-C_6$haloalkyl, $C_1-C_6$alkoxy, $C_1-C_6$haloalkoxy, cyano, nitro, $C_1-C_6$alkylthio, $C_1-C_6$alkylsulphinyl, or $C_1-C_6$alkylsulphonyl;

each $R^{B7}$ is independently $C_1-C_6$alkyl, halogen, or $C_1-C_6$haloalkyl; and $R^{B8}$ is $C_1-C_4$alkoxycarbonyl; or an N-oxide, or a salt form thereof.

2. The composition of claim 1, wherein W is W1 and each of $R^{10}$, $R^{11}$, $R^{12}$, and $R^{13}$ is hydrogen.

3. The composition of claim 1, wherein W is W2 and each of $R^{14}$ and $R^{15}$ is hydrogen.

4. The composition of claim 1, wherein W is W1, $R^{10}$ and $R^{12}$ together with the carbon atoms to which they are joined form a $C_3$-carbocyclic ring, and $R^{11}$ and $R^{13}$ lie in either the trans or the cis configuration and are both H.

5. The composition of claim 1, wherein component (A) is a compound of formula (I) or a salt or N-oxide thereof, selected from the group consisting of 1.001, 1.002, 1.012, 1.018, 1.024, 1.042, 1.048, 1.054, 1.060, 1.066, 1.089, 1.095, 1.125, and 1.149 as defined in the table below:

| Compound No. | Name | Structure |
|---|---|---|
| 1.001 | 4-[3-chloro-6-fluoro-2-(2-phenylethyl)phenyl]-5-hydroxy-2,6-dimethyl-pyridazin-3-one | 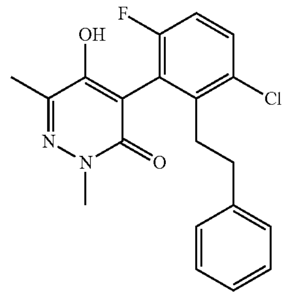 [SMILES: Cc1nn(C)c(=O)c(-c2c(F)ccc(Cl)c2CCc2ccccc2)c1O] |
| 1.002 | 4-[3-chloro-6-fluoro-2-[(E)-styryl]phenyl]-5-hydroxy-2,6-dimethyl-pyridazin-3-one | 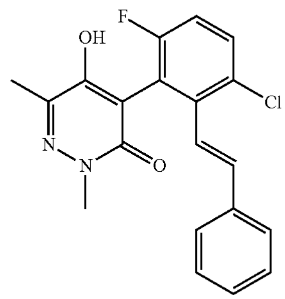 [SMILES: Cc1nn(C)c(=O)c(-c2c(F)ccc(Cl)c2/C=C/c2ccccc2)c1O] |
| 1.012 | 4-[3-chloro-2-[2-(4-chlorophenyl)ethyl]-6-fluoro-phenyl]-5-hydroxy-2,6-dimethyl-pyridazin-3-one | 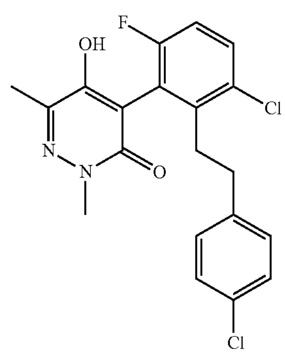 [SMILES: Cc1nn(C)c(=O)c(-c2c(F)ccc(Cl)c2CCc2ccc(Cl)cc2)c1O] |
| 1.018 | 4-[3-chloro-6-fluoro-2-[2-[4-(trifluoromethyl)phenyl]ethyl]phenyl]-5-hydroxy-2,6-dimethyl-pyridazin-3-one | 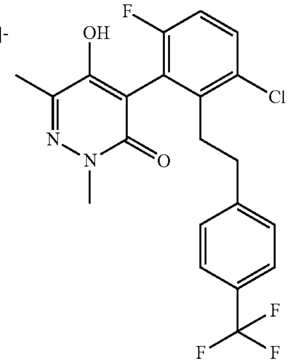 |

-continued
| Compound No. | Name | Structure |
|---|---|---|
| 1.024 | 4-[3-chloro-6-fluoro-2-[2-[4-(cyano)phenyl]ethyl]phenyl]-5-hydroxy-2,6-dimethyl-pyridazin-3-one | 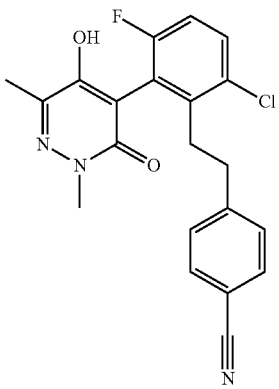 [SMILES: Cc1nn(C)c(=O)c(-c2c(F)ccc(Cl)c2CCc2ccc(C#N)cc2)c1O] |
| 1.042 | 4-[3-chloro-6-fluoro-2-[2-[6-(trifluoromethyl)-3-pyridyl]ethyl]phenyl]-5-hydroxy-2,6-dimethyl-pyridazin-3-one | 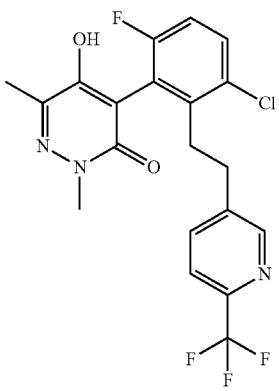 [SMILES: Cc1nn(C)c(=O)c(-c2c(F)ccc(Cl)c2CCc2ccc(C(F)(F)F)nc2)c1O] |
| 1.048 | 4-[3-chloro-6-fluoro-2-[2-(4-fluorophenyl)ethyl]phenyl]-5-hydroxy-2,6-dimethyl-pyridazin-3-one | 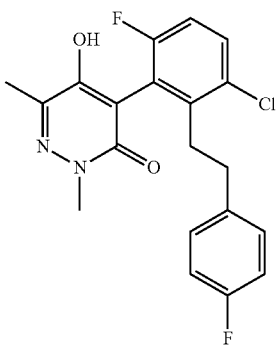 [SMILES: Cc1nn(C)c(=O)c(-c2c(F)ccc(Cl)c2CCc2ccc(F)cc2)c1O] |
| 1.054 | 4-[3-chloro-6-fluoro-2-[2-(3-pyridyl)ethyl]phenyl]-5-hydroxy-2,6-dimethyl-pyridazin-3-one | 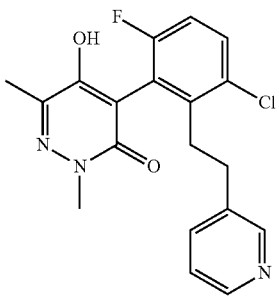 [SMILES: Cc1nn(C)c(=O)c(-c2c(F)ccc(Cl)c2CCc2cccnc2)c1O] |

-continued

| Compound No. | Name | Structure |
|---|---|---|
| 1.060 | 4-[3-chloro-2-[2-(3,4-difluorophenyl)ethyl]-6-fluoro-phenyl]-5-hydroxy-2,6-dimethyl-pyridazin-3-one | 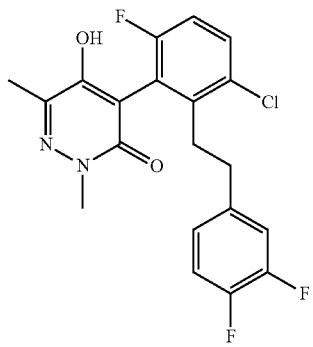 [SMILES: Cc1nn(C)c(=O)c(-c2c(F)ccc(Cl)c2CCc2ccc(F)c(F)c2)c1O] |
| 1.066 | 4-[3-chloro-6-fluoro-2-[2-[2-(trifluoromethyl)phenyl]ethyl]phenyl]-5-hydroxy-2,6-dimethyl-pyridazin-3-one | 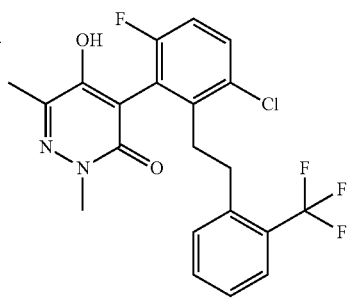 |
| 1.089 | [5-[3-chloro-2-[2-(4-chlorophenyl)ethyl]-6-fluoro-phenyl]-1,3-dimethyl-6-oxo-pyridazin-4-yl] methylpropanoate | 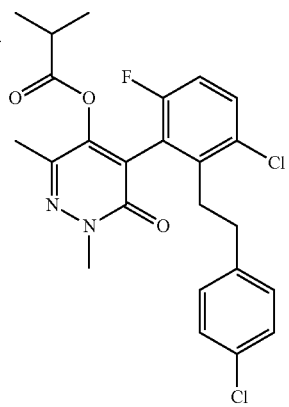 |
| 1.095 | [5-[3-chloro-6-fluoro-2-[2-[4-(trifluoromethyl)phenyl]ethyl]phenyl]-1,3-dimethyl-6-oxo-pyridazin-4-yl] 2-methylpropanoate | 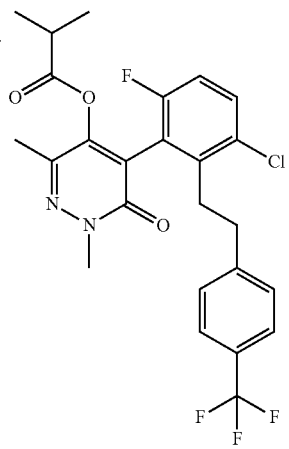 |

-continued

| Compound No. | Name | Structure |
|---|---|---|
| 1.125 | [5-[3-chloro-6-fluoro-2-[2-(4-fluorophenyl)ethyl]phenyl]-1,3-dimethyl-6-oxo-pyridazin-4-yl] 2-methylpropanoate | 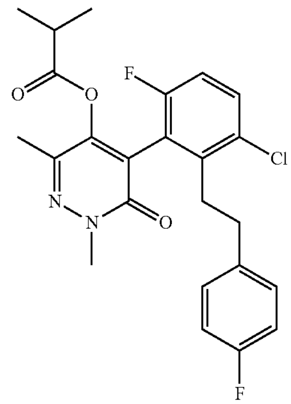 [SMILES: Cc1nn(C)c(=O)c(-c2c(F)ccc(Cl)c2CCc2ccc(F)cc2)c1OC(=O)C(C)C] |
| 1.149 | [5-[3-chloro-6-fluoro-2-[2-(p-tolyl)ethyl]phenyl]-1,3-dimethyl-6-oxo-pyridazin-4-yl] 2-methylpropanoate | 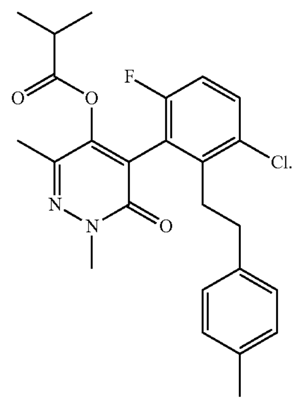 [SMILES: Cc1ccc(CCc2c(Cl)ccc(F)c2-c2c(OC(=O)C(C)C)c(C)nn(C)c2=O)cc1] |

6. The composition of claim 1, wherein component (B) is selected from the group of compounds consisting of 2.1, 2.2, 2.3, 2.4, 2.5, 2.6, 2.7, 2.8, 2.9, 2.10, 2.11, 2.12, 2.13, 2.14, 2.15, 2.16, 2.17, and 2.18, as defined in the table below:

| Compound No. | Name | Structure |
|---|---|---|
| 2.1 | N-(2-fluorophenyl)-2-oxo-4-[3-(trifluoromethyl)phenyl]pyrrolidine-3-carboxamide | 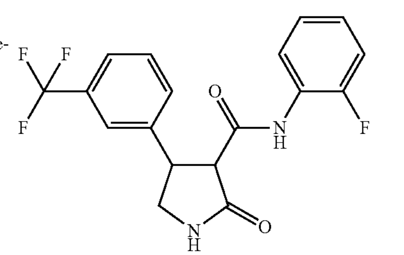 |
| 2.2 | N-(2,3-difluorophenyl)-2-oxo-4-[3-(trifluoromethyl)phenyl]pyrrolidine-3-carboxamide | 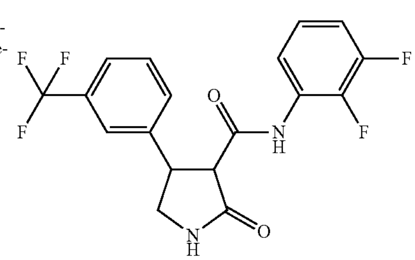 |

-continued

| Compound No. | Name | Structure |
|---|---|---|
| 2.3 | 2-oxo-4-[3-(trifluoromethyl)phenyl]-N-(2,3,4-trifluorophenyl)pyrrolidine-3-carboxamide | 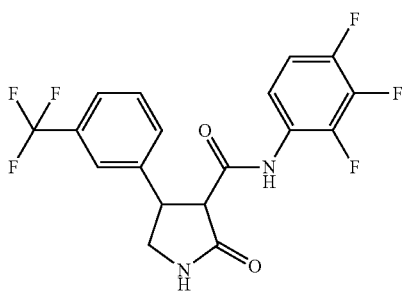 [SMILES: O=C1NCC(c2cccc(C(F)(F)F)c2)C1C(=O)Nc1ccc(F)c(F)c1F] |
| 2.4 | N-(2-fluorophenyl)-1-methyl-2-oxo-4-[3-(trifluoromethyl)phenyl]pyrrolidine-3-carboxamide | 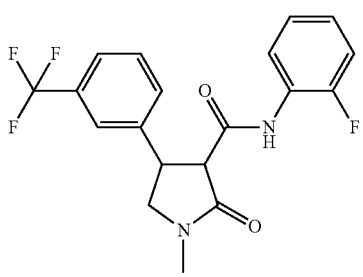 [SMILES: CN1CC(c2cccc(C(F)(F)F)c2)C(C(=O)Nc2ccccc2F)C1=O] |
| 2.5 | N-(2-fluorophenyl)-2-oxo-4-[4-(trifluoromethyl)phenyl]pyrrolidine-3-carboxamide | 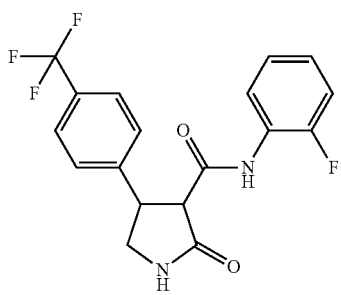 [SMILES: O=C1NCC(c2ccc(C(F)(F)F)cc2)C1C(=O)Nc1ccccc1F] |
| 2.6 | N-(2-fluorophenyl)-1-methyl-2-oxo-4-[4-(trifluoromethyl)phenyl]pyrrolidine-3-carboxamide | 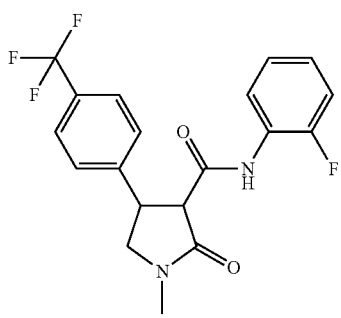 |
| 2.7 | N-(2,3-difluorophenyl)-2-oxo-4-[4-(trifluoromethyl)phenyl]pyrrolidine-3-carboxamide | 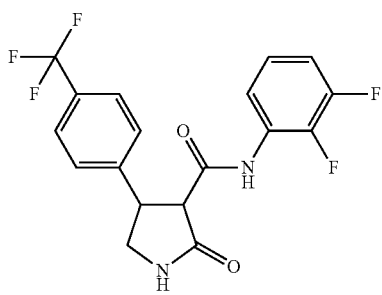 [SMILES: O=C1NCC(c2ccc(C(F)(F)F)cc2)C1C(=O)Nc1cccc(F)c1F] |

-continued

| Compound No. | Name | Structure |
|---|---|---|
| 2.8 | N-(2,3-difluorophenyl)-1-methyl-2-oxo-4-[4-(trifluoromethyl)phenyl]pyrrolidine-3-carboxamide | 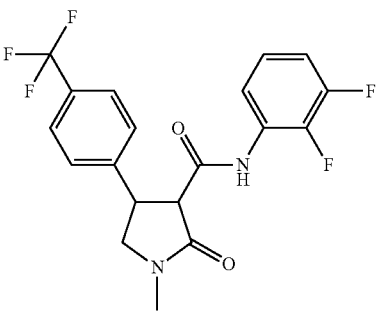 [SMILES: CN1CC(c2ccc(C(F)(F)F)cc2)C(C(=O)Nc2cccc(F)c2F)C1=O] |
| 2.9 | 2-oxo-4-[4-(trifluoromethyl)phenyl]-N-(2,3,4-trifluorophenyl)pyrrolidine-3-carboxamide | 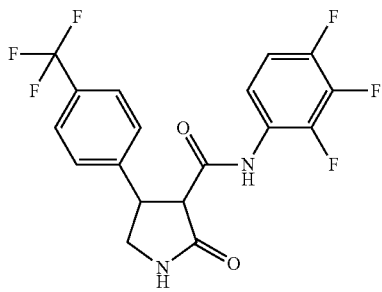 [SMILES: O=C1NCC(c2ccc(C(F)(F)F)cc2)C1C(=O)Nc1ccc(F)c(F)c1F] |
| 2.10 | N-(2-fluorophenyl)-4-(4-fluorophenyl)-1-methyl-2-oxo-pyrrolidine-3-carboxamide | 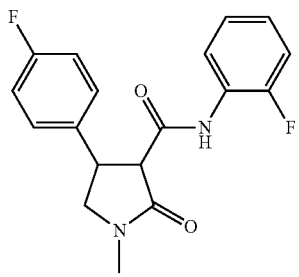 [SMILES: CN1CC(c2ccc(F)cc2)C(C(=O)Nc2ccccc2F)C1=O] |
| 2.11 | N-(2,3-difluorophenyl)-4-(3,4-difluorophenyl)-2-oxo-pyrrolidine-3-carboxamide | 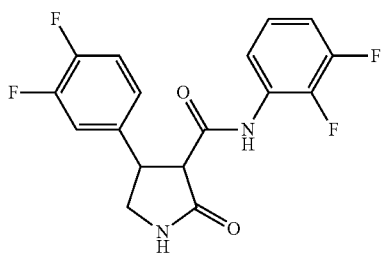 [SMILES: O=C1NCC(c2ccc(F)c(F)c2)C1C(=O)Nc1cccc(F)c1F] |
| 2.12 | 4-(3,4-difluorophenyl)-N-(2-fluorophenyl)-2-oxo-pyrrolidine-3-carboxamide | 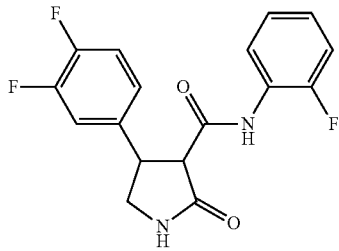 [SMILES: O=C1NCC(c2ccc(F)c(F)c2)C1C(=O)Nc1ccccc1F] |

| Compound No. | Name | Structure |
|---|---|---|
| 2.13 | N-(2,4-difluorophenyl)-4-(3,5-difluorophenyl)-2-oxo-pyrrolidine-3-carboxamide | 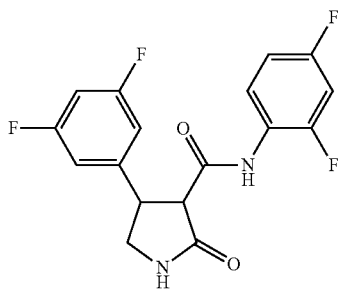 [SMILES: O=C1NCC(c2cc(F)cc(F)c2)C1C(=O)Nc1ccc(F)cc1F] |
| 2.14 | N-(2,3-difluorophenyl)-4-(3-isopropylphenyl)-2-oxo-pyrrolidine-3-carboxamide | 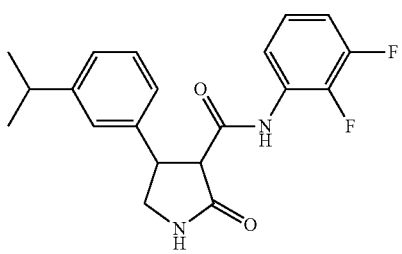 [SMILES: CC(C)c1cccc(C2CNC(=O)C2C(=O)Nc2cccc(F)c2F)c1] |
| 2.15 | N-(2,3-difluorophenyl)-2-oxo-4[6-(trifluoromethyl)-3-pyridyl]pyrrolidine-3-carboxamide | 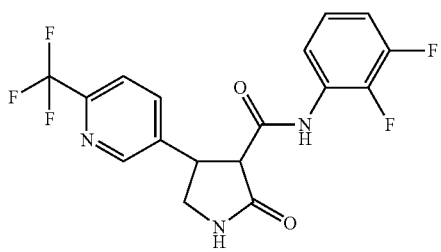 [SMILES: O=C1NCC(c2ccc(C(F)(F)F)nc2)C1C(=O)Nc1cccc(F)c1F] |
| 2.16 | 4-(3,5-difluorophenyl)-N-[3-fluoro-2-(trifluoromethyl)phenyl]-1-methyl-2-oxo-pyrrolidine-3-carboxamide | 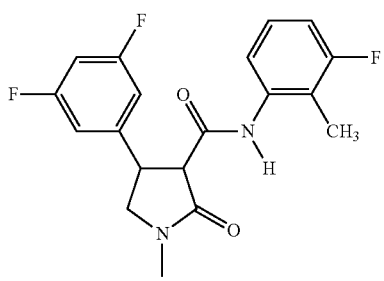 |
| 2.17 | N-(2,4-difluorophenyl)-4-(3,5-difluorophenyl)-1-methyl-2-oxo-pyrrolidine-3-carboxamide | 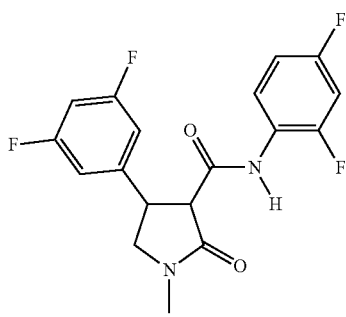 [SMILES: CN1CC(c2cc(F)cc(F)c2)C(C(=O)Nc2ccc(F)cc2F)C1=O] |

-continued

| Compound No. | Name | Structure |
|---|---|---|
| 2.18 | N-(2,3-difluorophenyl)-4-(3,5-difluorophenyl)-1-methyl-2-oxo-pyrrolidine-3-carboxamide | 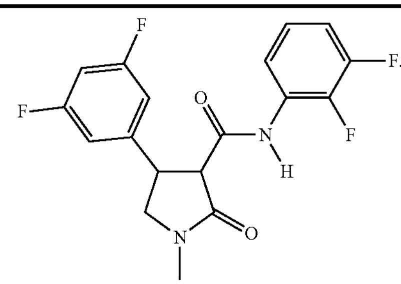 |

7. The composition of claim 1, wherein the weight ratio of component (A) to component (B) is from 0.01:1 to 100:1.

8. The composition of claim 1, wherein the weight ratio of component (A) to component (B) is from 0.05:1 to 20:1.

9. The composition of claim 1, wherein the weight ratio of component (A) to component (B) is from 0.1:1 to 20:1.

10. The herbicidal composition of claim 1, additionally comprising an agriculturally acceptable formulation adjuvant.

11. The herbicidal composition of claim 10, further comprising at least one additional pesticide.

12. The herbicidal composition according to claim 11, wherein the additional pesticide is a herbicide or herbicide safener.

13. A method of controlling unwanted plant growth, comprising applying (A) a compound of formula (I) as defined in claim 1, and (B) a compound of formula (II) as defined in claim 1, to the unwanted plants or to the locus thereof.

14. A method of controlling unwanted plant growth, comprising applying a composition of claim 1.

15. The composition of claim 5, wherein component (B) is selected from the group of compounds consisting of 2.1, 2.2, 2.3, 2.4, 2.5, 2.6, 2.7, 2.8, 2.9, 2.10, 2.11, 2.12, 2.13, 2.14, 2.15, 2.16, 2.17, and 2.18, as defined in the table below:

| Compound No. | Name | Structure |
|---|---|---|
| 2.1 | N-(2-fluorophenyl)-2-oxo-4-[3-(trifluoromethyl)phenyl]pyrrolidine-3-carboxamide | 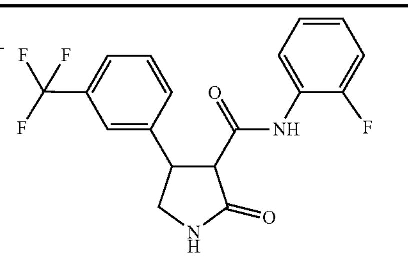 |
| 2.2 | N-(2,3-difluorophenyl)-2-oxo-4-[3-(trifluoromethyl)phenyl]pyrrolidine-3-carboxamide | 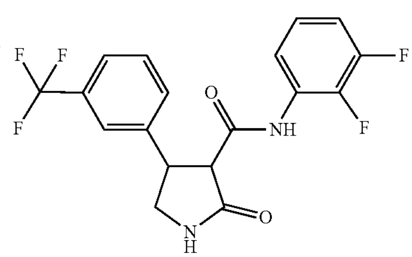 [SMILES: O=C1NCC(c2cccc(C(F)(F)F)c2)C1C(=O)Nc1cccc(F)c1F] |
| 2.3 | 2-oxo-4-[3-(trifluoromethyl)phenyl]-N-(2,3,4-trifluorophenyl)pyrrolidine-3-carboxamide | 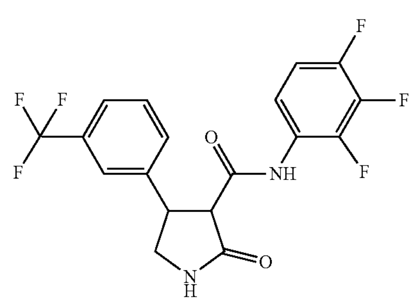 [SMILES: O=C1NCC(c2cccc(C(F)(F)F)c2)C1C(=O)Nc1ccc(F)c(F)c1F] |

-continued

| Compound No. | Name | Structure |
|---|---|---|
| 2.4 | N-(2-fluorophenyl)-1-methyl-2-oxo-4-[3-(trifluoromethyl)phenyl]pyrrolidine-3-carboxamide | 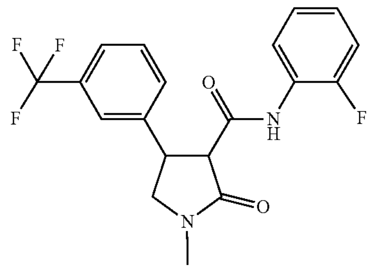 [SMILES: CN1CC(c2cccc(C(F)(F)F)c2)C(C(=O)Nc2ccccc2F)C1=O] |
| 2.5 | N-(2-fluorophenyl)-2-oxo-4-[4-(trifluoromethyl)phenyl]pyrrolidine-3-carboxamide | 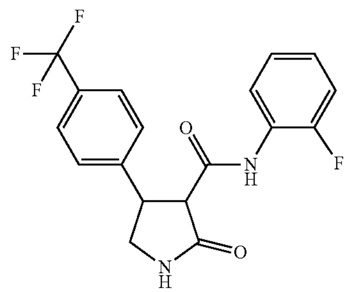 [SMILES: O=C1NCC(c2ccc(C(F)(F)F)cc2)C1C(=O)Nc1ccccc1F] |
| 2.6 | N-(2-fluorophenyl)-1-methyl-2-oxo-4-[4-(trifluoromethyl)phenyl]pyrrolidine-3-carboxamide | 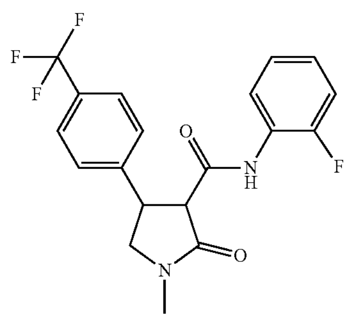 [SMILES: CN1CC(c2ccc(C(F)(F)F)cc2)C(C(=O)Nc2ccccc2F)C1=O] |
| 2.7 | N-(2,3-difluorophenyl)-2-oxo-4-[4-(trifluoromethyl)phenyl]pyrrolidine-3-carboxamide | 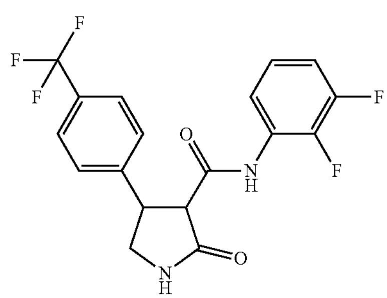 [SMILES: O=C1NCC(c2ccc(C(F)(F)F)cc2)C1C(=O)Nc1cccc(F)c1F] |
| 2.8 | N-(2,3-difluorophenyl)-1-methyl-2-oxo-4-[4-(trifluoromethyl)phenyl]pyrrolidine-3-carboxamide | 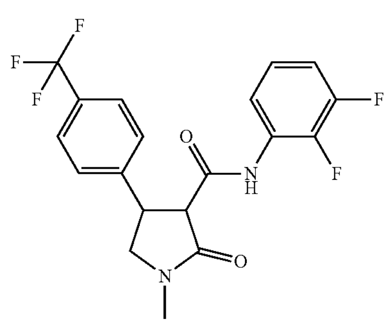 [SMILES: CN1CC(c2ccc(C(F)(F)F)cc2)C(C(=O)Nc2cccc(F)c2F)C1=O] |

-continued

| Compound No. | Name | Structure |
|---|---|---|
| 2.9 | 2-oxo-4-[4-(trifluoromethyl)phenyl]-N-(2,3,4-trifluorophenyl)pyrrolidine-3-carboxamide | 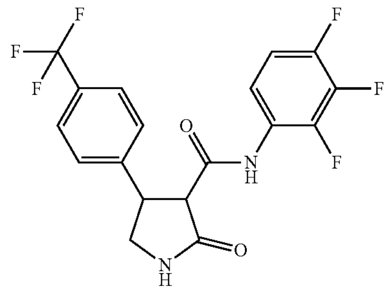 [SMILES: O=C1NCC(c2ccc(C(F)(F)F)cc2)C1C(=O)Nc1ccc(F)c(F)c1F] |
| 2.10 | N-(2-fluorophenyl)-4-(4-fluorophenyl)-1-methyl-2-oxo-pyrrolidine-3-carboxamide | 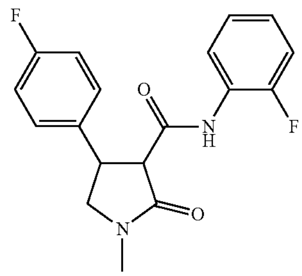 [SMILES: CN1CC(c2ccc(F)cc2)C(C(=O)Nc2ccccc2F)C1=O] |
| 2.11 | N-(2,3-difluorophenyl)-4-(3,4-difluorophenyl)-2-oxo-pyrrolidine-3-carboxamide | 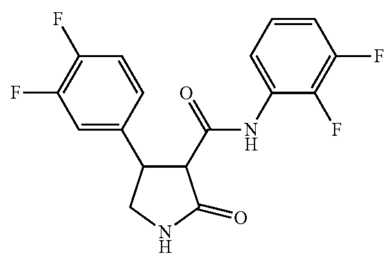 [SMILES: O=C1NCC(c2ccc(F)c(F)c2)C1C(=O)Nc1cccc(F)c1F] |
| 2.12 | 4-(3,4-difluorophenyl)-N-(2-fluorophenyl)-2-oxo-pyrrolidine-3-carboxamide | 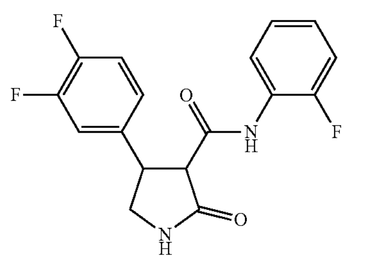 [SMILES: O=C1NCC(c2ccc(F)c(F)c2)C1C(=O)Nc1ccccc1F] |
| 2.13 | N-(2,4-difluorophenyl)-4-(3,5-difluorophenyl)-2-oxo-pyrrolidine-3-carboxamide | 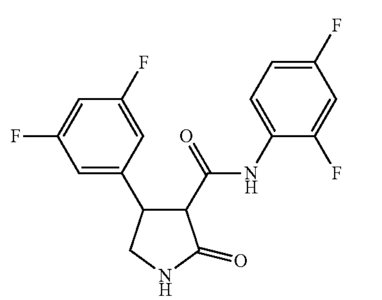 [SMILES: O=C1NCC(c2cc(F)cc(F)c2)C1C(=O)Nc1ccc(F)cc1F] |

| Compound No. | Name | Structure |
|---|---|---|
| 2.14 | N-(2,3-difluorophenyl)-4-(3-isopropylphenyl)-2-oxo-pyrrolidine-3-carboxamide | 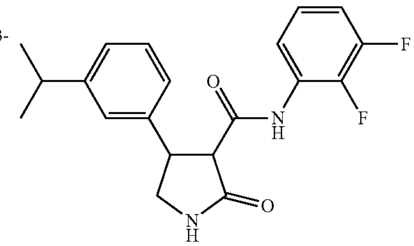 |
| 2.15 | N-(2,3-difluorophenyl)-2-oxo-4-[6-(trifluoromethyl)-3-pyridyl]pyrrolidine-3-carboxamide | 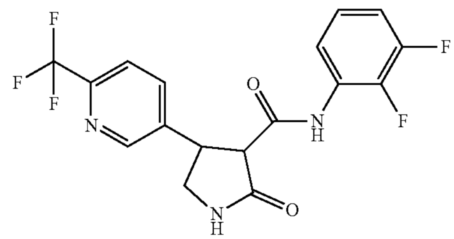 [SMILES: O=C1NCC(c2ccc(C(F)(F)F)nc2)C1C(=O)Nc1cccc(F)c1F] |
| 2.16 | 4-(3,5-difluorophenyl)-N-[3-fluoro-2-(trifluoromethyl)phenyl]-1-methyl-2-oxo-pyrrolidine-3-carboxamide | 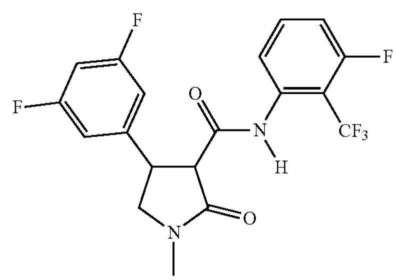 [SMILES: CN1CC(c2cc(F)cc(F)c2)C(C(=O)Nc2cccc(F)c2C(F)(F)F)C1=O] |
| 2.17 | N-(2,4-difluorophenyl)-4-(3,5-difluorophenyl)-1-methyl-2-oxo-pyrrolidine-3-carboxamide | 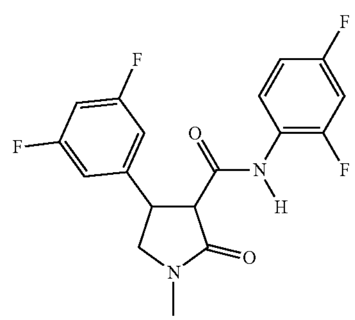 [SMILES: CN1CC(c2cc(F)cc(F)c2)C(C(=O)Nc2ccc(F)cc2F)C1=O] |
| 2.18 | N-(2,3-difluorophenyl)-4-(3,5-difluorophenyl)-1-methyl-2-oxo-pyrrolidine-3-carboxamide | 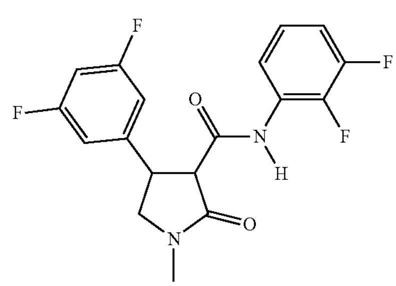 [SMILES: CN1CC(c2cc(F)cc(F)c2)C(C(=O)Nc2cccc(F)c2F)C1=O] |

\* \* \* \* \*